US008012695B2

(12) United States Patent
Kufe

(10) Patent No.: US 8,012,695 B2
(45) Date of Patent: Sep. 6, 2011

(54) METHODS AND COMPOSITIONS RELATING TO PROMOTER REGULATION BY MUC1 AND KLF PROTEINS

(75) Inventor: Donald W. Kufe, Wellesley, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 428 days.

(21) Appl. No.: 12/031,316

(22) Filed: Feb. 14, 2008

(65) Prior Publication Data

US 2009/0098054 A1 Apr. 16, 2009

Related U.S. Application Data

(60) Provisional application No. 60/889,825, filed on Feb. 14, 2007.

(51) Int. Cl.
*G01N 33/53* (2006.01)
(52) U.S. Cl. .................................................... 435/7.1
(58) Field of Classification Search .................. None
See application file for complete search history.

(56) References Cited

U.S. PATENT DOCUMENTS

| 4,522,811 | A | 6/1985 | Eppstein et al. ................ 514/2 |
| 4,642,334 | A | 2/1987 | Moore et al. ............... 530/387.3 |
| 5,565,334 | A | 10/1996 | Kufe et al. ................. 435/69.1 |
| 5,597,457 | A | 1/1997 | Craig et al. .................. 204/165 |
| 5,874,415 | A | 2/1999 | Kufe et al. ..................... 514/44 |
| 6,093,573 | A | 7/2000 | Beamer et al. ................ 436/86 |
| 7,247,297 | B2 | 7/2007 | Weichselbaum et al. .... 424/93.2 |
| 2002/0041868 | A1 | 4/2002 | Nicolette et al. ........... 424/93.21 |
| 2002/0110841 | A1 | 8/2002 | Kufe ............................ 435/7.23 |
| 2004/0018181 | A1 | 1/2004 | Kufe et al. ................. 424/93.21 |
| 2004/0166543 | A1 | 8/2004 | Kufe ............................ 435/7.23 |
| 2005/0015232 | A1 | 1/2005 | Reinherz et al. ................ 702/27 |
| 2005/0042209 | A1 | 2/2005 | Kufe et al. ................ 424/93.21 |
| 2005/0053606 | A1 | 3/2005 | Kufe et al. ................. 424/155.1 |
| 2005/0169898 | A1 | 8/2005 | Gong et al. ............... 424/93.21 |
| 2005/0238627 | A1 | 10/2005 | Ohno et al. ............... 424/93.21 |
| 2007/0105767 | A1 | 5/2007 | Kharbanda et al. ............. 514/12 |
| 2007/0141704 | A1 | 6/2007 | Nicolette et al. ............. 435/455 |
| 2007/0202134 | A1 | 8/2007 | Kufe et al. ................. 424/277.1 |

FOREIGN PATENT DOCUMENTS

| WO | WO 87/02671 | 5/1987 |
| WO | WO 00/09744 | 2/2000 |
| WO | WO 00/11206 | 3/2000 |
| WO | WO 00/47763 | 8/2000 |
| WO | WO 00/72004 | 11/2000 |
| WO | WO 2006/088906 | 8/2006 |

OTHER PUBLICATIONS

Brody et al., "Aptamers as therapeutic and diagnostic agents," *Reviews in Molecular Biotechnology*, 74:5-13, 2000.
Brown et al., "An Sp1/KLF binding site is important for the activity of a Polycomb group response element from the *Drosophila* engrailed gene," *Nucleic Acids Res.*, 33:(16):5181-5189, 2005.
Cohen et al., "Molecular modeling software and methods for medicinal chemistry," *J. Med. Chem.*, 33:883-894, 1990.
Crisitano et al., "Molecular conjugates: a targeted gene delivery vector for molecular medicine," *J. Mol. Med.*, 73:479, 1995.
Emiliani et al., "Characterization of a human RPD3 ortholog, HDAC3," *Proc. Natl. Acad. Sci. USA*, 95:2795-2800, 1998.
Garber, "HDAC inhibitors overcome first hurdle," *Nature Biotechnology*, 25(1):17-19, 2007.
Gendler et al., "A highly immunogenic region of a human polymorphic epithelial mucin expressed by carcinomas is made up of tandem repeats," *J. Biol.Chem.*, 263:12820-12823, 1988.
Ghaleb et al., "Kruppel-like factor 4 exhibits antiapoptotic activity following following [gamma]-radiation-induced DNA damage," *Oncogene,.* 26(16):2365-73, 2007.
Groneborn et al., "Protein structure determination in solution by two-dimensional and three-dimensional nuclear magnetic resonance spectroscopy," *Anal. Chem.* 62(1):2-15, 1990.
Huang et al., "Identification of p53 regulators by genome-wide functional analysis," *Proceedings of the Natonal Academy of Sciences of the United States of America*, 101:3456-3461, 2004.
Huang et al., "MUC1 cytoplasmic domain coactivates Wnt target gene transcription and confers transformation," *Cancer Biol. Ther.*, 2:702-706, 2003.
Hudson et al., "High avidity scFv multimers; diabodies and triabodies," *J. Immunol. Methods*, 23:(1-2):177-189, 1999.
Kaczynski et al., "Sp 1—and Kruppel-like transcription factors," *Genome Biology*, 4:206, 2003.
Kijima et al., "Trapoxin, an antitumor cyclic tetrapeptide, is a irreversible inhibitor of mammalian histone deacetylase," *The Journal of Biological Chemistry*, 268(30):22429-22435, 1993.
Kufe et al., "Differential reactivity of a novel monoclonal anitbody (DF3) with human malignant versus benign breat tumors," *Hybridoma*, 3:223-232, 1984.
Levine et al., "The p53 tumour suppressor gene," *Nature*, 351:453, 1991.
Li et al., "Human DF3/MUC1 carcinoma-associated protein functions as an oncogene," *Oncogene*, 22:6107-6110, 2003.
Li et al., "Interaction of glycogen synthase kinase 3beta with the DF3/MUC1 carcinoma-associated antigen and beta-catenin," *Mol. Cell. Bio.*, 18:7216-7224, 1998.
Li et al., "The c-Src tyrosine kinase regulates signaling of the human DF3/MUC1 carcinoma-associated antigen with GSK3 beta and beta-catenin," *J. Biol. Chem.*, 276:6061-6064, 2001.
Li et al., "The epidermal growth factor receptor regulates interaction of the human DF3/MUC1 carcinoma antigen with c-Src and beta-catenin," *J. Biol. Chem.*, 276:35239-35242, 2001.
Li et al., "Specific targeting and constitutive association of histone deacetylase complexes during transcriptional repression," *Genes Dev.*, 16:687-692, 2002.

(Continued)

*Primary Examiner* — Suzanne M. Noakes
(74) *Attorney, Agent, or Firm* — Fulbright & Jaworski

(57) ABSTRACT

This invention relates to regulation of cell signaling, cell growth, and more particularly to the regulation of cancer or inflammatory cell growth and/or activation. The invention provides methods of, and compositions useful for, inhibiting interactions between MUC1 and a kruppel-like factor (KLF), method of inhibiting interactions between a KLF protein and the p53 promoter, methods of inhibiting the interaction between MUC1 and the p53 promoter, methods of increasing p53 activity, and methods of increasing histone acetylation. The invention also provides screening methods for identifying compounds that inhibit the aforementioned interactions. Pharmaceutical compositions containing the identified compounds can be useful in treating cancers and inflammatory conditions.

2 Claims, 13 Drawing Sheets

OTHER PUBLICATIONS

McPherson, "Crystallization of proteins from polyethylene glycol," *J. Biol. Chem.*, 251:6300-6306, 1976.

Merlo et al., "Frequent alteration of the DF3 tumor-associated antigen gene in primary human breast carcinomas.," *Cancer Res.*, 49:6966-6971, 1989.

Navia et al., "Use of structural information in drug design," *Curr. Opin. Struct. Biol.*, 2:202-210, 1992.

Noda et al., "A unique, short sequence determines p53 gene basal and UV-inducible expression in normal human cells," *Oncogene*, 19:21-31, 2000.

O'Shea-Greenfiend et al., "Roles of TATA and initiator elements in determining the start site location and direction of RNA polymerase II transcription," *J. Biol. Chem.*, 267:6450, 1992.

Poljak, "Production and structure of diabodies," *Structure* 2(12):1121-1123, 1994.

Raina et al., "The MUC1 oncoprotein activates the anti-apoptotic phosphoinositide 3-kinase/Akt and Bcl-$x_L$ pathways in rat 3Y1 fibroblasts," *J. Biol. Chem.*, 279:20607-20612, 2004.

Ren et al., "Human MUC1 carcinoma-associated protein confers resistance to genotoxic anticancer agents," *Cancer Cell*, 5:163-175, 2004.

Rowland et al., "The KLF4 tumour suppressor is a transcriptional repressor of p53 that acts as a context-dependent oncogene," *Nat. Cell Biol.*, 7:1074-1082, 2005.

Rowland et al., "KLF4, p21 and context-dependent opposing forces in cancer," *Nat. Rev. Cancer*, 6:11-23, 2006.

Shang et al., "Cofactor dynamics and sufficiency in estrogen receptor-regulated transcription," *Cell*, 103:843-852, 2000.

Siddiqui et al., "Isolation and sequencing of a cDNA coding for the human DF3 breast carcinoma-associated antigen," *Proc. Natl. Acad. Sci USA*, 85:2320-2323, 1988.

Tuck et al., "Characterization of the human p53 gene promoter," *Mol. Cell Biol.*, 9:2163-2172, 1989.

Warnick et al., "Identification of a p53 response element in the promoter region of the hMSH2 gene required for expression in A2780 ovarian cancer cells," *The Journal of Biological Chemistry*, 276(29):27363-27370, 2001.

Wei et al., "Human MUC1 oncoprotein regulates p53-responsive gene transcription in the genotoxic stress response," *Cancer Cell*, 7:167-178, 2005.

Wei et al., "Ligand-dependent formation of retinoid receptors, receptor-interacting protein 140 (RIP140), and histone deacetylase complex is mediated by a novel receptor-interacting motif of RIP140," *J. Biol. Chem.*, 276:16107-16112, 2001.

Wei et al., "MUC1 oncoprotein stabilizes and activates estrogen receptor alpha," *Mol. Cell*, 21:295-305, 2006.

Wider, "Structure Determination of Biological Macromolecules in Solution Using NMR spectroscopy," *BioTechniques*, 29:1278-1294, 2000.

Xu et al., "Upstream box/TATA box order is the major determinant of the direction of transcription," *Nucleic Acids Res.*, 19:6699-6704, 1991.

Yin et al., "MUC1 oncoprotein activates the FOXO3a transcription factor in a survival response to oxidative stress," *J. Biol. Chem.*, 279:45721-45727, 2004.

Yoon et al., "Kruppel-like factor 4 mediates p53-dependent $G_1$/S cell cycle arrest in response to DNA damage," *The Journal of Biological Chemistry*, 278(4):2101-2105, 2003.

Yoshida et al., "Potent and specific inhibition of mammalian histone deacetylase both in vivo and in vitro by trichostatin A," *J. Biol. Chem.*, 265(28):17174-17179, 1990.

You et al., "Regulation of transactivation-independent proapoptotic activity of p53 by FOXO3a," *PNAS*, 103(24):9051-9056, 2006.

Zhang et al., "Nucleic acid aptamers in human viral disease," *Arch. Immunol. Ther. Exp.*, 52:307-315, 2004.

Zhang et al., "Direct interaction of the Krüppel-like family (KLF) member, BTEB1, and PR mediates progesterone-responsive gene expression in endometrial epithelial cells," *Endocrinology*, 143(1):62-73, 2002.

Evans et al., "Histone acetyltransferase p300 regulates KLF4-mediated transactivation," Poster Abstract: (from Digestive Disease Week Meeting/107th Annual Meeting of the American Gastroenterological Association, May 19-24, 2006). Gastroenterology, 130(4, Suppl. 2):A534, 2006.

International Search Report and Written Opinion, issued in International Application No. PCT/US08/54019, dated Sep. 4, 2008.

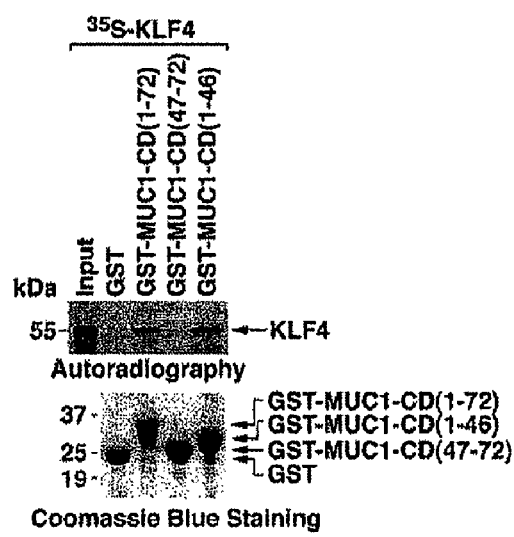
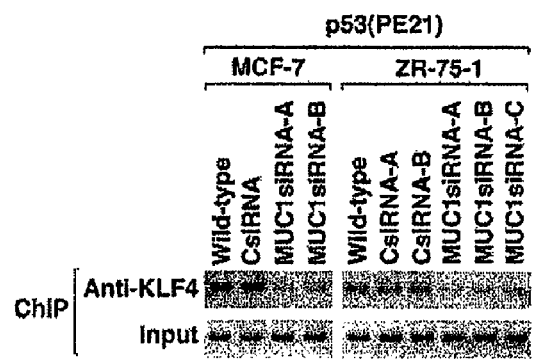
FIG. 3D
FIG. 3E

MAVSDALLPSFSTFASGPAGREKTLRQAGAPNNRWREELSHMKRLPPVLPGRPYDLAA
ATVATDLESGGAGAACGGSNLAPLPRRETEEFNDLLDLDFILSNSLTHPPESVAATVSSS
ASASSSSSPSSSGPASAPSTCSFTYPIRAGNDPGVAPGGTGGGLLYGRESAPPPTAPFNLA
DINDVSPSGGFVAELLRPELDPVYIPPQQPQPPGGGLMGKFVLKASLSAPGSEYGSPSVIS
VSKGSPDGSHPVVVAPYNGGPPRTCPKIKQEAVSSCTHLGAGPPLSNGHRPAAHDFPLG
RQLPSRTTPTLGLEEVLSSRDCHPALPLPPGFHPHPGPNYPSFLPDQMQPQVPPLHYQGQ
SRGFVARAGEPCVCWPHFGTHGMMLTPPSSPLELMPPGSCMPEEPKPKRGRRSWPRKR
TATHTCDYAGCGKTYTKSSHLKAHLRTHTGEKPYHCDWDGCGWKFARSDELTRHYRK
HTGHRPFQCQKCDRAFSRSDHLALHMKRHF

FIG. 9A

GGGAGAAAACGTTAGGGTGTGGATATTACGGAAAGCCTTCCTAAAAAATGACATTT
AACTGATGAGAAGAAAGGATCCAGCTGAGAGCAAACGCAAAAGCTTTCTTCCTTCC
ACCCTTCATATTTGACACAATGCAGGATTCCTCCAAAATGATTTCCACCAATTCTGCC
CTCACAGCTCTGGCTTGCAGAATTTTCCACCCCAAAATGTTAGTATCTACGGCACCA
GGTCGGCGAGAATCCTGACTCTGCACCCTCCTCCCCAACTCCATTTCCTTTGCTTCCT
CCGGCAGGCGGATTACTT<u>GCCCTTACTTGTCATGGCGACTGTCCAGCTTTGTCCAG
GAGCCTCGCAGGGGTTGATGGGATTGGGGTTTTCCCCTCCCATGTGCTCAAGACTGG
CGCTAAAAGTTTTGAGCTTCTCAAAAGTCTAGAGCCACCGTCCAGGGAGCAGGTAG
CTGCTGGGCTCCGGGGACACTTTGCGTTCGGGCTGGGAGCGTGCTTTCCACGACGGT
GACACGCTTCCCTGGATTGG</u>

FIG. 9B

MTPGTQSPFFLLLLLTVLTVVTGSGHASSTPGGEKETSATQRSSVPSSTEKNAIPAPTTTK
SCRETFLKCFCRFINKGVFWASPILSSVSDVPFPFSAQSGAGVPGWGIALLVLVCVLVAL
AIVYLIALAVCQCRRKNYGQLDIFPARDTYHPMSEYPTYHTHGRYVPPSSTDRSPYEKVS
AGNGGSSLSYTNPAVAATSANL

FIG. 9C

```
 1        10        20        30        40        50        60      72
CQCRRKNYGQLDIFPARDTYHPMSEYPTYHTHGRYVPPSSTDRSPYEKVSAGNGGSSLSYTNPAVAAASANL  MUC1-CD
━━━━━━━━━━━━━━━━━━━━━━━━━━━━━━━━━━━━━━━━━━━━━                            MUC1-CD(1-45)
                                             ━━━━━━━━━━━━━━━━━━━━━━━━━━  MUC1-CD(46-72)
```

FIG. 9D

SEQUENCE LISTING

```
<160> NUMBER OF SEQ ID NOS: 7

<210> SEQ ID NO 1
<211> LENGTH: 203
<212> TYPE: PRT
<213> ORGANISM: Homo sapiens

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Ile Pro Ala Pro Thr Thr Thr Lys Ser Cys Arg
    50                  55                  60

Glu Thr Phe Leu Lys Cys Phe Cys Arg Phe Ile Asn Lys Gly Val Phe
65                  70                  75                  80

Trp Ala Ser Pro Ile Leu Ser Ser Val Ser Asp Val Pro Phe Pro Phe
                85                  90                  95

Ser Ala Gln Ser Gly Ala Gly Val Pro Gly Trp Gly Ile Ala Leu Leu
            100                 105                 110

Val Leu Val Cys Val Leu Val Ala Leu Ala Ile Val Tyr Leu Ile Ala
        115                 120                 125

Leu Ala Val Cys Gln Cys Arg Arg Lys Asn Tyr Gly Gln Leu Asp Ile
    130                 135                 140

Phe Pro Ala Arg Asp Thr Tyr His Pro Met Ser Glu Tyr Pro Thr Tyr
145                 150                 155                 160

His Thr His Gly Arg Tyr Val Pro Pro Ser Ser Thr Asp Arg Ser Pro
                165                 170                 175
```

Tyr Glu Lys Val Ser Ala Gly Asn Gly Gly Ser Ser Leu Ser Tyr Thr
                 180                 185                 190

Asn Pro Ala Val Ala Ala Thr Ser Ala Asn Leu
            195                 200

<210> SEQ ID NO 2
<211> LENGTH: 72
<212> TYPE: PRT
<213> ORGANISM: Homo sapiens

<400> SEQUENCE: 2

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Ser Ala Asn Leu
65                  70

<210> SEQ ID NO 3
<211> LENGTH: 40
<212> TYPE: PRT
<213> ORGANISM: Homo sapiens

<400> SEQUENCE: 3

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser
        35                  40

<210> SEQ ID NO 4
<211> LENGTH: 27
<212> TYPE: PRT
<213> ORGANISM: Homo sapiens

<400> SEQUENCE: 4

Tyr Glu Lys Val Ser Ala Gly Asn Gly Gly Ser Ser Leu Ser Tyr Thr
1               5                   10                  15

Asn Pro Ala Val Ala Ala Ala Ser Ala Asn Leu
            20                  25

<210> SEQ ID NO 5
<211> LENGTH: 532
<212> TYPE: DNA
<213> ORGANISM: Homo sapiens

<400> SEQUENCE: 5
gggagaaaac gttagggtgt ggatattacg gaaagccttc ctaaaaaatg acatttaact     60
gatgagaaga aaggatccag ctgagagcaa acgcaaaagc tttcttcctt ccacccttca    120
tatttgacac aatgcaggat tcctccaaaa tgatttccac caattctgcc ctcacagctc    180
tggcttgcag aatttttccac cccaaaaatgt tagtatctac ggcaccaggt cggcgagaat    240
cctgactctg cacctcctc cccaactcca tttcctttgc ttcctccggc aggcggatta    300
cttgccctta cttgtcatgg cgactgtcca gctttgtgcc aggagcctcg caggggttga    360

-continued

```
tgggattggg gttttcccct cccatgtgct caagactggc gctaaaagtt ttgagcttct    420
caaaagtcta gagccaccgt ccagggagca ggtagctgct gggctccggg gacactttgc    480
gttcgggctg ggagcgtgct ttccacgacg gtgacacgct tccctggatt gg            532
```

<210> SEQ ID NO 6
<211> LENGTH: 65
<212> TYPE: DNA
<213> ORGANISM: Homo sapiens

<400> SEQUENCE: 6

```
gcccttactt gtcatggcga ctgtccagct ttgtgccagg agcctcgcag gggttgatgg    60
gattg                                                                65
```

<210> SEQ ID NO 7
<211> LENGTH: 504
<212> TYPE: PRT
<213> ORGANISM: Homo sapiens

<400> SEQUENCE: 7

```
Met Ala Val Ser Asp Ala Leu Leu Pro Ser Phe Ser Thr Phe Ala Ser
1               5                   10                  15

Gly Pro Ala Gly Arg Glu Lys Thr Leu Arg Gln Ala Gly Ala Pro Asn
            20                  25                  30

Asn Arg Trp Arg Glu Glu Leu Ser His Met Lys Arg Leu Pro Pro Val
        35                  40                  45

Leu Pro Gly Arg Pro Tyr Asp Leu Ala Ala Ala Thr Val Ala Thr Asp
    50                  55                  60

Leu Glu Ser Gly Gly Ala Gly Ala Ala Cys Gly Gly Ser Asn Leu Ala
65                  70                  75                  80

Pro Leu Pro Arg Arg Glu Thr Glu Glu Phe Asn Asp Leu Leu Asp Leu
                85                  90                  95

Asp Phe Ile Leu Ser Asn Ser Leu Thr His Pro Pro Glu Ser Val Ala
            100                 105                 110

Ala Thr Val Ser Ser Ser Ala Ser Ala Ser Ser Ser Ser Pro Ser
        115                 120                 125

Ser Ser Gly Pro Ala Ser Ala Pro Ser Thr Cys Ser Phe Thr Tyr Pro
130                 135                 140

Ile Arg Ala Gly Asn Asp Pro Gly Val Ala Pro Gly Gly Thr Gly Gly
145                 150                 155                 160

Gly Leu Leu Tyr Gly Arg Glu Ser Ala Pro Pro Thr Ala Pro Phe
                165                 170                 175

Asn Leu Ala Asp Ile Asn Asp Val Ser Pro Ser Gly Gly Phe Val Ala
            180                 185                 190

Glu Leu Leu Arg Pro Glu Leu Asp Pro Val Tyr Ile Pro Pro Gln Gln
        195                 200                 205

Pro Gln Pro Pro Gly Gly Gly Leu Met Gly Lys Phe Val Leu Lys Ala
    210                 215                 220

Ser Leu Ser Ala Pro Gly Ser Glu Tyr Gly Ser Pro Ser Val Ile Ser
225                 230                 235                 240

Val Ser Lys Gly Ser Pro Asp Gly Ser His Pro Val Val Val Ala Pro
                245                 250                 255

Tyr Asn Gly Gly Pro Pro Arg Thr Cys Pro Lys Ile Lys Gln Glu Ala
            260                 265                 270

Val Ser Ser Cys Thr His Leu Gly Ala Gly Pro Pro Leu Ser Asn Gly
        275                 280                 285
```

-continued

```
His Arg Pro Ala Ala His Asp Phe Pro Leu Gly Arg Gln Leu Pro Ser
    290                 295                 300
Arg Thr Thr Pro Thr Leu Gly Leu Glu Glu Val Leu Ser Ser Arg Asp
305                 310                 315                 320
Cys His Pro Ala Leu Pro Leu Pro Pro Gly Phe His Pro His Pro Gly
                325                 330                 335
Pro Asn Tyr Pro Ser Phe Leu Pro Asp Gln Met Gln Pro Gln Val Pro
            340                 345                 350
Pro Leu His Tyr Gln Gly Gln Ser Arg Gly Phe Val Ala Arg Ala Gly
        355                 360                 365
Glu Pro Cys Val Cys Trp Pro His Phe Gly Thr His Gly Met Met Leu
    370                 375                 380
Thr Pro Pro Ser Ser Pro Leu Glu Leu Met Pro Pro Gly Ser Cys Met
385                 390                 395                 400
Pro Glu Glu Pro Lys Pro Lys Arg Gly Arg Arg Ser Trp Pro Arg Lys
                405                 410                 415
Arg Thr Ala Thr His Thr Cys Asp Tyr Ala Gly Cys Gly Lys Thr Tyr
            420                 425                 430
Thr Lys Ser Ser His Leu Lys Ala His Leu Arg Thr His Thr Gly Glu
        435                 440                 445
Lys Pro Tyr His Cys Asp Trp Asp Gly Cys Gly Trp Lys Phe Ala Arg
    450                 455                 460
Ser Asp Glu Leu Thr Arg His Tyr Arg Lys His Thr Gly His Arg Pro
465                 470                 475                 480
Phe Gln Cys Gln Lys Cys Asp Arg Ala Phe Ser Arg Ser Asp His Leu
                485                 490                 495
Ala Leu His Met Lys Arg His Phe
            500
```

METHODS AND COMPOSITIONS RELATING TO PROMOTER REGULATION BY MUC1 AND KLF PROTEINS

This application claims the benefit of the filing date of U.S. provisional patent application Ser. No. 60/889,825, filed Feb. 14, 2007, the entire content of which is hereby incorporated by reference.

The research described in this application was supported by grant nos. CA28431 and CA97098 from the National Cancer Institute of the National Institutes of Health. Thus, the government has certain rights in the invention.

BACKGROUND OF THE INVENTION

I. Field of the Invention

This invention relates to regulation of cell signaling, cell growth and particularly to the regulation of cancer or cell growth.

II. Description of Related Art

The MUC1 heterodimeric mucin-type glycoprotein is expressed on the apical borders of secretory epithelial cells (Kufe et al. (1984) Hybridoma 3: 223-232). With transformation and loss of polarity, MUC1 is expressed at high levels over the entire cell membrane and in the cytoplasm (Kufe et al. (1984) Hybridoma 3: 223-232). The MUC1 N-terminal ectodomain, which consists of variable numbers of 20 amino acid tandem repeats that are extensively modified by O-linked glycans, is tethered to the cell surface through a complex with the MUC1 C-terminal transmembrane subunit (MUC1-C) (Siddiqui et al. (1988) Proc. Natl. Acad. Sci. USA 85: 2320-2323; Gendler et al. (1988) J. Biol. Chem. 263: 12820-12823; and Merlo et al. (1989) Cancer Res. 49: 6966-6971). MUC1-C integrates receptor tyrosine kinase signaling with the Wnt pathway (Li et al. (1998) Mol. Cell. Biol. 18: 7216-7224; Li et al. (2001) J. Biol. Chem. 276: 35239-35242; and Li et al. (2001) J. Biol. Chem. 276: 6061-6064). MUC1-C is also targeted to mitochondria and to the nucleus, where it contributes to the regulation of β-catenin/Tcf- and p53-mediated gene transcription (Ren et al. (2004) Cancer Cell 5: 163-175; Huang et al. (2003) Cancer Biol. Ther. 2: 702-706; and Wei et al. (2005) Cancer Cell 7: 167-178). Overexpression of MUC1 is sufficient to induce transformation and to attenuate apoptosis in the response of cells to oxidative and genotoxic stress (Ren et al. (2004) Cancer Cell 5: 163-175; Huang et al. (2003) Cancer Biol. Ther. 2: 702-706; Li et al. (2003) Oncogene 22: 6107-6110; Raina et al. (2004) J. Biol. Chem. 279: 20607-20612; and Yin et al. (2004) J. Biol. Chem. 279: 45721-45727).

The p53 transcription factor (or "p53") is of key importance in the protection of an organism against carcinogenesis. p53 performs this function by regulating several cellular processes, the most important of which are apoptosis and cell-cycle progression. The p53 transcription factor is a nuclear phosphoprotein involved in the control of cell proliferation, and mutations in the p53 gene are commonly found to be associated with diverse type of human cancer (Levine et al. (1991) Nature 351: 453).

SUMMARY OF THE INVENTION

This invention is based, at least in part, on the discovery that MUC1 binds to kruppel-like factor 4 (KLF4) and potentiates KLF4-mediated suppression of the p53 promoter. p53 is a tumor suppressor protein that is mutated or inactivated in over 50% of all human cancers. Thus, the findings described herein indicate that, inter alia, inhibition of MUC1-KLF4 interaction could be beneficial in treating cancers. Since the p53 and MUC1 pathways are implicated not only in regulating cancer cell growth (and viability) but also regulation of the growth and viability of inflammatory cells (e.g., immune cells), inhibition of MUC1-KLF interactions could also be useful in the treatment of inflammatory conditions (e.g., autoimmune disorders or any of the inflammatory conditions described herein).

The disclosure features a method of identifying a compound that inhibits the binding of MUC1 to a KLF (e.g., KLF4). The method includes the steps of: contacting a MUC1 reagent with a KLF reagent in the presence of a candidate compound; and determining whether the candidate compound inhibits binding of the MUC1 reagent to the KLF reagent. In some embodiments, the contacting of the MUC1 reagent with the KLF reagent in the presence of the candidate compound occurs in the further presence of a p53 promoter reagent. The method can optionally include the step of providing a MUC1 reagent, a KLF reagent, and/or a p53 promoter reagent. The method can be performed (i.e., carried out) in a cell or in a cell-free system. In embodiments where the method is carried out in a cell, cells suitable for the method can be any prokaryotic cell (e.g., a bacterial cell) or eukaryotic cell (e.g., a yeast cell, a nematode cell, an insect cell, a bird cell, a mammalian cell (e.g., a mouse cell, a rat cell, a guinea pig cell, a horse cell, a cow cell, a pig cell, a goat cell, a donkey cell, a monkey cell, or a human cell)). MUC1 reagents can include any agent containing a full-length, wild-type, mature MUC1 or the MUC1-cytoplasmic domain (MUC1-CD) (SEQ ID NO:2), or fragments (e.g., functional fragments) of the full-length, wild-type, MUC1 or MUC1-CD (see below), such as amino acids 1-46 of the MUC1-CD as depicted in SEQ ID NO:3. The p53 promoter reagent can be, or include, the human p53 promoter (SEQ ID NO:5) or the PE21 element (e.g., SEQ ID NO:6) of a human p53 promoter. The KLF reagent can be, or contain, KLF4 or a MUC1- or p53 promoter-binding fragment thereof. The KLF4 can be, or contain, SEQ ID NO:7.

Also featured is a process of manufacturing a compound, which includes the steps of, after determining that a compound inhibits the interaction between MUC1 and a KLF (through the preceding method), manufacturing the compound.

The disclosure also provides a method of identifying a compound that inhibits the binding of MUC1 to the p53 promoter, which method includes the steps of: contacting a MUC1 reagent with a p53 promoter reagent in the presence of a candidate compound, and determining whether the candidate compound inhibits binding of the MUC1 reagent to the p53 promoter reagent. In some embodiments, the contacting of the MUC1 reagent with the p53 reagent in the presence of the candidate compound occurs in the further presence of a KLF reagent. The method can also include the step of providing a MUC1 reagent, a KLF reagent, and/or a p53 promoter reagent. The method can be performed (i.e., carried out) in a cell or in a cell-free system. The cell can be any of those described herein. The MUC1, KLF, and p53 reagents can be any of those described herein.

Also provided is a process of manufacturing a compound, which includes the steps of, after determining that a compound inhibits the interaction between MUC1 and a p53 promoter (through the preceding method), manufacturing the compound.

The disclosure also features a method of generating a compound that inhibits the interaction between MUC1 and a KLF. The method includes the steps of: providing a three-dimensional structure of a molecule or a molecular complex comprising: (a) the cytoplasmic domain of MUC1 or a KLF-binding fragment thereof; (b) a molecule comprising a KLF or a MUC1-binding fragment thereof; or (c) a molecular complex comprising (a) and (b); designing, based on the three-dimensional structure, a compound comprising a region that inhibits the interaction between MUC1 and a KLF; and producing the compound. In some embodiments, the molecular complex (c) can further contain a p53 promoter or a fragment thereof, where the fragment binds to the MUC1 (e.g., the MUC1-CD) or the KLF (e.g., KLF4). The p53 promoter can be, or include, the human p53 promoter (SEQ ID NO:5) or the PE21 element (e.g., SEQ ID NO:6) of a human p53 promoter. The KLF can be, or contain, KLF4 or a MUC1- or p53 promoter-binding fragment thereof. The KLF4 can be, or contain, SEQ ID NO:7.

Also featured is a method of generating a compound that inhibits the interaction between MUC1 and the p53 promoter, which method includes the steps of: providing a three-dimensional structure of a molecule or a molecular complex comprising: (a) the cytoplasmic domain of MUC1 or a p53 promoter-binding fragment thereof; (b) a molecule comprising p53 promoter or a MUC1-binding fragment thereof; or (c) a molecular complex comprising (a) and (b); designing, based on the three-dimensional structure, a compound comprising a region that inhibits the interaction between MUC1 and the p53 promoter; and producing the compound. In some embodiments, the molecular complex (c) further contains a KLF (e.g., KLF4) or fragment thereof, wherein the fragment binds to MUC1 or the p53 promoter. MUC1 can be, or contain, the MUC1-CD (e.g., the MUC1-CD as depicted in SEQ ID NO:2) or a functional fragment of the MUC1-CD (e.g., SEQ ID NO:3). The p53 promoter can be, or include, the human p53 promoter (SEQ ID NO:5) or the PE21 element (e.g., SEQ ID NO:6) of a human p53 promoter. The KLF can be, or contain, KLF4 or a MUC1- or p53 promoter-binding fragment thereof. The KLF4 can be, or contain, SEQ ID NO:7.

The disclosure also features a compound, and pharmaceutical compositions thereof, identified by any of the methods described herein.

Also provided is an in vitro method of inhibiting an interaction between MUC1 and a KLF, which method includes the steps of: contacting (i) a MUC1 reagent; (ii) a KLF reagent; or (iii) a molecular complex comprising (i) and (ii) with a compound that inhibits the interaction between MUC1 and a KLF. In some embodiments, the contacting can occur in the further presence of a p53 promoter reagent. The KLF reagent can be, or contain, KLF4 (e.g., SEQ ID NO:7) or a MUC1-binding fragment thereof. The MUC1 reagent can be, or contain, the MUC1-CD (e.g., SEQ ID NO:2) or a functional fragment thereof (e.g., SEQ ID NO:3). The p53 promoter reagent can be, or contain, a PE21 element (e.g., SEQ ID NO:6) of a p53 promoter (e.g., SEQ ID NO:5). The contacting can occur in a cell. The cell can be any of those described herein.

Also featured is an in vitro method of inhibiting an interaction between MUC1 and a p53 promoter. The method includes the steps of: contacting (i) a MUC1 reagent; (ii) a p53 promoter reagent, or (iii) a molecular complex comprising (i) and (ii) with a compound that inhibits the interaction between MUC1 and the p53 promoter. In some embodiments, the contacting can occur in the further presence of a KLF reagent. The KLF reagent can be, or contain, KLF4 (e.g., SEQ ID NO:7) or a MUC1-binding fragment thereof. The MUC1 reagent can be, or contain, the MUC1-CD (e.g., SEQ ID NO:2) or a functional fragment thereof (e.g., SEQ ID NO:3). The p53 promoter reagent can be, or contain, a PE21 element (e.g., SEQ ID NO:6) of a p53 promoter (e.g., SEQ ID NO:5). The contacting can occur in a cell. The cell can be any of those described herein. The interaction between MUC1 and a p53 promoter can be a direct physical interaction between MUC1 and the p53 promoter or can be indirect, e.g., mediated by one or more additional polypeptides such as a KLF (e.g., KLF4).

The disclosure also provides an in vitro method of inhibiting an interaction between MUC1 and a KLF. The method includes the steps of: optionally identifying a cell as one expressing a KLF (e.g., KLF4) and/or MUC1; and culturing the cell with a compound that inhibits MUC1. The method can also include the step of determining whether inhibition of an interaction between MUC1 and a KLF occurred.

Also provided is an in vitro method of inhibiting an interaction between MUC1 and a KLF, which method includes the steps of: optionally identifying a cell as one expressing MUC1 and/or a KLF (e.g., KLF4), and culturing the cell with a compound that inhibits a KLF. The method can also include the step of determining whether inhibition of an interaction between MUC1 and a KLF occurred.

Also provided is an in vitro method of inhibiting an interaction between MUC1 and a p53 promoter. The method includes the steps of: optionally identifying a cell as one expressing a KLF and/or MUC1; and culturing the cell with a compound that inhibits an interaction between MUC1 and a p53 promoter. The method can also include the step of determining whether inhibition of an interaction between MUC1 and a p53 promoter occurred. The interaction between MUC1 and a p53 promoter can be a direct physical interaction between MUC1 and the p53 promoter or can be indirect, e.g., mediated by one or more additional polypeptides such as a KLF (e.g., KLF4).

Also provided is an in vitro method of inhibiting an interaction between KLF (e.g., KLF4) and a p53 promoter. The method includes the steps of: optionally identifying a cell as one expressing MUC1, and culturing the cell with a compound that inhibits an interaction between KLF4 and a p53 promoter. The method can also include the step of determining whether inhibition of an interaction between KLF4 and a p53 promoter occurred.

The disclosure also provides an in vitro method of increasing histone acetylation. The method includes the steps of: optionally identifying a cell as one expressing a KLF (e.g., KLF4) and/or a MUC1, culturing the cell with a compound that inhibits MUC1, and detecting whether an increase in p53 promoter histone acetylation occurred.

Also featured is an in vitro method of inhibiting an interaction between an HDAC and a p53 promoter. The method includes the steps of: optionally identifying a cell as one expressing MUC1, culturing the cell with a compound that inhibits an interaction between an HDAC and a p53 promoter, and optionally detecting whether an inhibition of an interaction between an HDAC and a p53 promoter has occurred. In some embodiments, the compound can inhibit transcription of a MUC1 coding sequence or can inhibit translation of a MUC1 mRNA. The HDAC can be HDAC1, HDAC2, HDAC3, or HDAC4. The interaction between an HDAC and a p53 promoter can be a direct physical interaction between the HDAC and the p53 promoter or can be indirect, e.g., mediated by one or more additional polypeptides such as a KLF (e.g., KLF4) and/or MUC1. The compound can be one that inhibits MUC1 or a KLF (e.g., KLF4).

The disclosure also provides an in vitro method of inhibiting an interaction between an HDAC and a p53 promoter, which method includes the steps of: optionally identifying a cell as one expressing KLF4, culturing the cell with a compound that inhibits an interaction between an HDAC and a p53 promoter, and optionally detecting whether an inhibition of an interaction between an HDAC and a p53 promoter has occurred. In some embodiments, the compound can inhibit transcription of a KLF coding sequence or can inhibit translation of a KLF mRNA. The KLF can be KLF4. The HDAC can be HDAC1, HDAC2, HDAC3, or HDAC4. The interaction between an HDAC and a p53 promoter can be a direct physical interaction between the HDAC and the p53 promoter or can be indirect, e.g., mediated by one or more additional polypeptides such as a KLF (e.g., KLF4) and/or MUC1. The compound can be one that inhibits MUC1 or a KLF (e.g., KLF4).

Also featured is an in vitro method of increasing p53 activity. The method includes the steps of: optionally identifying a cell as one expressing a KLF and/or MUC1, culturing the cell with a compound that inhibits MUC1, and detecting whether an increase in p53 activity occurred. An increase in p53 activity is an increase in p53 expression (e.g., p53 mRNA or p53 protein expression). An increase in p53 activity is an increase in the level of expression of a p53-transactivated gene such as, but not limited to, p21, BAX, MDM2, GADD45, 14-3-3 sigma, FAS1, FASL, or Pirh2.

Also provided is an in vitro method of inhibiting histone deacetylation, which method includes the steps of: optionally identifying a cell as one expressing MUC1, and culturing the cell with a compound that inhibits a histone deacetylase (HDAC). The HDAC can be HDAC1, HDAC2, HDAC3, or HDAC4. The compound can be butyrate, depsipeptide, phenylbutyrate, valproate, a trichostatin, suberoylanilide hydroxamic acid (SAHA), azelaic bishydroxamic acid (ABHA), scriptaid, pyroxamide, chlamydocin, apicidin, depudecin, MS-275, MGCD0103, PXD101, Daceca, Savisol, LBH589, PCI-24781, and ITF2357.

Also featured is an in vitro method of inhibiting an interaction between a KLF and a PE21 element. The method includes the steps of: optionally identifying a cell as one expressing MUC1 and/or a KLF, and culturing the cell with a compound that inhibits an interaction between a KLF and a PE21 element. The method can include the step of detecting whether inhibition of an interaction between a KLF and a PE21 element occurred. The KLF can be KLF4. The PE21 element can be a PE21 element from a p53 promoter. The p53 promoter can be a human p53 promoter (e.g., the p53 promoter sequence as depicted in SEQ ID NO:5). The PE21 element can have the SEQ ID NO:6.

Also featured is an in vitro method of inhibiting an interaction between MUC1 and a PE21 element. The method includes the steps of: optionally identifying a cell as one expressing MUC1 and/or a KLF; culturing the cell with a compound that inhibits an interaction between MUC1 and a PE21 element. The method can include the step of detecting whether inhibition of an interaction between a KLF and a PE21 element occurred. The KLF can be KLF4. The PE21 element can be a PE21 element from a p53 promoter. The p53 promoter can be a human p53 promoter (e.g., the p53 promoter sequence as depicted in SEQ ID NO:5). The PE21 element can have the SEQ ID NO:6. The interaction between MUC1 and a PE21 element can be a direct, physical interaction between MUC1 and the PE21 element or the interaction can be indirect, e.g., mediated by one or more additional polypeptides such as a KLF (e.g., KLF4).

In any of the cell-based in vitro methods described herein, the cell can be a human cell. The cell can be a cancer cell such as a lung cancer cell, a breast cancer cell, a colon cancer cell, a pancreatic cancer cell, a renal cancer cell, a stomach cancer cell, a liver cancer cell, a bone cancer cell, a hematological cancer cell, a neural tissue cancer cell, a melanoma cell, a thyroid cancer cell, an ovarian cancer cell, a testicular cancer cell, a prostate cancer cell, a cervical cancer cell, a vaginal cancer cell, or a bladder cancer cell.

The disclosure also features an in vivo method of inhibiting an interaction between MUC1 and a KLF. The method includes the steps of: providing a subject having, at risk of developing, or suspected of having, a cancer comprising one or more cells expressing a KLF or MUC1, and delivering to the subject a compound that inhibits an interaction between MUC1 and a KLF. The method can include the step of identifying a subject as one having, suspected of having, or at risk of developing a cancer comprising one or more cancer cells expressing MUC1 and/or a KLF. The method can also include the step of determining whether the one or more cancer cells of the subject's cancer express MUC1 and/or a KLF. The method can also include the step of determining whether inhibiting of an interaction between MUC1 and a KLF occurred.

Also featured is an in vivo method of inhibiting an interaction between MUC1 and a p53 promoter. The method includes the steps of: providing a subject having, at risk of developing, or suspected of having, a cancer comprising one or more cells expressing a KLF and/or MUC1, and delivering to the subject a compound that inhibits an interaction between MUC1 and the p53 promoter. The method can include the step of identifying a subject as one having, suspected of having, or at risk of developing a cancer comprising one or more cancer cells expressing MUC1 and/or a KLF. The method can also include the step of determining whether the one or more cancer cells of the subject's cancer express MUC1 and/or a KLF. The method can also include the step of determining whether inhibition of an interaction between MUC1 and the p53 promoter occurred.

Also featured is an in vivo method of inhibiting an interaction between a KLF and a p53 promoter. The method includes the steps of: providing a subject having, at risk of developing, or suspected of having, a cancer comprising one or more cells expressing MUC1 and/or a KLF; and delivering to the subject a compound that inhibits an interaction between a KLF (e.g., KLF4) and a p53 promoter. The method can include the step of identifying a subject as one having, suspected of having, or at risk of developing a cancer comprising one or more cancer cells expressing MUC1 and/or a KLF. The method can also include the step of determining whether the one or more cancer cells of the subject's cancer express MUC1 and/or a KLF. The method can also include the step of determining whether inhibition of an interaction between KLF (e.g., KLF4) and the p53 promoter occurred.

The disclosure also provides an in vivo method of increasing p53 activity, which method includes the steps of: providing a subject having, at risk of developing, or suspected of having, a cancer comprising one or more cells expressing a KLF and/or MUC1, delivering to the subject a compound that inhibits MUC1 and/or a KLF, and optionally detecting whether an increase in p53 activity occurred. The method can include the step of identifying a subject as one having, suspected of having, or at risk of developing a cancer comprising one or more cancer cells expressing MUC1 and/or a KLF. The method can also include the step of determining whether the one or more cancer cells of the subject's cancer express MUC1 and/or a KLF. The compound can inhibit the expression of MUC1 or a KLF. The compound can inhibit transcription of a MUC1 gene or a KLF gene. The compound can inhibit translation of a MUC1 mRNA or a KLF mRNA.

Also featured is an in vivo method of inhibiting histone deacetylation. The method includes the steps of: providing a subject having, at risk of developing, or suspected of having, a cancer comprising one or more cells expressing MUC1 and/or a KLF, and delivering to the subject a compound that inhibits an HDAC. The method can include the step of identifying a subject as one having, suspected of having, or at risk of developing a cancer comprising one or more cancer cells expressing MUC1 and/or a KLF. The method can also include the step of determining whether the one or more cancer cells of the subject's cancer express MUC1 and/or a KLF. The method can also include the step of determining whether inhibition of an HDAC occurred. The HDAC can be HDAC1, HDAC2, HDAC3, or HDAC4. The compound can be butyrate, depsipeptide, phenylbutyrate, valproate, a trichostatin, suberoylanilide hydroxamic acid (SAHA), azelaic bishydroxamic acid (ABHA), scriptaid, pyroxamide, chlamydocin, apicidin, depudecin, MS-275, MGCD0103, PXD101, Daceca, Savisol, LBH589, PCI-24781, and ITF2357.

Also featured in an in vivo method of inhibiting an interaction between an HDAC and a p53 promoter. The method includes the steps of: providing a subject having, suspected of having, or at risk of developing, a cancer comprising one or more cells expressing MUC1, delivering to the subject a compound that inhibits an interaction between an HDAC and a p53 promoter, and optionally detecting whether an inhibition of an interaction between an HDAC and a p53 promoter occurred. The method can include the step of identifying a subject as one having, suspected of having, or at risk of developing, a cancer comprising one or more cells expressing MUC1. The method can also include the steps of determining whether one or more of the cancer cells of the subject's cancer express MUC1. The compound can inhibit MUC1 or a KLF. The compound can inhibit transcription of a MUC1 coding sequence or can inhibit translation of a MUC1 mRNA. The HDAC can be HDAC1, HDAC2, HDAC3, or HDAC4. The interaction between an HDAC and a p53 promoter can be a direct, physical interaction between the HDAC and the p53 promoter or can be indirect, e.g., mediated by one or more additional polypeptides such as a KLF (e.g., KLF4) and/or MUC1.

The disclosure also provides an in vivo method of inhibiting an interaction between an HDAC and a p53 promoter, which method includes the steps of: providing a subject having, suspected of having, or at risk of developing, a cancer comprising one or more cells expressing a KLF (e.g., KLF4); delivering to the subject a compound that inhibits an interaction between an HDAC and a p53 promoter; and detecting whether an inhibition of an interaction between an HDAC and a p53 promoter has occurred. The method can include the step of identifying a subject as one having, suspected of having, or at risk of developing, a cancer comprising one or more cells expressing MUC1. The method can also include the steps of determining whether one or more of the cancer cells of the subject's cancer express MUC1. The compound can inhibit transcription of a KLF coding sequence or can inhibit translation of a KLF mRNA. The HDAC can be HDAC 1, HDAC2, HDAC3, or HDAC4. The KLF can be KLF4. The interaction between an HDAC and a p53 promoter can be a direct, physical interaction between the HDAC and the p53 promoter or can be indirect, e.g., mediated by one or more additional polypeptides such as a KLF (e.g., KLF4) and/or MUC1.

Also featured is an in vivo method of inhibiting an interaction between MUC1 and a PE21 element. The method includes the steps of: providing a subject having, or suspected of having, a cancer comprising one or more cells expressing MUC1 and/or a KLF, and delivering to the subject a compound that inhibits an interaction between MUC1 and a PE21 element. The method can include the step of identifying a subject as one having, suspected of having, or at risk of developing a cancer comprising one or more cancer cells expressing MUC1 and/or a KLF. The method can also include the step of determining whether the one or more cancer cells of the subject's cancer express MUC1 and/or a KLF. The method can also include the step of determining whether inhibition of an interaction between MUC1 and a PE21 element occurred. The PE21 element can be a PE21 element from a p53 promoter. The p53 promoter can be a human p53 promoter (e.g., the p53 promoter sequence as depicted in SEQ ID NO:5). The PE21 element can have the SEQ ID NO:6.

Also featured is an in vivo method of inhibiting an interaction between a KLF and a PE21 element. The method includes the steps of: providing a subject having, or suspected of having, a cancer comprising one or more cells expressing MUC1 and/or a KLF, and delivering to the subject a compound that inhibits an interaction between a KLF and a PE21 element. The method can include the step of identifying a subject as one having, suspected of having, or at risk of developing a cancer comprising one or more cancer cells expressing MUC1 and/or a KLF. The method can also include the step of determining whether the one or more cancer cells of the subject's cancer express MUC1 and/or a KLF. The method can also include the step of determining whether inhibition of an interaction between a KLF and a PE21 element occurred. The PE21 element can be a PE21 element from a p53 promoter. The p53 promoter can be a human p53 promoter (e.g., the p53 promoter sequence as depicted in SEQ ID NO:5). The PE21 element can have the SEQ ID NO:6. The KLF can be KLF4.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC) or has been exposed to conditions that can result in cancer. Thus, a subject can also be one "at risk of developing a cancer" when the subject has been exposed to mutagenic or carcinogenic levels of certain compounds (e.g., carcinogenic compounds in cigarette smoke such as Acrolein, 4-Aminobiphenyl, Aromatic Amines, Aromatic Nitrohydrocarbons, Arsenic, Benzene, Benz{a}anthracene, Benzo{a}pyrene, Benzo {b}fluoranthene, Benzo {c}phenanthrene, Benzo{e}pyrene, Benzo{j}fluoranthene, Cadmium, Chromium, Chrysene, Dibenz{a,j}acridine, Dibenz {a,c}anthracene, Dibenz {a,h}acridine, Dibenzo {a,h}pyrene, Dibenzo {a,i}pyrene, Dibenzo {c,g}carbazole, Dichlorostilbene, 4-Ethycatechol, Formaldehyde, Hydrazine, Indeno{1,2,3-cd}pyrene, Methylchrysene, Methylfluoranthene, Methylnaphtalenes, 1-Methylindoles, 3-Methylcatechol, 4-Methylcatechol, 4-Methylcatechol, 4(methylnitrosamino)-1-(3-pyridyl)-butanone, 2-Naphthylamine, Nickel, Nitropropane, Nitrosodimethylamine, Nitrosoethymethylamine, Nitrosodiethylamine, Nitrosodi-n-propylamine, Nitrosodi-n-butylamine, Nitrosopyrrolidine, Nitrosopiperidine, Nitrosomorpholine, N'-Nitrosonomicotine, N'-Nitrosoanabasine, N'-Nitrosoanatabine, Polonium-210 (Radon), Urethane, or Vinyl Chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. From the above it will be clear that subjects "at risk of developing a cancer" are not all the subjects within a species of interest.

A subject "suspected of having a cancer" is one having one or more symptoms of a cancer. Symptoms of cancer are well-known to those of skill in the art and include, without limitation, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreas metastases, difficulty swallowing, and the like. Types of cancers can include, e.g., is lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer.

The disclosure provides an in vivo method of inhibiting histone deacetylation, which method includes the steps of: providing a subject having, or suspected of having, an inflammatory condition mediated by one or more cells expressing a KLF and/or MUC1; and delivering to the subject a compound that inhibits an HDAC. The method can include the step of identifying a subject as one having, suspected of having, or at risk of developing an inflammatory condition mediated by one or more inflammatory cells expressing MUC1 and/or a KLF. The method can also include the step of determining whether the one or more inflammatory cells of the inflammatory condition express MUC1 and/or a KLF. The method can also include the step of determining whether inhibition of an HDAC occurred. The HDAC can be HDAC1, HDAC2, HDAC3, or HDAC4. The compound can be butyrate, depsipeptide, phenylbutyrate, valproate, a trichostatin, suberoylanilide hydroxamic acid (SAHA), azelaic bishydroxamic acid (ABHA), scriptaid, pyroxamide, chlamydocin, apicidin, depudecin, MS-275, MGCD0103, PXD101, Daceca, Savisol, LBH589, PCI-24781, and ITF2357.

Also featured is an in vivo method of inhibiting an interaction between MUC1 and a KLF. The method includes the steps of: providing a subject having, or suspected of having, an inflammatory condition mediated by one or more cells expressing a KLF and/or MUC1, and delivering to the subject a compound that inhibits an interaction between MUC1 and a KLF. The method can include the step of identifying a subject as one having, suspected of having, or at risk of developing an inflammatory condition mediated by one or more inflammatory cells expressing MUC1 and/or a KLF. The method can also include the step of determining whether the one or more inflammatory cells of the inflammatory condition express MUC1 and/or a KLF. The method can also include the step of determining whether inhibition of an interaction between MUC1 and a KLF occurred.

Also featured is an in vivo method of inhibiting an interaction between MUC1 and a p53 promoter. The method includes the steps of: providing a subject having, or suspected of having, an inflammatory condition mediated by one or more cells expressing a KLF and/or MUC1, and delivering to the subject a compound that inhibits an interaction between MUC1 and a p53 promoter. The method can include the step of identifying a subject as one having, suspected of having, or at risk of developing an inflammatory condition mediated by one or more inflammatory cells expressing MUC1 and/or a KLF. The method can also include the step of determining whether the one or more inflammatory cells of the inflammatory condition express MUC1 and/or a KLF. The method can also include the step of determining whether inhibition of an interaction between MUC1 and a p53 promoter occurred. The interaction between MUC1 and a p53 promoter can be a direct physical interaction between MUC1 and the p53 promoter or can be indirect, e.g., mediated by one or more additional polypeptides such as a KLF (e.g., KLF4). The interaction between MUC1 and a p53 promoter can be a direct physical interaction between MUC1 and the p53 promoter or can be indirect, e.g., mediated by one or more additional polypeptides such as a KLF (e.g., KLF4).

Also featured is an in vivo method of inhibiting an interaction between a KLF (e.g., KLF4) and a p53 promoter. The method includes the steps of: providing a subject having, or suspected of having, an inflammatory condition mediated by one or more cells expressing a KLF and/or MUC1, and delivering to the subject a compound that inhibits an interaction between a KLF (e.g., KLF4) and a p53 promoter. The method can include the step of identifying a subject as one having, suspected of having, or at risk of developing an inflammatory condition mediated by one or more inflammatory cells expressing MUC1 and/or a KLF. The method can also include the step of determining whether the one or more inflammatory cells of the inflammatory condition express MUC1 and/or a KLF. The method can also include the step of determining whether inhibition of an interaction between a KLF and a p53 promoter occurred.

Also provided is an in vivo method of stimulating p53, which method includes the steps of: providing a subject having, or suspected of having, an inflammatory disorder mediated by one or more cells expressing a KLF and/or MUC1, and culturing the cell with a compound that inhibits an interaction between MUC1 and the p53 promoter. The method can include the step of identifying a subject as one having, suspected of having, or at risk of developing an inflammatory condition mediated by one or more inflammatory cells expressing MUC1 and/or a KLF. The method can also include the step of determining whether the one or more inflammatory cells of the inflammatory condition express MUC1 and/or a KLF. The method can also include the step of determining whether inhibition of an interaction between interaction between MUC1 and the p53 promoter occurred.

The disclosure also provides an in vivo method of increasing p53 activity. The method includes the steps of: providing a subject having, or suspected of having, an inflammatory disorder mediated by one or more cells expressing a KLF, delivering to the subject a compound that inhibits MUC1 and/or a KLF, and detecting whether an increase in p53 activity occurred. The method can include the step of identifying a subject as one having, suspected of having, or at risk of developing an inflammatory condition mediated by one or more inflammatory cells expressing MUC1 and/or a KLF. The method can also include the step of determining whether the one or more inflammatory cells of the inflammatory condition express MUC1 and/or a KLF. An increase in p53 activity can be an increase in p53 expression, e.g., p53 mRNA or p53 protein expression. An increase in p53 activity can be an increase in the level of expression of a p53-transactivated gene such as, but not limited to, p21, BAX, MDM2, GADD45, 14-3-3 sigma, FAS1, NOXA, PUMA, FASL, or Pirh2. The compound can inhibit the expression of MUC1 or a KLF. The compound can inhibit transcription of a MUC1 gene or a KLF gene. The compound can inhibit translation of a MUC1 mRNA or a KLF mRNA.

Also featured is an in vivo method of inhibiting an interaction between an HDAC and a p53 promoter. The method includes the steps of: providing a subject having, or suspected of having, an inflammatory condition mediated by one or more cells expressing MUC1, delivering to the subject a compound that inhibits an interaction between an HDAC and a p53 promoter, and optionally detecting whether an inhibition of an interaction between an HDAC and a p53 promoter has occurred. The method can also include the step of identifying a subject as one having an inflammatory condition mediated by one or more inflammatory cells expressing MUC1. The method can also include the step of determining whether one or more inflammatory cells mediating the inflammatory condition express MUC1. The compound can inhibit MUC1 or a KLF (e.g., KLF4). The compound can inhibit the transcription of a MUC1 coding sequence and/or inhibit the translation of a MUC1 mRNA. The compound can inhibit the transcription of a KLF coding sequence and/or inhibit the translation of a KLF mRNA. The HDAC can be HDAC1, HDAC2, HDAC3, or HDAC4. The interaction between an HDAC and a p53 promoter can be a direct, physical interaction between the HDAC and the p53 promoter or can be indirect, e.g., mediated by one or more additional polypeptides such as a KLF (e.g., KLF4) and/or MUC1.

Also provided is an in vivo method of inhibiting an interaction between an HDAC and a p53 promoter, which method includes the steps of: providing a subject having, or suspected of having, an inflammatory condition mediated by one or more cells expressing MUC1, delivering to the subject a compound that inhibits an interaction between an HDAC and a p53 promoter, and detecting whether an inhibition of an interaction between an HDAC and a p53 promoter has occurred. The method can also include the step of identifying a subject as one having an inflammatory condition mediated by one or more inflammatory cells expressing MUC1. The method can also include the step of determining whether one or more inflammatory cells mediating the inflammatory condition express MUC1. The compound can inhibit MUC1 or a KLF. The compound can inhibit the transcription of a MUC1 coding sequence and/or inhibit the translation of a MUC1 mRNA. The compound can inhibit the transcription of a KLF coding sequence and/or inhibit the translation of a KLF mRNA. The KLF can be KLF4. The HDAC can be HDAC1, HDAC2, HDAC3, or HDAC4. The interaction between an HDAC and a p53 promoter can be a direct, physical interaction between the HDAC and the p53 promoter or can be indirect, e.g., mediated by one or more additional polypeptides such as a KLF (e.g., KLF4) and/or MUC1.

Also featured is an in vivo method of inhibiting an interaction between MUC1 and a PE21 element. The method includes the steps of: providing a subject having, or suspected of having, an inflammatory condition mediated by one or more cells expressing a KLF and/or MUC1; and delivering to the subject a compound that inhibits an interaction between MUC1 and a PE21 element. The method can include the step of identifying a subject as one having, suspected of having, or at risk of developing an inflammatory condition mediated by one or more inflammatory cells expressing MUC1 and/or a KLF. The method can also include the step of determining whether the one or more inflammatory cells of the inflammatory condition express MUC1 and/or a KLF. The method can also include the step of determining whether inhibition of an interaction between MUC1 and a PE21 element occurred. The PE21 element can be a PE21 element from a p53 promoter. The p53 promoter can be a human p53 promoter (e.g., the p53 promoter sequence as depicted in SEQ ID NO:5). The PE21 element can have the SEQ ID NO:6.

Also featured is an in vivo method of inhibiting an interaction between a KLF and a PE21 element. The method includes the steps of: providing a subject having, or suspected of having, an inflammatory condition mediated by one or more cells expressing a KLF and/or MUC1, and delivering to the subject a compound that inhibits an interaction between a KLF and a PE21 element. The method can include the step of identifying a subject as one having, suspected of having, or at risk of developing an inflammatory condition mediated by one or more inflammatory cells expressing MUC1 and/or a KLF. The method can also include the step of determining whether the one or more inflammatory cells of the inflammatory condition express MUC1 and/or a KLF. The method can also include the step of determining whether inhibition of an interaction between a KLF and a PE21 element occurred. The PE21 element can be a PE21 element from a p53 promoter. The p53 promoter can be a human p53 promoter (e.g., the p53 promoter sequence as depicted in SEQ ID NO:5). The PE21 element can have the SEQ ID NO:6. The KLF can be KLF4.

A subject "at risk of developing an inflammatory condition" refers to a subject with a family history of one or more inflammatory conditions (e.g., a genetic predisposition to one or more inflammatory conditions) or one exposed to one or more inflammation-inducing conditions. For example, a subject can have been exposed to a viral or bacterial superantigen such as, but not limited to, staphylococcal enterotoxins (SEs), a *Streptococcus pyogenes* exotoxin (SPE), a *Staphylococcus aureus* toxic shock-syndrome toxin (TSST-1), a streptococcal mitogenic exotoxin (SME) and a streptococcal superantigen (SSA). From the above it will be clear that subjects "at risk of developing an inflammatory condition" are not all the subjects within a species of interest.

A subject "suspected of having an inflammatory condition" is one who presents with one or more symptoms of an inflammatory condition. Symptoms of inflammatory conditions are well known in the art and include, but are not limited to, redness, swelling (e.g., swollen joints), joints that are warm to the touch, joint pain, stiffness, loss of joint function, fever, chills, fatigue, loss of energy, headaches, loss of appetite, muscle stiffness, insomnia, itchiness, stuffy nose, sneezing, coughing, one or more neurologic symptoms such as dizziness, seizures, or pain. An "inflammatory condition," as used herein, refers to a process in which one or more substances (e.g., substances not naturally occurring in the subject), via the action of white blood cells (e.g., B cells, T cells, macrophages, monocytes, or dendritic cells) inappropriately trigger a pathological response, e.g., a pathological immune response. Accordingly, such cells involved in the inflammatory response are referred to as "inflammatory cells." The inappropriately triggered inflammatory response can be one where no foreign substance (e.g., an antigen, a virus, a bacterium, a fungus) is present in or on the subject. The inappropriately triggered response can be one where a self-component (e.g., a self-antigen) is targeted (e.g., an autoimmune disorder such as multiple sclerosis) by the inflammatory cells. The inappropriately triggered response can also be an response that is inappropriate in magnitude or duration, e.g., anaphylaxis. Thus, the inappropriately targeted response can be due to the presence of a microbial infection (e.g., viral, bacterial, or fungal). Types of inflammatory conditions (e.g., autoimmune diseasease) can include, but are not limited to, osteoarthritis, Rheumatoid arthritis (RA), spondyloarhropathies, POEMS syndrome, Crohn's disease, multicentric Castleman's disease, systemic lupus erythematosus (SLE), multiple sclerosis (MS), muscular dystrophy (MD), insulin-dependent diabetes mellitus (IDDM), dermatomyositis, polymyositis, inflammatory neuropathies such as Guillain Barre syndrome, vasculitis such as Wegener's granulomatosus, polyarteritis nodosa, polymyalgia rheumatica, temporal arteritis, Sjogren's syndrome, Bechet's disease, Churg-Strauss syndrome, or Takayasu's arteritis. Also included in inflammatory conditions are certain types of allergies such as rhinitis, sinusitis, urticaria, hives, angioedema, atopic dermatitis, food allergies (e.g., a nut allergy), drug allergies (e.g., penicillin), insect allergies (e.g., allergy to a bee sting), or mastocytosis. Inflammatory conditions can also include ulcerative colitis and asthma.

In any of the in vivo methods described herein, the KLF can be, or contain, KLF4 (e.g., the KLF4 as depicted in SEQ ID NO:7). In any of the in vivo methods described herein, the MUC1 can be, or contain, the MUC1-CD (such as the MUC1-CD as depicted in SEQ ID NO:2).

In any of the in vivo methods described herein, the subject can be a human.

In any of the in vivo methods described herein, the compound can be any of the compounds described herein. The compound can be a small molecule, an antibody, an antibody fragment, a polypeptide, or a peptidomimetic.

In some embodiments of any of the in vivo methods, the delivery can involve administering to a subject one or more of any of the compounds described herein, e.g., a compound of the invention.

In some embodiments of any of the in vivo methods, where the compound is a polypeptide, the methods can involve administering to the subject a nucleic acid comprising a nucleotide sequence encoding the polypeptide, the nucleotide sequence being operably linked to a transcriptional regulatory sequence. The nucleic acid can be in a recombinant cell transfected with the nucleic acid and secreting the polypeptide. The recombinant cell can be a transfected cell, or the progeny of a transfected cell, made by transfecting a cell derived from the subject. The cell that is transfected can be obtained directly from the subject or can be the progeny of a cell obtained from the subject.

"Polypeptide" and "protein" are used interchangeably and mean any peptide-linked chain of amino acids, regardless of length or post-translational modification.

The MUC1 and KLF (e.g., KLF4) "reagents" used in any of the methods of the invention can contain, or be, wild-type, full-length, mature proteins or fragments (e.g., functional fragments) of such proteins. The reagents can also be variants of full-length, mature, wild-type proteins or fragments of the proteins having additions, deletions, or substitutions. Reagents with substitutions will generally have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

Additions (addition variants) include full-length, wild-type, mature polypeptides or fragments with internal or terminal (C or N) irrelevant or heterologous amino acid sequences (i.e., sequences derived from other proteins or synthetic sequences not corresponding to any naturally occurring protein). The sequences can be, for example, an antigenic tag (e.g., FLAG, polyhistidine, hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). Heterologous sequences can be of varying length and in some cases can be a larger sequences than the full-length, wild-type mature polypeptides of fragments (functional fragments) thereof.

A "fragment," as used herein, refers to a segment of the polypeptide that is shorter than a full-length, immature polypeptide. A "functional fragment" of a polypeptide has at least 25% (e.g., at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the activity of the mature, polypeptide (see above). Fragments of a polypeptide include terminal as well internal deletion variants of a polypeptide. The polypeptides, fragments, or their variants can be of any species expressing relevant forms of the wild-type, human proteins, such as e.g., nematode, insect, plant, bird, reptile, or mammal (e.g., a mouse, rat, rabbit, hamster, gerbil, dog, cat, goat, pig, cow, horse, whale, or monkey). All that is required is that such variants have at least 25% (e.g., at least: 30%; 40%; 50%; 60%; 70%; 75%; 80%; 85%; 90%; 95%; 97%; 98%; 99%; 99.5%, or 100% or even greater) of the activity of the wild-type, full-length, mature protein.

In the case of MUC1, the relevant activity is the ability to bind (interact) with a KLF (e.g., KLF4). This activity is also sometimes referred to as KLF (e.g., KLF4)-binding activity.

In the case of a KLF (e.g., KLF4), the relevant activity is the ability to bind (interact) with MUC1 (or the MUC1-CD). This activity is thus sometimes referred to as MUC1-binding activity. In some embodiments, the relevant KLF (e.g., KLF4) activity is the ability to bind to the p53 promoter (e.g., the p53 promoter sequences depicted in SEQ ID NO:5 or SEQ ID NO:6). This KLF activity is sometimes referred to as p53-promoter binding activity.

It is understood that the term "KLF" refers to all forms (e.g., splice variants) of the proteins that bind to MUC1 (e.g., the MUC1-CD) and/or that bind to a p53 promoter. Methods of testing for an interaction between MUC1 and a KLF are known in the art and described in the Examples below. Similarly, the term "p53 promoter" refers to all forms (e.g., allelic variants) of the p53 promoter that bind to a KLF (e.g., KLF4) and/or to MUC1 (e.g., MUC1-CD).

As used herein, a "p53 promoter reagent" or "p53 promoter reagent" contains, or is, (a) a full-length, native p53 promoter nucleic acid sequence (e.g., the p53 promoter nucleic acid sequence depicted in SEQ ID NO:5), (b) a functional fragment of (a), or a homologous or complementary sequence variant of (a) or (b) (see below). As further described below, the p53 promoter can be from any species (e.g., nematode, insect, plant, bird, reptile, or mammal (e.g., a mouse, rat, rabbit, hamster, gerbil, dog, cat, goat, pig, cow, horse, whale, or monkey) that expresses a p53 protein from a p53 promoter sequence. "Functional fragments" of a p53 promoter or p53 promoter reagent, as used herein, refer to any p53 promoter fragments that substantially retain at least 25% (e.g., at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the relevant activity of a full-length promoter region (e.g., the human p53 promoter sequence depicted in SEQ ID NO:5) to be bound by (or to bind to) a KLF (e.g., KLF4). In some embodiments, the relevant activity of is the ability to bind to MUC1 (e.g., the MUC1-CD). This activity is referred to as "MUC1-binding activity." In some embodiments, the relevant activity is the ability to bind to a KLF (e.g., KLF4). This activity is thus referred to as KLF-binding activity. Suitable functional fragments of a p53 promoter can contain, or be, the PE21 element (e.g., SEQ ID NO:6) of the human p53 promoter (SEQ ID NO:5).

Variants of a p53 promoter can also have a sequence that is homologous, e.g., a sequence bearing at least about 70% (e.g., at least about 75%, at least about 80%, at least about 85%, at least about 90%, at least about 95%, or at least about 99%) homology to a native p53 promoter sequence. A "native" nucleic acid sequence is one that is derived from nature (e.g., a human p53 promoter sequence). Such native sequences can be isolated from nature or can be produced by recombinant or synthetic methods. Thus a native sequence nucleic acid can have the nucleic acid sequence of naturally occurring human nucleic acid sequences, monkey nucleic acid sequences, murine nucleic acid sequences, or any other species that expresses a p53 polypeptide from a p53 promoter. As used herein, a "homologous" or "homologous nucleic acid sequence" or similar term, refers to sequences characterized by homology at the nucleotide level of at least a specified percentage and is used interchangeably with sequence identity. As described above, homologous nucleic acid sequences, or homologous p53 promoter reagent sequences, can include sequences from any species that expresses MUC1 from a p53 promoter.

Percent homology or identity can be determined by, for example, the Gap program (Wisconsin Sequence Analysis Package, Version 8 for UNIX, Genetics Computer Group, University Research Park, Madison, Wis.), using default settings, which uses the algorithm of Smith and Waterman ((1981) Adv. Appl. Math. 2: 482-489). In some embodiments, homology between a probe and target (see below) is between about 50% to about 60%. In some embodiments, homology between a probe and target nucleic acid is between about 55% to 65%, between about 65% to 75%, between about 70% to 80%, between about 75% and 85%, between about 80% and 90%, between about 85% and 95%, or between about 90% and 100%.

The term "probe," as used herein, refers to nucleic acid sequences of variable length. In some embodiments, probes comprise at least 10 and as many as 6,000 nucleotides. In some embodiments probes comprise at least 12, at lease 14, at least 16, at least 18, at least 20, at least 25, at least 50 or at least 75 or 100 contiguous nucleotides. Longer length probes are usually obtained from natural or recombinant sources (as opposed to direct, chemical synthesis), are highly specific to the target sequence, and are much slower to hybridize to the target than longer oligomers. Probes can be single or double stranded nucleic acid molecules.

In some embodiments, the p53 promoter reagent can have a sequence comprising one or both strands with partial complementary (e.g., at least 50%, at least 60%, at least 70%, at least 80%, at least 90%, at least 95%, at least 96%, at least 97%, at least 98%, at least 99% complementary) to a region, portion, domain, or segment of the human p53 promoter (e.g., the PE21 region depicted in SEQ ID NO:6). In some embodiments, the p53 promoter reagent can have a sequence comprising one or both strands with full complementary (i.e., 100% complementary) to a region, portion, domain, or segment of the human p53 promoter (e.g., the PE21 region as depicted in SEQ ID NO:6). Sequence "complementarity" refers to the chemical affinity between specific nitrogenous bases as a result of their hydrogen bonding properties (i.e., the property of two nucleic acid chains having base sequences such that an antiparallel duplex can form where the adenines and uracils (or thymine, in the case of DNA or modified RNA) are apposed to each other, and the guanines and cytosines are apposed to each other). Fully complementary sequences, thus, would be two sequences that have complete one-to-one correspondence (i.e., adenine to uracil and guanine to cytosine) of the base sequences when the nucleotide sequences form an antiparallel duplex.

As used herein, a "promoter" refers to a DNA sequence that enables a gene to be transcribed. The promoter is recognized by RNA polymerase, which then initiates transcription. Thus, a promoter contains a DNA sequence that is either bound directly by, or is involved in the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. The enhancer, while typically at the 5' end of a coding region, can also be within an intronic region of a gene, or 3' to the coding region.

As used herein, "operably linked" means incorporated into a genetic construct so that expression control sequences effectively control expression of a coding sequence of interest.

Unless otherwise defined, all technical and scientific terms used herein have the same meaning as commonly understood by one of ordinary skill in the art to which this invention pertains. Preferred methods and materials are describe below, although methods and materials similar or equivalent to those described herein can be used in the practice or testing of the present invention. All publications, patent applications, patents, and other references mentioned herein are incorporated by reference in their entirety. The materials, methods, and examples disclosed herein are illustrative only and not intended to be limiting.

Other features and advantages of the invention, e.g., methods for identifying a compound that inhibits the binding of MUC1 to a KLF, will be apparent from the following description, from the drawings and from the claims.

BRIEF DESCRIPTION OF THE DRAWINGS

FIG. 3D is a pair of photographs of (a) an autoradiogram and (b) a Coomassie blue stained polyacrylamide gel. GST, GST-MUC1-CD(1-72), GST-MUC1-CD(47-72), or GST-MUC1-CD(1-46) were bound to glutathione-conjugated agarose beads and incubated with [$^{35}$S]-labeled KLF4 protein. The beads were washed to remove unbound KLF4 protein. The remaining adsorbates were analyzed by SDS-PAGE and autoradiography (top photograph). Input KLF4 protein is shown in the first lane of the top photograph. Input of the GST and GST-MUC1-CD fusion proteins was assessed by Coomassie blue staining. The molecular weights of the proteins (expressed in kilodaltons (kDa)) are indicated at the left of each of the photographs.

FIG. 3E is a series of photographs of agarose gels depicting the results of ChIP experiments. Soluble chromatin was prepared from MCF-7 and ZR-75-1 cells and subjected to immunoprecipitation using an antibody specific for MUC1-C ("MUC1-C") or a control IgG ("IgG"). DNA present in the immunoprecipitates was amplified by PCR using primers that cover a control region (CR; −6020 to −5940) or the region that contains the PE21 element (PE21; −118 to −54) in the p53 gene promoter. PCR products were resolved using agarose gels, stained with ethidium bromide, and visualized using UV light.

FIG. 9A is a depiction of an exemplary amino acid sequence for a human KLF4 polypeptide (SEQ ID NO:7).

FIG. 9B is a depiction of an exemplary nucleotide sequence for a human p53 promoter sequence (SEQ ID NO:5). An exemplary nucleotide sequence for a PE21 element (SEQ ID NO:6) of the human p53 promoter (SEQ ID NO:5) is underlined.

FIG. 9C is a depiction of an exemplary amino acid sequence for a human MUC1 protein (SEQ ID NO:1).

FIG. 9D is a depiction of the domain structure of the human MUC1 cytoplasmic domain (MUC1-CD; SEQ ID NO:2). The numbers above the diagram indicate the amino acid positions (1-72). Two smaller fragments of MUC1-CD are indicated below the MUC1-CD sequence. These fragments correspond to amino acids 1-40 (SEQ ID NO:3) and 46-72 (SEQ ID NO:4) of the MUC1-CD.

DESCRIPTION OF THE ILLUSTRATIVE EMBODIMENTS

Figure 1A:
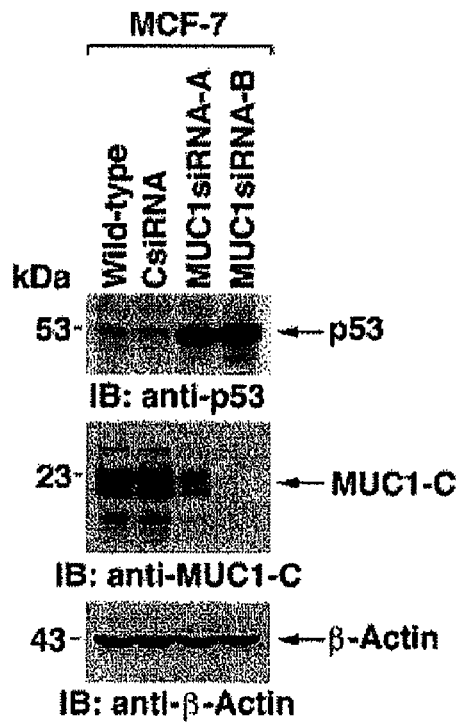
FIGS. 1A and 1B are a series of photographs of immunoblots depicting the regulation of p53 protein levels by MUC1. MCF-7 cells (FIG. 1A) or ZR-75-1 cells (FIG. 1B) were treated with a control (non-specific) siRNA (CsiRNA) or siRNAs specific for MUC1 (MUC1siRNA-A and MUC1siRNA-B). Whole cell lysates from the indicated cells were subjected to sodium dodecyl sulfate-polyacrylamide gel electrophoresis (SDS-PAGE) and subsequently immunoblotted (IB) using antibodies specific for p53, MUC1-C and anti-β-actin as indicated below each of the photographs. The molecular weights of each of the immunoblotted proteins are given in units of kDa (kilodaltons) and indicated at the left of the photographs

A. Methods of Screening for Inhibitory Compounds

The MUC1-KLF Interaction. The present invention provides in vitro methods (e.g., "screening methods") for identifying compounds (e.g., small molecules or macromolecules) that inhibit binding of a KLF (e.g., KLF4, or a functional fragment of a KLF) to MUC1, and in particular, the MUC1-CD.

These methods can be performed using: (a) isolated MUC1 reagents and one or more isolated KLF reagents; or (b) cells expressing a MUC1 reagent and one or more KLF reagents.

The term "isolated" as applied to any of the polypeptide reagents described herein refers to a polypeptide, or a peptide fragment thereof, which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue (e.g., breast cancer or colon cancer tissue), or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a reagent is at least 80%, more preferably at least 90%, and most preferably at least 99%, by dry weight, the reagent. Since a polypeptide that is chemically synthesized is, by its nature, separated from the components that naturally accompany it, a synthetic polypeptide reagent is "isolated."

An isolated polypeptide reagent can be obtained, for example, by extraction from a natural source (e.g., from tissues); by expression of a recombinant nucleic acid encoding the polypeptide; or by chemical synthesis. A polypeptide reagent that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

Prior to testing, any of the reagents described herein can undergo modification, e.g., phosphorylation or glycosylation, by methods known in the art.

In methods of screening for compounds that inhibit binding of an isolated MUC1 reagent to an isolated KLF reagent, a MUC1 reagent is contacted with a KLF reagent in the presence of one or more concentrations of a test compound and binding between the two reagents in the presence and absence of the test compound is detected, tested for, and/or measured. In such assays neither of the reagents need be detectably labeled. For example, by exploiting the phenomenon of surface plasmon resonance, the MUC1 reagent can be bound to a suitable solid substrate and a KLF reagent exposed to the substrate-bound MUC1 reagent in the presence and absence of the compound of interest. Binding of the KLF reagent to the MUC1 reagent on the solid substrate results in a change in the intensity of surface plasmon resonance that can be detected qualitatively or quantitatively by an appropriate instrument, e.g., a Biacore apparatus (Biacore International AB, Rapsgatan, Sweden). It will be appreciated that the experiment can be performed in reverse, i.e., with the KLF reagent bound to the solid substrate and the MUC1 reagent added to it in the presence of the test compound.

Moreover, assays to test for inhibition (or in some cases enhancement) of binding to MUC1 can involve the use, for example, of: (a) a single MUC1-specific "detection" antibody that is detectably labeled; (b) an unlabeled MUC1-specific antibody and a detectably labeled secondary antibody; or (c) a biotinylated MUC1-specific antibody and detectably labeled avidin. In addition, combinations of these approaches (including "multi-layer" assays) familiar to those in the art can be used to enhance the sensitivity of assays. In these assays, the KLF (e.g., KLF4) reagent can be immobilized on a solid substrate such as a nylon or nitrocellulose membrane by, for example, "spotting" an aliquot of a sample containing the reagent onto a membrane or by blotting onto a membrane an electrophoretic gel on which the sample or an aliquot of the sample has been subjected to electrophoretic separation. Alternatively, the KLF reagent can be bound to a plastic substrate (e.g., the plastic bottom of an ELISA (enzyme-linked immunosorbent assay) plate well) using methods known in the art. The substrate-bound reagent is then exposed to the MUC1 reagent in the presence and absence of the test compound. After incubating the resulting mixture for a period of time and at temperature optimized for the system of interest, the presence and/or amount of MUC1 reagent bound to the KLF test on the solid substrate is then assayed using a detection antibody that binds to the MUC1 reagent and, where required, appropriate detectably labeled secondary antibodies or avidin. It will be appreciated that instead of binding the KLF reagent to the solid substrate, the MUC1 reagent can be bound to it. In this case binding of the KLF reagent to the substrate-bound MUC1 is tested by obvious adaptations of the method described above for substrate-bound KLF reagent.

The invention also features "sandwich" assays. In these sandwich assays, instead of immobilizing reagents on solid substrates by the methods described above, an appropriate reagent can be immobilized on the solid substrate by, prior to exposing the solid substrate to the reagent, conjugating a "capture" reagent-specific antibody (polyclonal or mAb) to the solid substrate by any of a variety of methods known in the art. The reagent is then bound to the solid substrate by virtue of its binding to the capture antibody conjugated to the solid substrate. The procedure is carried out in essentially the same manner described above for methods in which the appropriate reagent is bound to the solid substrate by techniques not involving the use of a capture antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either: (a) a mAb that binds to an epitope that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the use of a capture and a detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles.

Methods of detecting and/or for quantifying a detectable label depend on the nature of the label and are known in the art. Appropriate labels include, without limitation, radionuclides (e.g., $^{125}$I, $^{131}$I, $^{35}$S, $^{3}$H, $^{32}$P, or $^{14}$C), fluorescent reagents (e.g., fluorescein, rhodamine, or phycoerythrin), luminescent reagents (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, colorimeters, fluorometers, luminometers, and densitometers.

Candidate compounds can also be tested for their ability to inhibit binding of MUC1 to a KLF (e.g., KLF4) in cells. The cells can either naturally express an appropriate MUC1 reagent and/or a KLF reagent of interest (i.e., the cells encode an endogenous MUC1 and/or KLF gene which can be expressed to yield a MUC1 and/or KLF polypeptide or their functional fragments) or they can recombinantly express either or both reagents. The cells can be normal or malignant and of any histological type, e.g., without limitation, epithelial cells, fibroblasts, lymphoid cells, macrophages/monocytes, granulocytes, keratinocytes, neuronal cells, or muscle cells. Suitable cell lines include those recited in the examples, e.g., breast cancer or colon cancer cell lines. The test compound can be added to the solution (e.g., culture medium) containing the cells or, where the compound is a protein, the cells can recombinantly express it. The cells can optionally also be exposed to a stimulus of interest (e.g., IL-6, heat shock, or a heregulin (HRG)) prior to or after exposure of the cells to the compound. Following incubation of cells expressing the reagents of interest in the absence or presence of a compound (optionally at various concentrations), physical association between the reagents can be determined microscopically using appropriately labeled antibodies specific for both reagents, e.g., by confocal microscopy. Alternatively, the cells can be lysed under non-dissociating conditions and the lysates tested for the presence of physically associated reagents. Such methods include adaptions of those described using isolated reagents. For example, an antibody specific for one of the two reagents (reagent 1) can be bound to a solid substrate (e.g., the bottom and sides of the well of a microtiter plate or a nylon membrane). After washing away unbound antibody, the solid substrate with bound antibody is contacted with the cell lysate. Any reagent 1 in the lysate, bound or not bound to the second reagent (reagent 2), will bind to the antibody specific for reagent 1 on the solid substrate. After washing away unbound lysate components, the presence of reagent 2 (bound via reagent 1 and the antibody specific for reagent 1 to the solid substrate) is tested for using a detectably labeled antibody (see above) specific for reagent 2. Alternatively, reagent 1 can be immunoprecipitated with an antibody specific for reagent 1 and the immunoprecipitated material can be subjected to electrophoretic separation (e.g., by polyacrylamide gel electrophoresis performed under non-dissociating conditions). The electrophoretic gel can then be blotted onto a membrane (e.g., a nylon or a nitrocellulose membrane) and any reagent 2 on the membrane detected and/or measured with a detectably labeled antibody (see above) specific for reagent 2 by any of the above-described methods. It is understood that in the above-described assays, reagent 1 can be either the MUC1 reagent or the KLF reagent or vice versa. The test compounds can bind to one or both of the MUC1 and KLF reagents.

Exemplary MUC1 reagents for use in the methods described above can include MUC1 reagents that contain the MUC1-cytoplasmic domain (CD), e.g., the human MUC1-CD depicted by SEQ ID NO:2 (or a functional fragment of the MUC1-CD, e.g., amino acids 1-46 of the MUC1 as depicted in SEQ ID NO:3).

Inhibition of KLF-p53 Promoter Interactions. The present invention provides in vitro methods (e.g., "screening methods") for identifying compounds (e.g., small molecules or macromolecules) that inhibit binding of a KLF (e.g., KLF4, or a functional fragment of a KLF) to a p53 promoter (e.g., a PE21 element of a p53 promoter such as the PE21 element depicted in SEQ ID NO:6).

These methods can be performed using: (a) isolated KLF reagents and one or more isolated p53 promoter reagents; or (b) cells expressing a KLF reagent and one or more p53 promoter reagents. The methods can also be performed in cell-free or cell-based systems using the aforementioned components and one or more isolated MUC1 reagents. For example, MUC1 can serve to enhance the interaction between a KLF and the p53 promoter. Thus, in tests to identify a compound capable of inhibiting the interaction between a KLF (e.g., KLF4 or functional fragment of any of these KLF polypeptides) and a p53 promoter, a MUC1 reagent (at one or more concentrations) can be included. The MUC1 reagent can be contacted with the KLF and p53 promoter reagents simultaneously, or the MUC1 reagent can be contacted first with the KLF reagent (e.g., to form a molecular complex containing both the KLF and MUC1) and then contacted with the p53 promoter reagent. It is understood that the invention embraces any other possible combination or order of addition that would be appropriate for a given test (e.g., contacting KLF and p53 promoter reagents first, followed by contacting with the MUC1 reagent). Exemplary MUC1 reagents to be used in such methods can include the MUC1-CD. Exemplary p53 promoter reagents include the human p53 promoter (e.g., the human p53 promoter region in SEQ ID NO:5) or a PE21 element of a p53 promoter (e.g., the PE21 element SEQ ID NO:6) of the human p53 promoter).

In methods of screening for compounds that inhibit binding of an isolated KLF reagent to an isolated p53 promoter reagent, a KLF reagent is contacted with a p53 promoter reagent in the presence of one or more concentrations of a test compound and binding between the two reagents in the presence and absence of the test compound is detected, tested for, and/or measured. As discussed above, the KLF reagent and p53 promoter reagent can be also be contacted in the presence of a MUC1 reagent. In such assays neither of the reagents need be detectably labeled. For example, by exploiting the phenomenon of surface plasmon resonance, the p53 promoter reagent can be bound to a suitable solid substrate (e.g., agarose or sepharose beads, plastic screening assay plate or well, or other solid-phase substrates such as nitrocellulose) and a KLF reagent exposed to the substrate-bound p53 promoter reagent in the presence and absence of the compound of interest. Binding of the KLF reagent to the p53 promoter reagent on the solid substrate results in a change in the intensity of surface plasmon resonance that can be detected qualitatively or quantitatively by an appropriate instrument, e.g., a Biacore apparatus (see above). It will be appreciated that the experiment can be performed in reverse, i.e., with the KLF reagent bound to the solid substrate and the p53 promoter reagent added to it in the presence of the test compound.

Moreover, assays to test for inhibition (or in some cases enhancement) of KLF binding to a p53 promoter can involve the use, for example, of: (a) a single KLF-specific "detection" antibody that is detectably labeled; (b) an unlabeled KLF-specific antibody and a detectably labeled secondary antibody; or (c) a biotinylated KLF-specific antibody and detectably labeled avidin. In addition, combinations of these approaches (including "multi-layer" assays) familiar to those in the art can be used to enhance the sensitivity of assays. In these assays, the p53 promoter reagent (e.g., the PE21 element of a p53 promoter such as the PE21 element (SEQ ID NO:6) of the human p53 promoter) can be immobilized on a solid substrate such as a nylon or nitrocellulose membrane by, for example, "spotting" an aliquot of a sample containing the reagent onto a membrane or by blotting onto a membrane an electrophoretic gel on which the sample or an aliquot of the sample has been subjected to electrophoretic separation. Alternatively, the p53 promoter reagent can be bound to a plastic substrate (e.g., the plastic surface of an assay plate well such as a Costar 96-well assay plate (Corning Life Sciences Acton, Mass.)) using methods known in the art. The substrate-bound reagent is then exposed to the KLF reagent in the presence and absence of the test compound (also optionally with a MUC1 reagent). After incubating the resulting mixture for a period of time and at temperature optimized for the system of interest, the presence and/or amount of the KLF reagent bound to the p53 promoter test on the solid substrate is then assayed using a detection antibody that binds to the KLF reagent and, where required, appropriate detectably labeled secondary antibodies or avidin.

It will be appreciated that instead of binding the p53 promoter reagent to the solid substrate, the KLF (e.g., KLF4) reagent can be bound to the solid-phase substrate. In this case, binding of the p53 promoter reagent to the substrate-bound KLF (e.g., KLF4) reagent is tested by obvious variations of the method described above for substrate-bound p53 promoter reagent. The p53 promoter reagent can itself be detectably labeled, for example, with a fluorescent, luminescent, or radioactive label such as $^{32}P$, $^{33}P$, $^{35}S$, $^{125}I$, or $^{3}H$. Suitable methods for labeling (e.g., end-labeling) nucleic acids with radioactive labels are well known in the art and are described in, e.g., Sambrook et al. (1989) *Molecular Cloning: A Laboratory Manual*. Second edition, Cold Spring Harbor Laboratory Press, Cold Spring Harbor, N.Y. Suitable methods and devices for detecting/measuring the detectable label are set forth above. By this approach, an observed reduction in the amount of detectable label associated with the substrate-bound KLF reagent in the presence of a compound as compared to in the absence of the compound indicates that the compound inhibits the interaction between the KLF and the p53 promoter.

Gel-shift assays are also useful in detecting interactions between DNA-binding proteins and nucleic acids. Thus, such assays can be useful to determine whether a compound inhibits the interaction between KLF and a p53 promoter. These assays can involve, for example, incubating a detectably-labeled p53 promoter reagent and the KLF reagent in the presence and absence of a candidate compound for a predetermined period of time (e.g., at least 15 minutes, at least 20 minutes, at least 25 minutes, at least 30 minutes, at least 35 minutes, at least 40 minutes, at least 45 minutes, at least 60 minutes, at least 60 minutes or more) and then subjecting the molecular complex to a cross-linking agent (e.g., by treatment with DMS and/or formaldehyde). Cross-linked DNA-protein complexes (e.g., complexes comprising the P53 promoter reagent and the KLF reagent) are then subjected to SDS-PAGE to resolve complexes by size. Protein-DNA complexes are generally retarded in the gel whereas unbound nucleic acid migrates more quickly in the gel, and thus can be differentially detected based on location. These methods are well known in the art and are described in, e.g., Giardana et al. (1995) Mol. Cell. Biol. 15(5): 2737-2744; Bevilacqua et al. (1997) Nucleic Acids Res. 25(7): 1333-1338; and Alfieri et al. (1996) Biochem. J. 319: 601-606. A lower amount of DNA-protein complexes (complexes comprising a KLF reagent and a p53 promoter reagent) occurring in the presence of a candidate compound versus without the candidate compound indicates that the candidate compound is a compound that inhibits the interaction between KLF and the p53 promoter. As above, the nucleic acid (e.g., the p53 promoter reagent) can be detectably labeled (e.g., radionuclide, fluorescent or luminescent marker) or in some instances, the proteinaceous reagent (e.g., the KLF reagent) can be detectably labeled or itself otherwise detected by western blotting for the KLF protein (e.g., using an antibody specific for KLF protein).

Inhibition of MUC1-p53 Promoter Interactions. The present invention also provides in vitro methods (e.g., "screening methods") for identifying compounds (e.g., small molecules) that inhibit binding of MUC1 to a p53 promoter (e.g., the PE21 element of a p53 promoter).

These methods can be performed using: (a) isolated MUC1 reagents and one or more isolated p53 promoter reagents; or (b) cells expressing a MUC1 reagent and one or more p53 promoter reagents. The methods can also be performed in cell-free or cell-based systems using the aforementioned components and one or more isolated KLF (e.g., KLF4) reagents. For example, where the KLF can serve to enhance the interaction between MUC1 and the p53 promoter, it can be useful to identify a compound capable of inhibiting the interaction between an MUC1 reagent and a p53 promoter reagent in the presence of a KLF reagent such as one having the sequence depicted in SEQ ID NO:7, or a functional fragment of that sequence. The KLF reagent can be contacted with the MUC1 reagent and p53 promoter reagent simultaneously, or the KLF reagent can be contacted first with the MUC1 reagent (e.g., to form a molecular complex containing both the KLF and MUC1) and then contacted with the p53 promoter reagent. While not limited by any particular theory or mechanism, where cooperativity exists, or is likely to or suspected to exist, between the binding of more than one different transcription factors to p53 promoter elements, the additional transcription factors can also be contacted with the reagents of the assay in the presence and absence of a candidate compound. It is understood that the invention embraces any other possible combination or order of addition that would be appropriate for a given test (e.g., see above under "Inhibition of KLF-p53 Promoter Interactions"). Exemplary MUC1 reagents to be used in such methods include the MUC1-CD or a functional fragment thereof (e.g., any of MUC1-CD reagents described herein). Exemplary p53 promoter reagents include the PE21 element of a p53 promoter (e.g., the PE21 element of the human p53 promoter as depicted in SEQ ID NO:6) or any of the exemplary p53 promoter reagents described above.

Suitable methods of screening for compounds that inhibit an interaction between MUC1 and the p53 promoter can include any of the methods described above under "Inhibition of KLF-p53 promoter Interactions."

B. Methods of Designing and Producing Inhibitory Compounds

Compounds that Inhibit MUC1-KLF Interaction. The invention also relates to using MUC1 reagents and/or KLF (e.g., KLF4) reagents to predict or design compounds that can physically interact with MUC1 and/or a KLF (e.g., KLF4) and potentially thereby inhibit the interaction between these two polypeptides. Such compounds would be useful to inhibit the ability of MUC1 to promote cell survival (e.g., through inhibition of MUC1 effects on KLF activity). One of skill in the art would know how to use standard molecular modeling or other techniques to identify small molecules that would bind to "appropriate sites" on MUC1 and/or a KLF (e.g., KLF4). One such example is provided in Broughton (1997) Curr. Opin. Chem. Biol. 1, 392-398. Generally, an "appropriate site" on a MUC1 or a KLF (e.g., KLF4) is a site directly involved in the physical interaction between the two molecule types. However, an "appropriate site" can also be an allosteric site, i.e., a region of the molecule not directly involved in a physical interaction with another molecule (and possibly even remote from such a "physical interaction" site) but to which binding of a compound results (e.g., by the induction of a conformational change in the molecule) in inhibition of the binding of the molecule to another molecule.

By "molecular modeling" is meant quantitative and/or qualitative analysis of the structure and models, interactive computer graphic models, modified molecular mechanics models, distance geometry and other structure-based constraint models. Molecular modeling typically is performed using a computer and may be further optimized using known methods.

Methods of designing compounds that bind specifically (e.g., with high affinity) to the region generating an atomic model. Computer programs that use X-ray crystallography data are particularly useful for designing such compounds. Programs such as RasMol, for example, can be used to generate a three dimensional model of, e.g., the region of MUC1 that interacts with a KLF (e.g., KLF4) or the region of a KLF (e.g., KLF4) that binds to MUC1 and/or determine the structures involved in MUC1-KLF binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures.

Compounds can be designed using, for example, computer hardware or software, or a combination of both. However, designing is preferably implemented in one or more computer programs executing on one or more programmable computers, each containing a processor and at least one input device. The computer(s) preferably also contain(s) a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object-oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

For example, the computer-requiring steps in a method of designing a compound can involve:

(a) inputting into an input device, e.g., through a keyboard, a diskette, or a tape, data (e.g. atomic coordinates) that define the three-dimensional (3-D) structure of a first molecule (e.g., MUC1 or a part of MUC1 such as the MUC1-CD) that is known, or predicted, to bind to a second molecule (e.g., a KLF (e.g., KLF1) or a part thereof) or a molecular complex (e.g., MUC1, or a part thereof, predicted to bind to a KLF (e.g., KLF4), or a part thereof, or MUC1 bound to a macromolecular KLF complex), e.g., a region of MUC1 (e.g., the cytoplasmic domain of MUC1) that interacts with a KLF, the region of a KLF that binds to MUC1, or all or a part (e.g., the cytoplasmic domain) of MUC1 bound to all or a part of a KLF (e.g., KLF4); and (b) determining, using a processor, the 3-D structure (e.g., an atomic model) of: (i) the site on the first molecule involved, or predicted to be involved, in binding to the second molecule; or (ii) one or more sites on the molecular components of molecular complex of interaction between molecular components of the molecular complex.

From the information obtained in this way, one skilled in the art will be able to design and make inhibitory compounds (e.g., peptides, non-peptide small molecules, aptamers (e.g., nucleic acid aptamers) with the appropriate 3-D structure (see "Methods of Making Inhibitory Compounds and Proteins Useful for the Invention" below).

Moreover, if computer-usable 3-D data (e.g., x-ray crystallographic or nuclear magnetic resonance (NMR) data) for a candidate compound are available, the following computer-based steps can be performed in conjunction with computer-based steps (a) and (b) described above:

(c) inputting into an input device, e.g., through a keyboard, a diskette, or a tape, data (e.g. atomic coordinates) that define the three-dimensional (3-D) structure of a candidate compound;

(d) determining, using a processor, the 3-D structure (e.g., an atomic model) of the candidate compound; (e) determining, using the processor, whether the candidate compound binds to the site on the first molecule or the one or more sites on the molecular components of the molecular complex; and (f) identifying the candidate compound as compound that inhibits the interaction between the first and second molecule or the between the molecular components of the molecular complex.

The method can involve the additional step of outputting to an output device a model of the 3-D structure of the compound. In addition, the 3-D data of candidate compounds can be compared to a computer database of, for example, 3-D structures (e.g., of MUC1, the cytoplasmic domain of MUC1, KLF (e.g., KLF4), or a MUC1-binding fragment of a KLF) stored in a data storage system.

Compounds useful for the invention also may be interactively designed from structural information of the compounds described herein using other structure-based design/modeling techniques (see, e.g., Jackson (1997) *Seminars in Oncology* 24: L164-172; and Jones et al. (1996) *J. Med. Chem.* 39: 904-917). Compounds and polypeptides of the invention also can be identified by, for example, identifying candidate compounds by computer modeling as fitting spatially and preferentially (i.e., with high affinity) into the appropriate acceptor sites on MUC1 or a KLF (e.g., KLF4).

Candidate compounds identified as described above can then be tested in standard cellular or cell-free binding or binding inhibition assays familiar to those skilled in the art. Exemplary assays are described herein.

A candidate compound whose presence requires at least 2-fold (e.g., 4-fold, 6-fold, 10-fold, 100-fold, 1000-fold, 10,000-fold, or 100,000-fold) more of a given MUC1 reagent to achieve a defined arbitrary level of binding to a fixed amount of a KLF reagent than is achieved in the absence of the compound can be useful for inhibiting the interaction between MUC1 and the relevant KLF, and thus can be useful as a cancer therapeutic or prophylactic agent. Alternatively, a candidate compound whose presence requires at least 2-fold (e.g., 2-fold, 4-fold, 6-fold, 10-fold, 100-fold, 1000-fold, 10,000-fold, or 100,000-fold) more of a given KLF reagent to achieve a defined arbitrary level of binding to a fixed amount of a MUC1 reagent than is achieved in the absence of the compound can be useful for inhibiting the interaction between MUC1 and the relevant KLF, and thus can be useful as a cancer therapeutic or prophylactic agent.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention [e.g., Cohen et al. (1990) J. Med. Chem. 33: 883-894; Navia et al (1992) Current Opinions in Structural Biology, 2, pp. 202-210, the disclosures of which are incorporated herein by reference in its entirety]. All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

Compounds that Inhibit KLF-p53 Promoter Interaction. The invention also relates to using KLF (e.g., KLF4) reagents and/or p53 promoter reagents to predict or design compounds that can interact with a KLF (e.g., KLF4) and/or a p53 promoter (e.g., the PE21 element of a p53 promoter) and potentially thereby inhibit the interaction between these two polypeptides. The methods can also involve using additional reagents such as MUC1 reagents to predict or design compounds that interact with a KLF or p53 promoter. Such compounds would be useful to inhibit the ability of MUC1 to promote cell survival (e.g., through inhibition MUC1/KLF4- mediated suppression of p53 expression). One of skill in the art would know how to use standard molecular modeling or other techniques (e.g., obvious adaptations of methods described above) to identify small molecules that would bind to "appropriate sites" on KLF (e.g., KLF4) or a p53 promoter (e.g., an PE21 element of a p53 promoter). Generally, an "appropriate site" on a KLF (e.g., KLF4) and/or a p53 promoter is a site directly involved in the physical interaction between the two molecule types. As pointed out above, an "appropriate site" can also be an allosteric site, i.e., a region of the molecule not directly involved in a physical interaction with another molecule.

Methods of designing compounds that bind specifically (e.g., with high affinity) to the region of a KLF (e.g., KLF4) that interacts with a P53 promoter (i.e., DNA-binding domain of a KLF) or the region of a p53 promoter (e.g., the PE21 element of a p53 promoter) that is bound by a KLF (e.g., KLF4) typically are also computer-based, and can involve the use of a computer as described above. Compounds can be designed using, for example, computer hardware or software, or a combination of both, as described above.

Compounds useful for the invention also can be interactively designed from structural information of the compounds described herein using other structure-based design/modeling techniques as above. For example, compounds and polypeptides of the invention also can be identified by identifying candidate compounds by computer modeling as fitting spatially and preferentially (i.e., with high affinity) into the appropriate acceptor sites on a KLF (e.g., KLF4) or a p53 promoter (e.g., an PE21 element of a p53 promoter).

Candidate compounds identified as described above can then be tested in standard cellular or cell-free binding or binding inhibition assays familiar to those skilled in the art as described above.

Compounds that Inhibit MUC1-p53 Promoter Interaction. The invention also relates to using MUC1 (e.g., MUC1-CD) reagents and/or p53 promoter reagents to predict or design compounds that can interact with MUC1 (e.g., MUC1-CD) and/or a p53 promoter (e.g., the PE21 element of a p53 promoter) and potentially thereby inhibit the interaction between these two polypeptides. The methods can also involve using additional reagents such as KLF reagents (see above) to predict or design compounds that interact with MUC1 or a p53 promoter. Such compounds would be useful to inhibit the ability of MUC1 to promote cell survival (e.g., through inhibition MUC1/KLF4-mediated suppression of p53 expression). Standard molecular modeling (e.g., computer-based methods) and other techniques (e.g., obvious adaptations of methods described above) to identify small molecules that would bind to "appropriate sites" on MUC1 (e.g., MUC1-CD) or a p53 promoter (e.g., an PE21 element of a p53 promoter) are described above.

Compounds useful for the invention also can be interactively designed from structural information of the compounds described herein using other structure-based design/modeling techniques, and tested in standard cellular or cell-free assays as described above.

X-Ray Crystallography

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds it's solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules [Weber (1991) Advances in Protein Chemistry, 41: 1-36]. In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5-7.5. Other additives can include 0.1 M HEPES, 2-4% butanol, 0.1 M or 20 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique [McPherson (1976) J. Biol. Chem., 251: 6300-6306], an initial polypeptide mixture is created by adding a precipitant to a concentrated polypeptide solution. The concentrations of the polypeptide and precipitants are such that, in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to −220° C. to −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. application Ser. No. 10/486,278, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy

While x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa [Wider (2000) BioTechniques, 29: 1278-1294].

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, J. Cavanagh et al., Academic Press, San Diego, 1996; Gronenbom et al. (1990) Anal. Chem. 62(1): 2-15; and Wider (2000), supra., the disclosures of all of which are incorporated herein by reference in their entirety Any available method can be used to construct a 3-D model of a region of (i) MUC1 and/or a KLF (e.g., KLF4); (ii) MUC1 and/or a p53 promoter; or (iii) a KLF (e.g., KLF4) and/or a p53 promoter (e.g., a PE21 element of a p53 promoter) of interest from the x-ray crystallographic and/or NMR data using a computer as described above. Such a model can be constructed from analytical data points inputted into the computer by an input device and by means of a processor using known software packages, e.g., HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, or CHAIN. The model constructed from these data can be visualized via an output device of a computer, using available systems, e.g., Silicon Graphics, Evans and Sutherland, SUN, Hewlett Packard, Apple Macintosh, DEC, IBM, or Compaq.

C. Compounds

Compounds identified in any of the methods described herein, or any compound with appropriate activity useful in any of the methods described herein, include various chemical classes. Compounds can be biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, polynucleotide analogs, and small molecules. Compounds can be both small or large molecule compounds.

Typically small molecule compounds are relatively small organic molecules having a molecular weight in the range of about 50 to 2,500 daltons. These compounds can comprise functional groups necessary for structural interaction with proteins (e.g., hydrogen bonding), and can include at least an amine, carbonyl, hydroxyl, or carboxyl group, and preferably at least two of the functional chemical groups. These compounds can often comprise cyclical carbon or heterocyclic structures and/or aromatic or polyaromatic structures (e.g., purine core) substituted with one or more of the above functional groups.

Also of interest as small molecule compounds in some of the methods described herein are nucleic acid aptamers, which are relatively short nucleic acid (DNA, RNA or a combination of both) sequences that bind with high avidity to a variety of proteins and inhibit the binding to such proteins of ligands, receptors, and other molecules. Aptamers are generally about 25-40 nucleotides in length and have molecular weights in the range of about 18-25 kDa. Aptamers with high specificity and affinity for targets can be obtained by an in vitro evolutionary process termed SELEX (systemic evolution of ligands by exponential enrichment) [see, for example, Zhang et al. (2004) Arch. Immunol. Ther. Exp. 52: 307-315, the disclosure of which is incorporated herein by reference in its entirety]. For methods of enhancing the stability (by using nucleotide analogs, for example) and enhancing in vivo bioavailability (e.g., in vivo persistence in a subject's circulatory system) of nucleic acid aptamers see Zhang et al. (2004) and Brody et al. [(2000) Reviews in Molecular Biotechnology 74: 5-13, the disclosure of which is incorporated herein by reference in its entirety].

Large molecule compounds can include large proteins such as antibodies or macromolecular complexes comprising two or more proteins. Large molecule compounds, particularly those that are composed of more than one polypeptide, can be covalently joined or non-covalently joined, e.g., by hydrogen bonding, Van der Waals forces, or hydrophobic interactions.

Compounds can be identified from a number of potential sources, including: chemical libraries, natural product libraries, and combinatorial libraries comprised of random peptides, oligonucleotides, or organic molecules. Chemical libraries consist of random chemical structures, some of which are analogs of known compounds or analogs or compounds that have been identified as "hits" or "leads" in other drug discovery screens, while others are derived from natural products, and still others arise from non-directed synthetic organic chemistry. Natural product libraries are collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282: 63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries.

Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8: 701-707 (1997). Identification of test compounds through the use of the various libraries described herein permits subsequent modification of the test compound "hit" or "lead" to optimize the capacity of the "hit" or "lead" to inhibit the interaction between, e.g., a KLF and MUC1, a KLF and a p53 promoter, or MUC1 and a p53 promoter.

Inhibitory compounds can be large molecules such as antibodies, or antigen-binding antibody fragments, specific for, e.g., MUC1 or a KLF. Such antibodies will generally bind to, or close to: (a) the region of MUC1 to which a KLF (e.g., KLF4) binds (e.g., MUC1-CD); (b) the region on a KLF to which MUC1 binds; (c) the region of a MUC1 to which a p53 promoter binds; or (d) the region of a KLF to which a p53 promoter binds. However, as indicated above, the compounds can also act allosterically and so they can also bind to the proteins at positions other than, and even remote from, the binding sites for MUC1 (on a KLF such as KLF4) and on a KLF (e.g., KLF4) (for MUC1 or a MUC1-CD). Antibodies could also, e.g., bind to the DNA binding domain of a KLF and thus prevent the binding of this molecule to a p53 promoter. As used throughout the present application, the term "antibody" refers to a whole antibody (e.g., IgM, IgG, IgA, IgD, or IgE) molecule that is generated by any one of a variety of methods that are known in the art. The antibody can be made in or derived from any of a variety of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The antibody can be a purified or a recombinant antibody. Also useful for the invention are antibody fragments and chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies [Poljak (1994) Structure 2(12): 1121-1123; Hudson et al. (1999) J. Immunol. Methods 23(1-2): 177-189, the disclosures of both of which are incorporated herein by reference in their entirety] and intrabodies [Huston et al. (2001) Hum. Antibodies 10(3-4): 127-142; Wheeler et al. (2003) Mol. Ther. 8(3): 355-366; Stocks (2004) Drug Discov. Today 9(22): 960-966, the disclosures of all of which are incorporated herein by reference in their entirety] can be used in the methods of the invention.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, *Current Protocols In Immunology*, Coligan et al., ed. 2.8, 2.10 (Wiley Interscience, 1991) the disclosure of which is incorporated herein by reference in their entirety. scFv fragments can be produced, for example, as described in U.S. Pat. No. 4,642,334, the disclosure of which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225, 539; Jones et al. (1986) Nature 321, 552-25; Veroeyan et al. (1988) Science 239, 1534; and Beidler et al. (1988) J. Immunol. 141, 4053-60. The disclosures of all these articles and patent documents are incorporated herein by reference in their entirety.

The compounds identified above can be synthesized by any chemical or biological method. The compounds identified above can also be pure, or can be in a formulation (e.g., a pharmaceutical composition) with one or more additional non-active ingredients (e.g., additional compounds or constituents which do not bind to or inhibit the interaction between a KLF (e.g., KLF4) and MUC1 (e.g., MUC1-CD); MUC1 and a p53 promoter, or a KLF (e.g., KLF4) and a p53 promoter and can be prepared in an assay-, physiologic-, or pharmaceutically-acceptable diluent or carrier (see Pharmaceutical Compositions and Methods of Treatment below). A composition can also contain one or more additional therapeutic agents (see below).

D. Pharmaceutical Compositions and Methods of Treatment

The present invention also provides pharmaceutical compositions comprising one or more therapeutically effective amounts of a compound, or a pharmaceutically acceptable salt thereof, together with a pharmaceutically acceptable carrier, diluent, or excipient therefor. A compound that has the ability to, for example, (a) inhibit the interaction between MUC1 and a KLF (e.g., KLF4), (b) inhibit the interaction between KLF (e.g., KLF4) and a p53 promoter, (c) inhibit the interaction of MUC1 (e.g., MUC1-CD) with a p53 promoter; (d) inhibit the growth of a cell (e.g., a colon cancer cell, a breast cancer cell, a prostate cancer cell, a lung cancer cell, a lymphoma, or an inflammatory cell such as a proliferating T-cell), (e) increasing p53 activity, (f) inhibit histone deacetylation, (g) inhibit the interaction between MUC1 and/or a KLF and a PE21 element, or (h) inhibit an interaction between an HDAC and a p53 promoter can be considered a compound. Such compounds can be, but are not necessarily, those identified by any of the screening methods described herein.

Any of the compounds described herein can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds can also be incorporated into the compositions.

A pharmaceutical composition is formulated to be compatible with its intended route of administration. Examples of routes of administration include oral, rectal, and parenteral, e.g., intravenous, intramuscular, intradermal, subcutaneous, inhalation, transdermal, or transmucosal. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite, chelating agents such as ethylenediaminetetraacetic acid, buffers such as acetates, citrates or phosphates and agents for the adjustment of tonicity such as sodium chloride or dextrose. pH can be adjusted with acids or bases, such as hydrochloric acid or sodium hydroxide. The compositions can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL3 (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contamination by microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of contamination by microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be facilitated by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes, a glidant such as colloidal silicon dioxide, a sweetening agent such as sucrose or saccharin, or a flavoring agent such as peppermint, methyl salicylate, or orange flavoring.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

The dose administered to a subject, in the context of the present invention should be sufficient to affect a beneficial therapeutic response in the subject over time. The term "subject" refers to a member of the class Mammalia. Examples of mammals include, without limitation, humans (e.g., a human patient), non-human primates (e.g., chimpanzees, baboons, or monkeys), mice, rats, rabbits, guinea pigs, gerbils, hamsters, horses, livestock (e.g., cows, pigs, sheep, or goats), dogs, cats, or whales.

The dose will be determined by the efficacy of the particular compound employed and the condition of the subject, as well as the body weight or surface area of the subject to be treated. The size of the dose also will be determined by the existence, nature, and extent of any adverse side effects that accompany the administration of a particular compound in a particular subject. In determining the effective amount of the compound to be administered in the treatment or prophylaxis of the disease being treated, the medical or veterinary professional can evaluate factors such as the circulating plasma levels of the compound, compound toxicities, and/or the progression of the disease, etc. In general, the dose equivalent of a compound is from about 1 µg/kg to 100 mg/kg for a typical subject. Many different administration methods are known to those of skill in the art.

For administration, compounds of the present invention can be administered at a rate determined by factors that can include, but are not limited to, the pharmacokinetic profile of the compound, contraindicated drugs, and the side effects of the compound at various concentrations, as applied to the mass and overall health of the subject. Administration can be accomplished via single or divided doses.

Toxicity and therapeutic efficacy of such compounds can be determined by known pharmaceutical procedures in, for example, cell cultures or experimental animals (animal models of cancer, e.g., colon, breast, prostate, or lung cancer models). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in to minimize potential damage to normal cells (e.g., non-cancerous cells) and, thereby, reduce side effects.

The data obtained from the cell culture assays and animal studies can be used in formulating a range of dosage for use in humans. The dosage of such compounds lies generally within a range of circulating concentrations that include the $ED_{50}$ with little or no toxicity. The dosage may vary within this range depending upon the dosage form employed and the route of administration utilized. For a compound used as described herein (e.g., for treating cancer or an inflammatory condition in a subject), the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Compounds that inhibit the growth of a cell (i.e., a mammalian cell, a human cancer cell) can be any of the compounds described herein.

As defined herein, a therapeutically effective amount of a compound (i.e., an effective dosage) includes milligram or microgram amounts of the compound per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a compound depend upon the potency of the compound with respect to the inhibition of the cell growth (i.e., inhibition of the growth of a cancer cell). When one or more of these compounds is to be administered to an animal (e.g., a human) to treat an infection or a cancer, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated. One in the art will also appreciate that certain additional factors may influence the dosage and timing required to effectively treat a subject, including but not limited to the severity of the disease or disorder, previous treatments, and other diseases present. Moreover, treatment of a subject with a therapeutically effective amount of a protein, polypeptide, or antibody can include a single treatment or can include a series of treatments.

A compound or pharmaceutical composition thereof described herein can be administered to a subject as a combination therapy with another treatment, e.g., a treatment for a cancer, viral infection, or inflammation. For example, the combination therapy can include administering to the subject (e.g., a human patient) one or more additional agents that provide a therapeutic benefit to the subject who has, or is at risk of developing, (or suspected of having) a cancer. Thus, the compound or pharmaceutical composition and the one or more additional agents are administered at the same time. Alternatively, the compound can be administered first in time and the one or more additional agents administered second in time. The one or more additional agents can be administered first in time and the compound administered second in time. The compound can replace or augment a previously or currently administered therapy. For example, upon treating with a compound of the invention, administration of the one or more additional agents can cease or diminish, e.g., be administered at lower levels. Administration of the previous therapy can also be maintained. In some instances, a previous therapy can be maintained until the level of the compound (e.g., the dosage or schedule) reaches a level sufficient to provide a therapeutic effect. The two therapies can be administered in combination.

It will be appreciated that in instances where a previous therapy is particularly toxic (e.g., a treatment for cancer or inflammation with significant side-effect profiles), administration of the compound can be used to offset and/or lessen the amount of the previously therapy to a level sufficient to give the same or improved therapeutic benefit, but without the toxicity.

In some instances, when the subject is administered a compound or pharmaceutical composition of the invention the first therapy is halted. The subject can be monitored for a first pre-selected result, e.g., an improvement in one or more symptoms of a cancer or an inflammatory condition such as any of those described herein (e.g., see above). In some cases, where the first pre-selected result is observed, treatment with the compound is decreased or halted. The subject can then be monitored for a second pre-selected result after treatment with the compound is halted, e.g., a worsening of a symptom of a cancer. When the second pre-selected result is observed, administration of the compound to the subject can be reinstated or increased, or administration of the first therapy is reinstated, or the subject is administered both a compound and first therapy, or an increased amount of the compound and the first therapeutic regimen.

The compound can also be administered with a treatment for one or more symptoms of a disease (e.g., a cancer or inflammatory condition). For example, the compound can be co-administered (e.g., at the same time or by any combination regimen described above) with, e.g., a pain medication or a treatment for anemia (e.g., Erythropoietin (EPO)).

The pharmaceutical compositions can be included in a container, pack, or dispenser together with instructions for administration.

E. Methods of Inhibiting an Interaction Between MUC1 and a KLF

Provided herein are in vitro, in vivo, and ex vivo methods of inhibiting an interaction between MUC1 and a KLF (e.g., KLF4). Based on the findings described herein, it seems that the binding of MUC1 to KLF4 increases KLF4-mediated suppression of p53 (e.g., p53 mRNA, protein, and subsequent activity) and thereby promotes the development or viability of a dividing cell (e.g., a human cancer cell or a proliferating inflammatory cell such as proliferating B- or T-cell). Thus, inhibition of this interaction can have general applicability in inhibiting the growth or viability of a cancer or an inflammatory cell. Inhibition of cell growth can be a reversible inhibition of cell growth, or more preferably can be an irreversible inhibition of cell growth (i.e., causing the death of the cell). Where the methods are in vivo or ex vivo, such methods can also be useful in the treatment of cancers or inflammatory conditions, which conditions include any of the inflammatory conditions (e.g., autoimmune diseases) disclosed herein.

Inhibition of the interaction between MUC1 and a KLF can include inhibition of an interaction between MUC1 and any KLF protein (e.g., KLF4) described herein. Similarly, MUC1, as referred to in the method, can include full-length, wild-type, mature MUC1 polypeptide (SEQ ID NO:1), the MUC1-cytoplasmic domain (MUC1-CD) (SEQ ID NO:2), or a functional or KLF-binding fragment of a MUC1 polypeptide (e.g., amino acids 1-46 of the MUC1-CD as depicted in SEQ ID NO:3). The cells can include both prokaryotic (e.g., bacterial cells) and eukaryotic cells. Eukaryotic cells can include, for example, yeast, insect, plant, fish, reptile, and mammalian cells (e.g., mouse, rat, rabbit, guinea pig, dog, cat, pig, horse, goat, cow, whale, monkey, or human). The cells can be normal, transformed, or malignant and of any histological type, e.g., without limitation, epithelial cells, fibroblasts, lymphoid cells, macrophages/monocytes, granulocytes, keratinocytes, or muscle cells. Cancer cells can include cells from cancers such as, but not limited to, lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer. Suitable cell lines include those recited in the examples, e.g., breast cancer or colon cancer cell lines.

It is understood that inhibition of MUC1 or inhibition of a KLF (e.g., the KLF4) can also inhibit an interaction between MUC1 and a KLF (e.g., KLF4). As used herein, "inhibition of MUC1" or "inhibiting MUC1" is (a) inhibition of the expression of MUC1, (b) inhibition of the binding of MUC1 to another polypeptide or DNA binding partner; or (c) inhibition of MUC1 activity. Inhibition of MUC1 expression includes inhibition of MUC1 mRNA expression and/or MUC1 protein expression. Inhibition of MUC1 expression also includes increased degradation of MUC1 mRNA or protein. As used herein, "inhibition of a KLF" or "inhibiting a KLF" is (a) inhibition of the trans-repressive activity (e.g., repression of a p53 promoter) of a KLF (e.g., KLF4) and where applicable, the transactivation activity of a KLF, (b) inhibition of the expression of a KLF, or (c) inhibition of the binding of a KLF to one or more protein or DNA binding partners. Inhibition of MUC1 expression includes inhibition of MUC1 mRNA expression and/or MUC1 protein expression. Inhibition of MUC1 expression also includes increased degradation of MUC1 mRNA or protein.

Where the methods are in vitro cell-based methods or in vivo methods, the methods of inhibiting an interaction between MUC1 and a KLF (e.g., KLF4) can optionally include a step of identifying a cell as one expressing MUC1. That is, in in vivo methods, the cell can be one from the subject's cancer (or inflammatory condition), if present. Such identification can include, for example, identifying whether a cell expresses MUC1 mRNA or MUC1 protein. Suitable methods of identifying the expression of MUC1 protein or MUC1 mRNA are well known to those of skill in the art, and are described herein. These methods can include, for example, sodium dodecyl sulfate-polyacrylamide gel electrophoresis (SDS-PAGE)/western blotting techniques using antibodies specific for MUC1 (for detection of protein), or RT-PCR or northern blotting techniques for detection of mRNA expression. The cell can be any cell that expresses MUC1, e.g., a cell that expresses an endogenous or a recombinant or exogenous MUC1 mRNA or polypeptide.

The cell can also, optionally, be identified as one expressing the appropriate KLF (e.g., KLF4). Suitable detection methods for mRNA and protein include those described above. The cell can be any cell expressing the appropriate KLF, including cells that express endogenous, recombinant, or otherwise exogenous KLF mRNA or protein.

Compounds useful in the methods of inhibiting an interaction between MUC1 and a KLF can include any of the compounds described herein, or any other compounds with the appropriate inhibitory activity. Suitable compounds can include compounds, antibodies, an antibody fragments, polypeptides, or a peptidomimetics. Compounds can also include nucleic acids, for example, nucleic acids that inhibit the mRNA or protein expression of MUC1 or a KLF (e.g., siRNA or anti-sense nucleic acids). Other exemplary compounds for use in the methods include MUC1 or KLF polypeptides or their functional fragments. Examples of potential functional fragments of MUC1 include, for example, the MUC1-CD (SEQ ID NO:2) or fragments of the MUC1-CD containing amino acids 1-46 (e.g., SEQ ID NO:3), amino acids 2-71, amino acids 5-70, amino acids 10-70, amino acids 10-65, amino acids 15-70, amino acids 20-70, amino acids 25-70, amino acids 30-70, amino acids 35-70, amino acids 40-70, amino acids 45-70, amino acids 46-72 (e.g., SEQ ID NO:4), amino acids 50-70, or amino acids 55-70.

As indicated above, the binding of MUC1 to KLF4 appears to promote the KLF4-mediated suppression of p53 expression. In some embodiments of the methods of inhibiting the interaction between MUC1 and a KLF (e.g., KLF4), the cells or subjects can be further treated with one or more additional therapeutic agents. Such therapeutic agents can include, but are not limited to, one or more chemotherapeutic agents, one or more forms of ionizing radiation, one or more immunotherapy agents, or one or more hyperthermotherapy agents, such as any of the therapeutic agents described herein.

In Vitro Methods of Inhibiting an Interaction Between MUC1 and a KLF

Provided herein is an in vitro method of inhibiting an interaction between a MUC1 reagent and a KLF (e.g., KLF4) reagent. The method can be useful, for example, in scientific studies to investigate the role of MUC1 in KLF-mediated transcriptional control of p53, or any other scientific studies in which inhibiting the interaction between MUC1 and a KLF (e.g., KLF4) can be beneficial (e.g., cancer studies). Where the method is a cell-based method, it can also be useful as a further screening step, in e.g., a drug screening cascade, following the biochemical (e.g., a cell-free method of identifying a compound that inhibits the binding of a KLF to MUC1 described above) identification of a compound that inhibits the binding of a KLF to MUC1. Moreover, it can also serve as a "positive control" in assays to identify compounds with the same activity.

The method can include the steps of: contacting (i) a MUC1 reagent; (ii) a KLF reagent; or (iii) a molecular complex comprising (i) and (ii) with a compound that inhibits the interaction between MUC1 and KLF1. The complex (iii) can also include a p53 promoter reagent. The method can also, optionally, include the step of determining whether the inhibition of an interaction between a MUC1 reagent and a KLF reagent actually occurred. The method can be cell-based, and utilize any of the cells described herein (e.g., see above). The method can also, optionally, include the step of identifying a cell as one expressing MUC1 and/or KLF. Methods for identifying or detecting a cell as expressing mRNA or protein expression are well known to those in the art and are described above. Suitable concentrations of the inhibitory compound can be elucidated through routine experimentation and such optimization is well known to one of skill in the art. As described above, the cell may be co-cultured with one or more additional therapeutic agents.

It should be understood that where the cell is identified as one expressing a MUC1, the expressed MUC1 can be the MUC1 reagent of the method. For example, a cell identified as one expressing a full-length, wild-type, mature MUC1 protein would thus have at least one MUC1 reagent that is full-length, wild-type, mature MUC1 protein. Likewise, where the cell is identified as one expressing a KLF, the expressed KLF can be the KLF reagent of the method. For example, a cell identified as one expressing a full-length, wild-type, KLF protein (e.g., KLF4 protein) would thus have at least one KLF reagent that is full-length, wild-type, mature KLF protein.

Methods of determining or detecting the inhibition of an interaction between a MUC1 reagent and a KLF (e.g., KLF4) reagent are known in the art, and include, for example, in vitro and in situ methods (as described above). One method of determining inhibition of the interaction between MUC1 and KLF is an immunoprecipitation method and is set forth in the Examples below. Briefly, cells cultured in the presence of an inhibitory compound can be washed and harvested from the culture vessel. The cells can then be lysed using non-denaturing buffers that preserve protein-protein interactions, for example, buffers containing Nonidet-40 (NP-40) or Triton X-100 detergents. The lysates can then be clarified using, for example, centrifugation to remove insoluble debris. Clarified lysates can then be subjected to immunoprecipitation by adding to the lysate an antibody specific for either a KLF (e.g., KLF4) or MUC1 for a time sufficient to allow for the binding of the antibody to its cognate antigen. Antibody-protein complexes are isolated from the lysate solution by coupling the complexes to solid support matrices. Examples of such solid support matrices include insoluble beads conjugated to anti-IgG antibodies or other antibody-binding reagents, for example, bacterial Protein-A or Protein-G. Isolated immunocomplexes can then be solubilized in Laemmli buffer (optionally containing reducing agent) and subjected to SDS-polyacrylamide gel electrophoresis (SDS-PAGE). Immunoblotting of the samples using antibodies specific for one or both of MUC1 and a KLF can then be used to determine whether a compound has inhibited the interaction between MUC1 and a KLF. For example, a reduced amount of KLF protein in anti-MUC1 antibody immunoprecipitates from cells treated with a compound as compared to the amount of KLF in MUC1 immunoprecipitates from cells not treated with the compound indicates that the compound has inhibited the interaction of the two proteins. Similarly, a reduced amount of MUC1 protein in anti-KLF antibody immunoprecipitates from cells treated with a compound as compared to the amount of MUC1 in KLF immunoprecipitates from cells not treated with the compound indicates that the compound has inhibited the interaction of the two proteins.

Another method of determining inhibition of an interaction between MUC1 and a KLF is an in situ staining method. Immunostaining methods are well known to those of skill in the art and include embodiments where the cells are still viable (e.g., confocal microscopy of live cells) or are fixed cells (e.g., immunohistochemistry). Examples of such methods are set forth in the Examples below. Antibodies specific for MUC1 and KLF polypeptides are applied (e.g., administered, delivered, contacted) to cells. The antibodies are independently labeled with a different detectable label (e.g., a different colored fluorophore (e.g., rhodamine, texas red, FITC, Green fluorescent protein, Cy3, Cy5) such that they can be readily and easily distinguished from one another. Use of an appropriate microscope (e.g., a confocal microscope) with the appropriate optical filters can identify the position of the labeled antibodies in a given cell. When each of the positions of the two proteins are determined (i.e., the location of their respective detectable label within the cell as determined by antibody binding), if they are found to occupy the same space, the two proteins are said to co-localize. Thus, when two proteins co-localize in the absence of a compound but do not co-localize in the presence of a compound, this can indicate that the compound has inhibited the interaction between the two proteins. Optionally the cells can be fixed, for example, using paraformaldehyde or formaldehyde, and permeabilized using a detergent (e.g., Triton-X100).

It is understood that co-localization of two proteins (e.g., MUC1 and a KLF such as KLF4) can be due to a direct, physical interaction of two proteins or it can be due to the localization of two proteins to a given, defined site in a cell (e.g., the nucleus, the cell membrane, the endoplasmic reticulum, the mitochondria), not necessarily involving a physical association between the two proteins. For example, MUC1 and a KLF (e.g., KLF4) can co-localize in the nucleus of a cell, but in the absence of an interaction (e.g., in the presence of an inhibitor of their interaction) between them they can relocalize to distinct regions (e.g., the cytoplasm). In this regard, to define the particular localizations or organelles where localization occurs, it can be useful to use antibodies or other dyes that specifically detect the particular organelles or cellular regions of interest.

Since it appears that the binding of MUC1 to KLF may modulate the activity of the KLF transcription factor to suppress p53 gene expression, inhibiting the interaction between MUC1 and a KLF can also be determined by detecting the expression of, e.g., p53, or a p53-transactivated gene such as p21, BAX, MDM2, GADD45, 14-3-3 sigma, FAS1, FASL, NOXA, Puma, or Pirh2. Thus, where MUC1 binding to a KLF stimulates the activity of the KLF (e.g., KLF4), inhibiting the MUC1-KLF interaction could result in a decrease in the expression of the aforementioned genes. Methods of assessing KLF trans-suppression (or transactivation) activity are also well known to those of skill in the art. Cell-based methods can involve monitoring the expression of KLF (e.g., KLF4) transactivated genes such as CDKN1, iNOS, orotidine 5'-monophosphate decarboxylase (ODCase), and PKG1 (see, e.g., Feinberg et al. (2005) J. Biol. Chem. 280(46): 38247-58). Assessing target gene expression (e.g., p53 expression), at the level of mRNA or protein, can be done using a variety of in situ or in vitro techniques, including, but not limited to, methods described above (e.g., immunofluorescence and western blot (for measuring protein) or RT-PCR and northern blotting techniques (for RNA)). Alternatively, detecting an inhibition of KLF activity can be done using a KLF-responsive promoter driven reporter system (e.g., a promoter containing the PE21 element of a p53 promoter). By this method, nucleic acid vectors are designed which contain a coding sequence for a reporter gene (e.g., luciferase, chloramphenicol acetyltransferase (CAT), or green fluorescent protein (GFP)) operably linked to a p53 responsive enhancer element (e.g., the PE21 element of the p53 promoter) (see, for example, the Examples below). The vector can be introduced into a cell by any suitable transfection method. Since KLF4 suppresses p53 expression, ideally, an increase in the expression of a reporter gene in the presence of a compound as compared to in the absence of the compound indicates that the compound inhibits KLF activity (e.g., inhibits the interaction between KLF and the p53 promoter). On the other hand, in instances where KLF (e.g., KLF4) binding to a promoter increases the expression of a reporter gene (e.g., a reporter gene with a iNOS promoter sequence (see above)), a decrease in the expression of the reporter gene in the presence of a compound as compared to the expression in the absence of the compound indicates that the compound inhibits KLF activity. Methods of detecting an inhibition of KLF-driven reporter gene expression can also include RT-PCR or western blotting as described above. Preferably, the reporter gene encodes a polypeptide which is capable of giving a easily detectable signal, for example, fluorescence from a GFP reagent, or a detectable enzymatic activity, e.g., chloramphenicol acetyltransferase, alkaline phosphatase, luciferin/luciferase, or horseradish peroxidase.

Detection can also include lysis of the cells expressing the reporter gene for in vitro tests (e.g., in a test tube) for expression of the reporter gene.

Since it appears that KLF inhibits the expression of p53, a protein that controls apoptosis in a cell, inhibition of MUC1-KLF interaction could be detected as increased apoptosis of a cell containing a functional p53 gene (e.g., in the presence of an inhibitor of a MUC1-KLF interaction). For example, cells are plated on solid support matrix (e.g., a plastic tissue culture plate, or a multiwell (96 or 386-well) tissue culture plate) and grown in appropriate medium. Cells are then co-cultured in the absence or presence of an appropriate inhibitory compound and after a predetermined amount of time (e.g., 6 hours, 12 hours, 16 hours, 18 hours, 24 hours, 36 hours, 48 hours, or 72 hours) evaluated for the extent of apoptosis. In some embodiments, the cell can be exposed to sub-lethal levels of an apoptosis inducer (e.g., heat shock, a chemotherapeutic agent, or a death ligand such as FasL or TNFalpha) to sensitize cells to p53-induced apoptosis. Often, a control compound (e.g., a known inhibitor of known concentration) is also added to a sample of cells as an internal standard. In addition, a sample of cells is grown in the presence of a carrier, buffer, or solvent, in which the compound is delivered. Methods of detecting (e.g., determining or measuring) increased apoptosis in the presence of an inhibitor of MUC1-KLF interaction are myriad and well known to those of ordinary skill in the art. These methods can include, for example, counting the number of viable cells remaining in the well after the period of treatment with the compound. In this method, cells can be trypsinized from the plate, washed, stained with a dye (e.g., typan blue), and counted using a microscope or mechanical cell counter (Beckman-Coulter Z1™ Series COULTER COUNTER® Cell and Particle Counter). Since dyes like trypan blue are only taken up by dead or dying cells, this method allows for discrimination (i.e., blue or white cell) between viable and non-viable cells in a population. Another method for determining increased heat-shock-induced apoptosis in the presence of an inhibitory compound (e.g., any one of the compositions described herein) is monitoring cell death. Such methods are well known to those of skill in the art, and include propidium iodide staining of genomic DNA, or commercially available kits, such as, In situ Cell Death Detection ELISA Kit (Roche, Indianapolis, Ind.); and APO-Direct, APO-BRDU, or Annexin-FITC Apoptosis Kit (BD-Pharmingen, San Diego, Calif.). Such methods and kits for determining programmed cell death can optionally be used in conjunction with fluorescence flow cytometry (FFC) analysis. Examples of the methods and machines (instruments) useful for such methods are further described in "Methods of Increasing p53 Activity."

Any of the in vitro methods for detecting inhibition of the interaction between MUC1 and a KLF (in vivo or in vitro, or any screening methods described herein) can be performed in any format that allows for rapid preparation, processing, and analysis of multiple reactions. This can be, for example, in multi-well assay plates (e.g., 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay.

In Vivo Methods of Inhibiting an Interaction Between MUC1 and a KLF

The invention features an in vivo method of inhibiting an interaction between MUC1 and a KLF (e.g., KLF4), which includes the steps of: optionally identifying a subject as having, at risk of developing, or suspected to have a cancer comprising one or more cancer cells expressing MUC1; and delivering to the subject a compound that inhibits the interaction between MUC1 and a KLF. The method can also, optionally, include the step of (a) determining if the one or more cancer cells of the subject express MUC1 and/or KLF and/or (b) determining whether inhibition of an interaction between MUC1 and a KLF has occurred.

In one in vivo approach, a compound that inhibits binding of MUC1 to a KLF is administered to a subject. The subject can be any mammal, e.g., a human (e.g., a human patient) or a non-human primate (e.g., chimpanzee, baboon, or monkey), mouse, rat, rabbit, guinea pig, gerbil, hamster, horse, a type of livestock (e.g., cow, pig, sheep, or goat), a dog, cat, or a whale. Generally, the compounds of the invention will be suspended in a pharmaceutically-acceptable carrier (e.g., physiological saline) and administered orally, rectally, or parenterally, e.g., injected intravenously, subcutaneously, intramuscularly, intrathecally, intraperitoneally, intrarectally, intravaginally, intranasally, intragastrically, intratracheally, or intrapulmonarily. They can also be delivered directly to tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, where an inhibitory compound is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in the vicinity of the tumor cells whose proliferation it is desired to inhibit. Expression of the coding sequence can be directed to the tumor cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995), J. Mol. Med. 73: 479, the disclosure of which is incorporated herein by reference in its entirety). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. Promoters of interest include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast a mating factors, the adenoviral E1b minimal promoter, or the thymidine kinase minimal promoter. The DF3 enhancer can be particularly useful for expression of an inhibitory compound in cells that naturally express MUC1, for example, normal epithelial cells or malignant epithelial cells (carcinoma cells), e.g., breast cancer cells (see U.S. Pat. Nos. 5,565,334 and 5,874,415, the disclosures of which are incorporated herein by reference in their entirety). The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Schedules and co-administration can be any of those described herein (see, for example, "Pharmaceutical compositions and Methods of Treatment"). Routes of administration can be any of those listed above.

Ex Vivo Methods of Inhibiting an Interaction Between MUC1 and a KLF

An ex vivo strategy can involve transfecting or transducing cells obtained from the subject to be treated (or another subject) with a polynucleotide encoding a polypeptide that inhibits an interaction between MUC1 and a KLF. The transfected or transduced cells are then administered to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the inhibitory polypeptide for as long as they survive in the subject. Alternatively, tumor cells or inflammatory cells (e.g., immune cells), preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits binding of MUC1 to a KLF. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the same or another subject.

F. Methods of Inhibiting an Interaction Between a KLF and a p53 Promoter

Provided herein are in vitro, in vivo, and ex vivo methods of inhibiting an interaction between a KLF (e.g., KLF4) and a p53 promoter (e.g., the PE21 element of a p53 promoter such as the PE21 element depicted in SEQ ID NO:6). Based on the findings described herein, it appears that the binding of MUC1 to KLF potentiates KLF-mediated repression of the p53 promoter and thus can promote the development or viability of, e.g., a cancer cell (e.g., in a human tumor). Therefore, inhibition of this interaction can have general applicability in inhibiting the growth or viability of a cancer cell or an inflammatory cell. Inhibition of cell growth can be a reversible inhibition of cell growth, or irreversible inhibition of cell growth (i.e., causing the death of the cell). As above, where the methods are in vivo or ex vivo, such methods can also be useful in the treatment of cancers or inflammatory conditions.

Inhibition of the interaction between a KLF and a p53 promoter can include inhibition of an interaction between any KLF protein (e.g., KLF4 or functional fragment thereof such as the DNA binding domain of a KLF) and/or a p53 promoter as described herein. The p53 promoter, as referred to in the method, can include a human p53 promoter (e.g., the human p53 promoter having the SEQ ID NO:5) or a functional or PE21-containing fragment of a p53 promoter such as the PE21 of the human p53 promoter depicted in SEQ ID NO:6.

The methods of inhibiting an interaction between a KLF (e.g., KLF4) and a p53 promoter (e.g., a PE21 element of a human p53 promoter) can optionally include a step of identifying a cell as one expressing a KLF (e.g., KLF4) and/or MUC1. Such identification can include, for example, identifying (or detecting) whether a cell expresses MUC1 and/or KLF mRNA or protein. Suitable methods of identifying (or detecting) the expression of protein or mRNA are well known to those of skill in the art, and include those described herein. The cell can be any cell that expresses a KLF, including any cells that express an endogenous or a recombinant or exogenous KLF mRNA or polypeptide.

In some cases, the cell actually expresses p53 mRNA or protein. Thus, the method can, optionally, include the step of identifying a cell as one expressing p53 by any of the above-mentioned methodologies. However, it should be understood that any cell having a p53 promoter can be useful for the method and need not per se express p53 mRNA or protein.

Compounds useful in the methods of inhibiting an interaction between a KLF and a p53 promoter can include any of the compounds described herein, or any other compounds with the appropriate inhibitory activity. Suitable compounds include any of those described above, e.g., aptamers. Other exemplary compounds for use in the methods include KLF polypeptides or their functional fragments. Furthermore, exemplary compounds also include fragments of a p53 promoter, e.g., fragments that contain a PE21 element that is recognized and bound by a KLF. Examples of potential functional fragments of a p53 promoter include, for example, fragments comprising the PE21 of human MUC1 (SEQ ID NO:6). Exemplary compounds also include aptamers (see above).

The binding of KLF to a p53 promoter was shown to suppress the expression of p53, thus, co-culturing a cell in the presence of, or further administering to a subject (e.g., a human patient), an inhibitor of an interaction between a KLF (e.g., KLF4) and a p53 promoter and one or more additional therapeutic agents can increase the efficacy of the one or more therapeutic agents (e.g., one or more therapeutic agents for the treatment of cancer) as described above.

It is understood that the "Methods of Inhibiting an Interaction between a KLF and a p53 promoter" described herein (through obvious adaptation) can be applied to any promoter that (a) contains a PE21 element, (b) is bound by a KLF (e.g., KLF4), and (c) controls the expression of a gene negatively or positively involved in the regulation of cell (e.g., cancer or inflammatory cell) growth or apoptosis.

In Vitro Methods of Inhibiting an Interaction Between a KLF and a p53 Promoter

Provided herein is an in vitro method of inhibiting an interaction between a KLF (e.g., KLF4) reagent and a p53 promoter reagent. The method can be useful, for example, in scientific studies investigating the role of KLF in the control of p53 expression, the molecular mechanisms of p53-mediated apoptosis, or any other scientific studies in which inhibiting the interaction between a KLF (e.g., KLF4) and a p53 promoter can be beneficial. Where the method is a cell-based method, it can also be useful as a further screening step, in e.g., a drug screening cascade, following the biochemical (e.g., a cell-free method of identifying a compound that inhibits the binding of a KLF to a p53 promoter described above) identification of a compound that inhibits the binding of a KLF to a p53 promoter. Moreover, it can also serve as a "positive control" in assays to identify compounds with the same activity.

Suitable methods of determining or detecting the inhibition of an interaction between a transcription factor (e.g., a KLF (e.g., KLF4)) and a nucleic acid (e.g., a p53 promoter or a fragment of the promoter containing a PE21 element) are known in the art and are described in, e.g., Rowland et al. (2005) Nature Cell Biol. 7(11): 1074-1082. Examples of such methods are also described in detail above (see "Methods of Screening for Inhibitory Compounds, Inhibition of KLF-p53 Promoter Interactions" above).

From the findings described herein, it appears that the binding of MUC1 to KLF4 potentiates KLF4-induced suppression of the p53 gene. Thus, inhibition of the interaction between a KLF and the p53 promoter can also be determined by detecting the expression of p53 in the presence as compared to the absence of a compound. Methods of detecting or determining p53 mRNA and p53 protein levels are set forth above. p53 activity can also be determined by detecting or measuring the expression of a p53-transactivated gene, e.g., p21, BAX, MDM2, GADD45, 14-3-3 sigma, FAS1, NOXA, PUMA, FASL, or Pirh2. Methods for detecting mRNA or protein expression of any p53-transactivated gene are described herein and include, e.g., RT-PCR or western blotting techniques.

Assessing the inhibition of KLF binding to a p53 promoter can also be done using a reporter vector system driven by a p53 promoter or containing a KLF-binding element of a p53 promoter, such as the PE21 element as depicted in SEQ ID NO:6. For example, a nucleic acid vector can be designed and constructed that encodes a coding sequence for a reporter gene (e.g., luciferase, chloramphenicol acetyltransferase (CAT), or green fluorescent protein (GFP)) operably linked to a p53 promoter (e.g., the human p53 promoter sequence SEQ ID NO:5) or functional fragment thereof (e.g., the PE21 element such as the element depicted in SEQ ID NO:6) (see, e.g., Rowland et al., supra). The vector can be introduced into a cell by any suitable transfection method. Ideally, inhibition of the expression of a reporter gene in the presence of a test compound as compared to in the absence of the compound indicates that the compound inhibits KLF activity (e.g., inhibits the interaction between the KLF and a p53 promoter). In related aspects, a stimulus, such as a toxic or apoptosis-inducing signal, could be co-administered to the cells to stimulate the activity of a KLF (e.g., KLF4), e.g., where basal expression of the reporter gene is low. Inhibition of KLF-driven reporter gene expression (i.e., inhibition of the binding of a KLF to a p53 promoter) in the presence of a compound as compared to in the absence of a compound indicates that the compound inhibits KLF activity (i.e., the binding of the KLF to a p53 promoter). Methods of detecting expression of, and also an inhibition of, KLF-driven reporter gene expression can also include RT-PCR, western blotting, or detection of a detectably-labeled reporter gene expression product such as horseradish peroxidase, alkaline phosphatase, or luciferase (as described above).

Gel-shift assays can also be useful for detecting an inhibition of a KLF (e.g., KLF4) and a p53 promoter. For example, KLF protein can be contacted to a detectably labeled nucleic acid containing a p53 promoter (e.g., SEQ ID NO:5) or KLF-binding fragment thereof (e.g., a PE21 element of a p53 promoter such as the PE21 element as depicted by SEQ ID NO:6) for a time sufficient to allow the binding of the KLF protein to the nucleic acid. The mixture containing the detectably labeled nucleic acid and KLF protein is then solubilized and subjected to polyacrylamide gel-electrophoresis (PAGE).

Also subjected to PAGE is a sample containing a like amount of detectably labeled nucleic acid that has not been contacted with the KLF protein. Nucleic acids that are bound by protein are retarded in the gel as compared to nucleic acid not bound by protein. For example, an unbound nucleic acid will migrate faster in an acrylamide gel than will a nucleic acid bound by protein. Thus, protein-binding to a nucleic acid (e.g., the binding of a KLF to a detectably-labeled p53 promoter) can be detected based on the position of the detectably labeled nucleic acid in the gel. Such experiments are described in, e.g., Brown et al. (2005) Nucleic Acids Res. 33(16): 5181-5189 and Zhang et al. (2002) Endocrinology 143(1): 62-73. KLF protein contacted with the nucleic acid can be in a purified (e.g., recombinant) or can be present in a cell lysate (e.g., a lysate prepared from a cell that expresses KLF protein). The nucleic acid (e.g., the p53 promoter or KLF-binding fragment thereof) can be detectably labeled with any detectable label described herein such as a radionuclide (e.g., $^3H$, $^{32}P$, $^{33}P$, or $^{35}S$), fluorescent, or luminescent moiety. Methods of detectably labeling a nucleic acid are known in the art.

In addition, inhibition of an interaction between a KLF (e.g., KLF4) and a p53 promoter can be detected by chromatin immunoprecipitation experiments. For example, cells cultured in the presence or absence of a candidate compound, are exposed to a cross-linking agent. Lysates are prepared from the treated cells and subjected to sonication in the presence of detergents. The lysates are then subjected to immunoprecipation using an antibody specific for a KLF (e.g., KLF4) or an control IgG. Following the immunoprecipitation, proteins are removed from immunoprecipated nucleic acid. The isolated nucleic acid (DNA) is then specifically amplified by polymerase chain reaction (PCR) using sequence specific primers (e.g., to a sequence known to be bound by a KLF such as a PE21 element) and resolved by size using agarose gel electrophesis. The amount of PCR product resulting from amplification of KLF-immunoprecipitated nucleic acid is first compared to the amount of PCR product from the control immunoprecipitation (to determine specificity). Next, a decreased amount of specific, amplified PCR product (e.g., PE21 element) from cells treated with the compound as compared to cells not treated with the compound indicates that the compound inhibits an interaction between a KLF and a p53 promoter. ChIP experiments are further described in the following Examples (see, e.g., "Example 1. Materials and Methods").

Since it appears that KLF protects cells from programmed cell death (e.g., by inhibiting the expression of p53) another method of determining the inhibition of an interaction between a KLF (e.g., KLF4) and a p53 promoter is detecting increased apoptosis of a cell using, e.g., methods described above.

In Vivo Methods of Inhibiting an Interaction Between a KLF and a p53 Promoter

The invention features an in vivo method of inhibiting the interaction between a KLF (e.g., KLF4) and a p53 promoter, which includes the steps of: optionally identifying a subject as having, at risk of developing, or suspected of having, a cancer comprising one or more cancer cells expressing MUC1 and/or a KLF (e.g., KLF4); and delivering to the subject a compound that inhibits the interaction between a KLF and a p53 promoter. The method can include, optionally, the steps of: (a) determining if one or more cancer cells of the subject's cancer express MUC1 and/or a KLF and/or (b) determining whether inhibition of KLF and a p53 promoter has occurred. (suitable methods for which are described above).

The invention features an in vivo method of inhibiting the interaction between a KLF (e.g., KLF4) and a p53 promoter, which includes the steps of: optionally identifying a subject as having, at risk of developing, or suspected of having, an inflammatory condition mediated by one or more cells expressing MUC1 and/or a KLF (e.g., KLF4); and delivering to the subject a compound that inhibits the interaction between a KLF and a p53 promoter. The method can include, optionally, the steps of: (a) determining if one or more inflammatory cells express MUC1 and/or a KLF (e.g., KLF4) and/or (b) determining whether inhibition of KLF and the p53 promoter has occurred (suitable methods for which are described above).

In one in vivo approach, a compound that inhibits binding of a KLF to a p53 promoter is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depends on a variety of factors set forth in the preceding sections.

Where an inhibitory compound is a polypeptide, a polynucleotide containing a nucleic acid sequence encoding the polypeptide can be delivered to appropriate cells in a mammal as described in detail above.

Ex Vivo Methods of Inhibiting an Interaction Between a KLF and a p53 Promoter

An ex vivo strategy can involve transfecting or transducing cells obtained from the subject (or from another subject) with a polynucleotide encoding a polypeptide that inhibits an interaction between a KLF (e.g., KLF4) and a p53 promoter. The transfected or transduced cells are then administered to the subject. The cells can be any of a wide range of types including, without limitation, any of the cells described above. Such cells act as a source of the inhibitory polypeptide for as long as they survive in the subject. Alternatively, tumor cells or inflammatory cells (e.g., immune cells), preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits binding of a KLF (e.g., KLF4) to a p53 promoter (e.g., a PE21 element of a p53 promoter). These methods are known in the art of molecular biology and suitable methods are described above.

G. Methods of Inhibiting an Interaction Between MUC1 and a p53 Promoter

Provided herein are in vitro, in vivo, and ex vivo methods of inhibiting an interaction between MUC1 (e.g., the MUC1-CD) and a p53 promoter (e.g., the PE21 element of a p53 promoter such as the PE21 element depicted in SEQ ID NO:6). Based on the findings described herein, it appears that the binding of MUC1 to KLF potentiates KLF-mediated repression of the p53 promoter and thus can promote the development or viability of, e.g., a cancer cell (e.g., in a human tumor). Therefore, inhibition of this interaction can have general applicability in inhibiting the growth or viability of a cancer cell or an inflammatory cell. Inhibition of cell growth can be a reversible inhibition of cell growth, or irreversible inhibition of cell growth (i.e., causing the death of the cell). As above, where the methods are in vivo or ex vivo, such methods can also be useful in the treatment of cancers or inflammatory conditions.

The p53 promoter, as referred to in the method, can include a human p53 promoter (e.g., the human p53 promoter having the SEQ ID NO:5) or a functional or PE21-containing fragment of a p53 promoter such as the PE21 of the human p53 promoter depicted in SEQ ID NO:6.

The methods of inhibiting an interaction between MUC1 (e.g., MUC1-CD) and a p53 promoter (e.g., a PE21 element of a human p53 promoter) can optionally include a step of identifying a cell as one expressing a KLF (e.g., KLF4) and/or MUC1. Such identification can include, for example, identifying (or detecting) whether a cell expresses MUC1 and/or KLF mRNA or protein (methods for which are described above). The cell can be one that expresses MUC1, a KLF, or p53 (as described above).

The interaction between MUC1 and a p53 promoter can be a direct, physical interaction between MUC1 and a p53 promoter or the interaction can be indirect, e.g., mediated by one or more additional polypeptides such as a KLF (e.g., KLF4).

Compounds useful in the methods of inhibiting an interaction between MUC1 (e.g., MUC1-CD) and a p53 promoter can include any of the compounds described herein, or any other compounds with the appropriate inhibitory activity. Suitable compounds include any of those described above, e.g., aptamers. Other exemplary compounds for use in the methods include KLF or MUC1 (e.g., MUC1-CD) polypeptides or their functional fragments. Furthermore, exemplary compounds also include fragments of a p53 promoter, e.g., fragments that contain a PE21 element that is recognized and bound by MUC1. Examples of potential functional fragments of a p53 promoter include, for example, fragments comprising the PE21 of human MUC1 (SEQ ID NO:6). Exemplary compounds also include aptamers (see above).

In cell-based, in vivo, or ex vivo embodiments of the methods described herein, a cell can be co-cultured in the presence of, or a subject (e.g., a human patient) can be further administered, an inhibitor of an interaction between MUC1 (e.g., MUC1-CD) and a p53 promoter and one or more additional therapeutic agents can increase the efficacy of the one or more therapeutic agents (e.g., one or more therapeutic agents for the treatment of cancer) as described above.

It is understood that the "Methods of Inhibiting an Interaction between MUC1 and a p53 promoter" described herein (through obvious adaptation) can be applied to any promoter that (a) contains a PE21 element, (b) is bound by MUC1 (e.g., the MUC1-CD) and/or a KLF (e.g., KLF4), and (c) controls the expression of a gene negatively or positively involved in the regulation of cell (e.g., cancer or inflammatory cell) growth.

In Vitro Methods of Inhibiting an Interaction Between MUC1 and a p53 Promoter

Provided herein is an in vitro method of inhibiting an interaction between MUC1 (e.g., the MUC1-CD) reagent and a p53 promoter reagent. The method can be useful, for example, in scientific studies investigating the role of MUC1 in the control of p53 expression, the molecular mechanisms of p53-mediated apoptosis, or any other scientific studies in which inhibiting the interaction between MUC1 (e.g., the MUC1-CD) and a p53 promoter can be beneficial. Where the method is a cell-based method, it can also be useful as a further screening step, in e.g., a drug screening cascade, following the biochemical (e.g., a cell-free method of identifying a compound that inhibits the binding of MUC1 to a p53 promoter described above) identification of a compound that inhibits the binding of a MUC1 to a p53 promoter. Moreover, it can also serve as a "positive control" in assays to identify compounds with the same activity.

Suitable methods of determining or detecting an interaction between MUC1 and a nucleic acid (e.g., a p53 promoter or a fragment of the promoter containing a PE21 element) (and thus detecting an inhibition of this interaction) are set forth in the Examples below, and include, for example, in vitro and in situ methods. Examples of such methods are also described in detail above (see "Methods of Screening for Inhibitory Compounds, Inhibition of KLF-p53 Promoter Interactions" above).

From the findings described herein, it appears that the binding of MUC1 to KLF4 potentiates KLF4-induced suppression of the p53 gene, inhibiting the interaction between a KLF and the p53 promoter can also be determined by detecting the expression of p53 in the presence as compared to the absence of a compound. Methods of detecting or determining p53 mRNA and p53 protein levels are set forth above.

Detecting an interaction between (and thus detecting an inhibition of an interaction between) MUC1 and a p53 promoter can be done by obvious adaptations of any of the methods described above under "Methods of Inhibiting an Interaction Between a KLF and a p53 Promoter," e.g., reporter vector systems, gel-shift assays, ChIP analysis, or assays to detect apoptosis. Additional methods for detecting the interaction between MUC1 and a p53 promoter (and thus inhibition of an interaction between MUC1 and a p53 promoter) are described in the following Examples (see below).

In Vivo Methods of Inhibiting an Interaction Between MUC1 and a p53 Promoter

The invention features an in vivo method of inhibiting the interaction between MUC1 (e.g., MUC1-CD) and a p53 promoter, which includes the steps of: optionally identifying a subject as having, at risk of developing, or suspected of having, a cancer comprising one or more cancer cells expressing MUC1 and/or a KLF (e.g., KLF4); and delivering to the subject a compound that inhibits the interaction between MUC1 and a p53 promoter. The method can include, optionally, the steps of: (a) determining if one or more cancer cells of the subject's cancer express MUC1 and/or a KLF and/or (b) determining whether inhibition of MUC1 and a p53 promoter has occurred (suitable methods for which are described above).

The invention also features an in vivo method of inhibiting the interaction between a MUC1 (e.g., the MUC1-CD) and a p53 promoter, which includes the steps of: optionally identifying a subject as having, at risk of developing, or suspected of having, an inflammatory condition mediated by one or more cells expressing MUC1 and/or a KLF (e.g., KLF4); and delivering to the subject a compound that inhibits the interaction between MUC1 and a p53 promoter. The method can include, optionally, the steps of: (a) determining if one or more inflammatory cells express MUC1 and/or a KLF (e.g., KLF4) and/or (b) determining whether inhibition of MUC1 and the p53 promoter has occurred (suitable methods for which are described above).

In one in vivo approach, a compound that inhibits binding of MUC1 to a p53 promoter is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depends on a variety of factors set forth in the preceding sections.

Where an inhibitory compound is a polypeptide, a polynucleotide containing a nucleic acid sequence encoding the polypeptide can be delivered to appropriate cells in a mammal as described in detail above.

Ex Vivo Methods of Inhibiting an Interaction Between MUC1 and a p53 Promoter

An ex vivo strategy can involve transfecting or transducing cells obtained from the subject (or from another subject) with a polynucleotide encoding a polypeptide that inhibits an interaction between MUC1 (e.g., the MUC1-CD) and a p53 promoter. The transfected or transduced cells are then administered to the subject. The cells can be any of a wide range of types including, without limitation, any of the cells described above. Such cells act as a source of the inhibitory polypeptide for as long as they survive in the subject. Alternatively, tumor cells or inflammatory cells (e.g., immune cells), preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits binding of MUC1 (e.g., MUC1-CD) to a p53 promoter (e.g., a PE21 element of a p53 promoter). These methods are known in the art of molecular biology and suitable methods are described above.

H. Methods of Increasing p53 Activity

Provided herein are in vitro, in vivo, and ex vivo methods of increasing p53 activity. Based on the findings described herein, it appears that the binding of MUC1 to KLF potentiates KLF-mediated repression of the p53 promoter and thus can promote the development or viability of, e.g., a cancer cell (e.g., in a human tumor). Therefore, inhibition of this interaction can have general applicability in inhibiting the growth or viability of a cancer cell or an inflammatory cell. Inhibition of cell growth can be a reversible inhibition of cell growth, or irreversible inhibition of cell growth (i.e., causing the death of the cell). As above, where the methods are in vivo or ex vivo, such methods can also be useful in the treatment of cancers or inflammatory conditions.

As used herein, "p53 activity" is (a) the transactivation activity of p53 and where applicable, the trans-repressive activity of p53, (b) the expression of p53, or (c) non-transcription-based activities (e.g., the ability of p53 to induce apoptosis without regulating the transcription of genes). Expression of p53 includes p53 mRNA or p53 protein expression. Transactivation activity of p53 includes the ability to promote the expression of p53-responsive genes such as, but not limited to, p21, BAX, MDM2, GADD45, 14-3-3 sigma, FAS1, NOXA, PUMA, FASL, or Pirh2.

Methods of increasing p53 activity can optionally include a step of identifying a cell as one expressing a KLF (e.g., KLF4), p53, and/or MUC1. Such identification can include, for example, identifying (or detecting) whether a cell expresses MUC1, p53, and/or KLF mRNA or protein (methods for which are described above). The cell can be one that expresses MUC1, a KLF, or p53 (as described above).

Compounds useful in the methods of increasing p53 activity can include any of the compounds described herein, or any other compounds with the appropriate inhibitory activity. Suitable compounds include any of those described above. Other exemplary compounds for use in the methods include KLF or MUC1 (e.g., MUC1-CD) polypeptides or their functional fragments. Furthermore, exemplary compounds also include fragments of a p53 promoter, e.g., fragments that contain a PE21 element that is recognized and bound by MUC1. Examples of potential functional fragments of a p53 promoter include, for example, fragments comprising the PE21 of human MUC1 (SEQ ID NO:6).

In cell-based, in vivo, or ex vivo embodiments of the methods described herein, a cell can be co-cultured in the presence of, or a subject (e.g., a human patient) can be further administered, an inhibitor of an interaction between MUC1 (e.g., MUC1-CD) and a p53 promoter and one or more additional therapeutic agents can increase the efficacy of the one or more therapeutic agents (e.g., one or more therapeutic agents for the treatment of cancer) as described above.

In Vitro Methods of Increasing p53 activity

Provided herein is an in vitro method of increasing p53 activity (e.g., inhibiting MUC1 or a KLF (e.g., KLF4)). The method can be useful, for example, in scientific studies investigating the role of MUC1 in the control of p53 expression, the molecular mechanisms of p53-mediated apoptosis, or any other scientific studies in which increasing p53 activity (e.g., expression of p53) can be beneficial. Where the method is a cell-based method, it can also be useful as a further screening step, in e.g., a drug screening cascade, following the biochemical (e.g., a cell-free method of identifying a compound that increases p53 activity) identification of a compound that increase p53 activity (e.g., inhibits MUC1 or a KLF). Moreover, it can also serve as a "positive control" in assays to identify compounds with the same activity.

Suitable methods of determining or detecting p53 activity (and thus detecting an increase in this activity) are set forth in the Examples below.

Cell-based methods of determining p53 activity (and thus an inhibition of p53 activity) include detecting or measuring p53 expression (e.g., the expression of p53 mRNA and p53 protein levels) in a cell as described in detail above. For example, an increase in p53 expression in the presence of a compound as compared to p53 expression in the absence of a compound indicates that the compound increases p53 activity. p53 activity can also be determined by detecting or measuring the expression of a p53-transactivated gene, e.g., p21, BAX, MDM2, GADD45, 14-3-3 sigma, FAS1, NOXA, PUMA, FASL, or Pirh2. Methods for detecting mRNA or protein expression of any p53-transactivated gene are described herein and include, e.g., RT-PCR or western blotting techniques.

Cell-based methods of determining p53 activity also include detecting the expression of a reporter gene operably linked to a p53 target promoter (e.g., a promoter that contains a p53 binding element). Suitable methods of designing and testing a p53-responsive reporter construct are known in the art and described in, e.g., Huang et al. (2004) Proc. Natl. Acad. Sci. USA 101: 3456-3461; Warnick et al. (2001) J. Biol. Chem. 276(29): 27363-27370; and Thornborrow et al. (2002) Oncogene 21: 990-999. An exemplary p53-responsive reporter construct is p53-luc Cis Reporter Plasmid (Stratagene, La Jolla, Calif.). An increase in the expression of a reporter gene in the presence of a compound as compared to in the absence of a compound is an indication that the compound increases p53 activity.

Since p53 activity negatively controls cell growth and promotes apoptosis in a cell, p53 activity or an increase in p53 activity, can be determined by detecting or measuring cell growth (proliferation) or apoptosis. Methods of determining inhibition of cell proliferation are known in the art and described above. Cells can be co-cultured in the absence or presence of an appropriate inhibitory compound. In some instances, the cells can be co-cultured in the presence of sub-toxic amounts of a apoptosis-inducing compound (e.g., a chemotherapeutic agent, genotoxic agent, or an apoptosis-inducing ligand such as FasL or TNFalpha) to sensitize cells to cell death. Often, a control compound (e.g., a known inhibitor of known concentration) is also added to a sample of cells as an internal standard. In addition, a sample of cells can be grown in the presence of a vehicle (e.g., carrier, buffer, or solvent) in which the compound is delivered (e.g., as a control for the effects of the vehicle). Methods of detecting (e.g., determining or measuring) cell growth inhibition by a compound are myriad and well known in the art. These methods can include, for example, counting the number of cells as described above. Another method for determining cell growth inhibition in the presence of an inhibitory compound (e.g., any one of the compositions described herein) following treatment is a metabolic assay, for example, an MTT-metabolic assay (Invitrogen, USA). MTT Diphenyltetrazolium Bromide, is a tetrazolium salt (yellowish) that is cleaved to formazan crystals by the succinate dehydrogenase system which belongs to the mitochondrial respiratory chain, and is only active in viable cells. The mitochondrial succinate dehydrogenase reduces the MTT crystals into purple formazan in the presence of an electron coupling reagent. Following the treatment of the cells with a compound, the cells are exposed to the MTT reagent and the more viable cells are present in a well, the more formazan dye is produced. Extent of formazan dye can be measured, for example, using a spectrophotometer. Other commonly used methods of detecting cell growth inhibition include the monitoring of DNA synthesis. Cells grown, for example, in the presence or absence of compound are also treated with a nucleotide anolog that can incorporate into the DNA of the cell upon cell division. Examples of such nucleotide analogs include, for example, BrdU or $^3$H-thymidine. In each case, the amount of label incorporated into the cells (grown in the presence and absence of a given inhibitory agent) is quantified, and the amount of label incorporation is directly proportional to the amount of cell growth in the population of cells. In this context, cell proliferation (e.g., cancer cell proliferation) can be decreased by at least 10% (e.g., at least 15%, at least 20%, at least 25%, at least 30%, at least 35%, at least 40%, at least 50%, at least 55%, at least 60%, at least 65%, at least 70%, or at least 75% or more) relative to the cell proliferation in the absence of the inhibitor. It is understood that the methods described above can be used for detecting or measuring both cell proliferation and viability.

In some instances, the cells can be co-cultured in the presence of sub-toxic amounts of a apoptosis-inducing compound (e.g., a chemotherapeutic agent, genotoxic agent, or an apoptosis-inducing ligand such as FasL or TNFalpha) to sensitize cells to cell death. For example, cells could be cultured with a chemotherapeutic agent (e.g., carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, taxol, satraplatinum, 5-fluorouracil, vincristin, vinblastin, methotrexate, ara-C, taxotere, gencitabine, cisplatinum, adriamycin, or an analog of any of the aforementioned) and co-cultured in the presence of a compound that increases p53 activity. An increased amount of cell death in the presence of compound as compared to in the absence of the compound indicates that the compound increases p53 activity.

Comparisons of apoptosis between cells cultured with and without compound can be accomplished by measuring a host of indicators, for example, DNA fragmentation, caspase activity, loss of mitochondrial membrane potential, increased production of reactive oxygen species (ROS), intracellular acidification, chromatin condensation, phosphatidyl serine levels at the cell surface, or an increased cell permeability.

DNA fragmentation can be measured, e.g., by with the TUNEL assay (terminal deoxynucleotide transferase dUTP nick end labeling). Commercial versions of the assay are widely available, for example, APO-BrdU™ TUNEL Assay Kit (Invitrogen), APO-DIRECT™ Kit (BD-Biosciences-Pharmingen) and ApoAlert™ DNA fragmentation Assay Kit (Clontech).

Caspase activity can be measured via fluorogenic, chromogenic, and luminescent substrates specific for a given caspase (e.g., Caspase 3 or Caspase 9). Commercial kits are available for a variety of caspases such as caspase 3, caspase 7, caspase 8, and caspase 9 (see BD-Pharmingen or Invitrogen).

Loss of mitochondrial membrane potential can be measured with fluorescent dyes that selectively accumulate in various compartments of the mitochondria based on their integrity and functionality. One non-limiting example of such a dye is Mitotracker Red (Invitrogen).

Production of reactive oxygen species can be monitored with fluorescent dyes such as H2DCFDA.

Chromatin condensation can be measured with dyes such as Hoechst 33342 or propidium iodide.

Phosphotidyl serine (PS) levels can be measured at the cell surface. For example, Annexin V having a high affinity for PS, can be used to as a probe for PS on a cell surface. Numerous commercially available assay kits are suitable for such measurements (see BD-Biosciences Pharmingen).

Since p53 activity involves binding to p53-resgulated gene promoters, and thus transactivating target gene expression, non-cell-based methods of detecting p53 activity (and thus an increase in p53 activity) include gel-shift analysis. For example, p53 protein can be contacted to a detectably-labeled nucleic acid containing a p53-responsive element (e.g., a p53-transactivated gene promoter) in the presence of a compound. An increase in the amount of p53 binding to the nucleic acid in the presence of the compound as compared to in the absence of the compound is an indication that the compound increases p53 activity. Suitable methods include obvious adaptations to the methods described above.

Inhibition of a MUC1 and/or a KLF is inhibition of (a) MUC1 or a KLF expression or (b) inhibition of MUC1 or a KLF (e.g., KLF4) activity. Inhibition of expression includes inhibition of mRNA and protein expression and increased degradation of mRNA or protein. Methods for detection inhibition of MUC1 or a KLF are described above.

In Vivo Methods of Increasing p53 Activity

The invention features an in vivo method of increasing p53 activity, which includes the steps of: optionally identifying a subject as having, at risk of developing, or suspected of having, a cancer comprising one or more cancer cells expressing MUC1, p53, and/or a KLF (e.g., KLF4); and delivering to the subject a compound that increases p53 activity (e.g., a compound that inhibits MUC1 or a KLF (e.g., KLF4)). The method can include, optionally, the steps of: (a) determining if one or more cancer cells of the subject's cancer express MUC1, p53, and/or a KLF and/or (b) determining whether an increase in p53 activity has occurred (suitable methods for which are described above).

The invention also features an in vivo method of inhibiting the interaction between a MUC1 (e.g., the MUC1-CD) and a p53 promoter, which includes the steps of: optionally identifying a subject as having, at risk of developing, or suspected of having, an inflammatory condition mediated by one or more cells expressing MUC1, p53, and/or a KLF (e.g., KLF4); and delivering to the subject a compound that increases p53 activity (e.g., a compound that inhibits MUC1 or a KLF (e.g., KLF4)). The method can include, optionally, the steps of: (a) determining if one or more inflammatory cells express MUC1, p53, and/or a KLF (e.g., KLF4) and/or (b) determining whether an increase in p53 activity has occurred (suitable methods for which are described above).

In one in vivo approach, a compound that increases p53 (e.g., a compound that inhibits MUC1 or a KLF (e.g., KLF4)) is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depends on a variety of factors set forth in the preceding sections.

Where an inhibitory compound is a polypeptide, a polynucleotide containing a nucleic acid sequence encoding the polypeptide can be delivered to appropriate cells in a mammal as described in detail above.

Ex Vivo Methods of Increasing p53 Activity

An ex vivo strategy can involve transfecting or transducing cells obtained from the subject (or from another subject) with a polynucleotide encoding a polypeptide that increases p53 activity (e.g., a compound that inhibits MUC1 or a KLF (e.g., KLF4)). The transfected or transduced cells are then administered to the subject. The cells can be any of a wide range of types including, without limitation, any of the cells described above. Such cells act as a source of the inhibitory polypeptide for as long as they survive in the subject. Alternatively, tumor cells or inflammatory cells (e.g., immune cells), preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that increases p53 activity (e.g., a compound that inhibits MUC1 or a KLF (e.g., KLF4)). These methods are known in the art of molecular biology and suitable methods are described above.

I. Methods of Increasing Histone Acetylation

Provided herein are in vitro, in vivo, and ex vivo methods of increasing histone acetylation at the p53 promoter (e.g., inhibiting an HDAC (e.g., HDAC1, HDAC2, HDAC3 or HDAC4), MUC1 or a KLF such as KLF4, or inhibiting the interaction between an HDAC and the p53 promoter). Based on the findings described herein, it appears that the binding of MUC1 to KLF potentiates KLF-mediated repression of the p53 promoter, in part through recruitment of histone deacetylase (HDAC) proteins to the p53 promoter. Therefore, inhibition of MUC1, KLF, the MUC1-KLF interaction, or HDACs can have general applicability in increasing histone acetylation and thus inhibiting the growth or viability of a cancer cell or an inflammatory cell. Inhibition of cell growth can be a reversible inhibition of cell growth, or irreversible inhibition of cell growth (i.e., causing the death of the cell). As above, where the methods are in vivo or ex vivo, such methods can also be useful in the treatment of cancers or inflammatory conditions.

Methods of increasing histone acetylation can optionally include a step of identifying a cell as one expressing a KLF (e.g., KLF4), p53, an HDAC (e.g., HDAC1, HDAC2, HDAC3, or HDAC4) and/or MUC1. Such identification can include, for example, identifying (or detecting) whether a cell expresses MUC1, p53, an HDAC, and/or a KLF mRNA or protein (methods for which are described above). The cell can be one that expresses MUC1, a KLF, or p53 (as described above).

Inhibition of an HDAC (e.g., HDAC1, HDAC2, HDAC3, or HDAC4) is (a) inhibition of the expression of an HDAC; (b) inhibition of the activity of an HDAC, or (c) inhibition of the sub-cellular localization of an HDAC. Inhibition of the expression of an HDAC includes inhibition of mRNA or protein expression of an HDAC. Inhibition of the expression of an HDAC also includes increased degradation of HDAC mRNA or HDAC protein. Inhibition of the sub-cellular localization of an HDAC includes inhibition of an interaction between an HDAC and the a promoter (e.g., a p53 promoter) or inhibition of an interaction between an HDAC and a protein (e.g., inhibition of an interaction between an HDAC and a KLF) that facilitates binding to a particular sub-cellular location (e.g., binding to a p53 promoter).

Compounds useful in the methods of increasing histone acetylation can include any of the compounds described herein, or any other compounds with the appropriate inhibitory activity. Suitable compounds include any of those described above. Other exemplary compounds for use in the methods include KLF or MUC1 (e.g., MUC1-CD) polypeptides or their functional fragments. Furthermore, exemplary compounds also include fragments of a p53 promoter, e.g., fragments that contain a PE21 element that is recognized and bound by MUC1. Examples of potential functional fragments of a p53 promoter include, for example, fragments comprising the PE21 of human MUC1 (e.g., SEQ ID NO:6).

In cell-based, in vivo, or ex vivo embodiments of the methods described herein, a cell can be co-cultured in the presence of, or a subject (e.g., a human patient) can be further administered, an inhibitor of an interaction between MUC1 (e.g., MUC1-CD) and a p53 promoter and one or more additional therapeutic agents can increase the efficacy of the one or more therapeutic agents (e.g., one or more therapeutic agents for the treatment of cancer) as described above. Additional therapeutic agents also include known HDAC inhibitors such as butyrate, depsipeptide, phenylbutyrate, valproate, a trichostatin, suberoylanilide hydroxamic acid (SAHA), azelaic bishydroxamic acid (ABHA), scriptaid, pyroxamide, chlamydocin, apicidin, depudecin, MS-275, MGCD0103, PXD101, Daceca, Savisol, LBH589, PCI-24781, or ITF2357 (see, e.g., Garber (2007) Nature Biotech. 25(1): 17-19).

It is understood that the "Methods of Increasing Histone Acetylation" at the p53 promoter described herein (through obvious adaptation) can be applied to any promoter that (a) contains a PE21 element, (b) is bound by a KLF (e.g., KLF4) and MUC1 (e.g., the MUC1-CD), and (c) controls the expression of a gene negatively or positively involved in the regulation of cell (e.g., cancer or inflammatory cell) growth or apoptosis.

In Vitro Methods of Increasing Histone Acetylation

Provided herein is an in vitro method of increasing histone acetylation at the p53 promoter (e.g., inhibiting an HDAC, MUC1 or a KLF such as KLF4). The method can be useful, for example, in scientific studies investigating the role of MUC1 in the control of promoter acetylation (e.g., acetylation of the p53 promoter), the molecular mechanisms of p53-mediated apoptosis, or any other scientific studies in which increasing p53 promoter acetylation or increasing p53 activity (e.g., expression of p53) can be beneficial. Where the method is a cell-based method, it can also be useful as a further screening step, in e.g., a drug screening cascade, following the biochemical (e.g., a cell-free method of identifying a compound that increases histone acetylation at the p53 promoter) identification of a compound that increases histone acetylation at the p53 promoter. Moreover, it can also serve as a "positive control" in assays to identify compounds with the same activity.

Suitable methods of detecting inhibition of MUC1 or a KLF are described above, e.g., under "Methods of Increasing p53 Activity."

Suitable methods of determining or detecting histone acetylation (and thus detecting an increase in histone acetylation or a decrease in histone deacetylation) are known in the art and include both cell-based and non-cell based assays described below (see, e.g., Kijima et al. (1993) J. Biol. Chem. 268(30): 22429-22435 and Yoshida et al. (1990) J. Biol. Chem. 265(28): 17174-17179).

Histone acetylation, generally, can be measured, e.g., by isolating histones from cells cultured in the presence or absence of a compound that increases histone acetylation (see, e.g., Kijima et al., supra). Isolated histones are then solubilized in Laemmli buffer and subjected to SDS-PAGE. Gels can be then stained with protein-specific dyes (e.g., Coomassie Brilliant Blue or Ponceau S stain) and analyzed for the amount of histone acetylation. Acetylated histones generally migrate slower in an acrylamide gel than non-acetylated histones, thus the amount of slower migrating forms of histones (i.e., acetylated histones) can be measured in the presence and absence of a compound. An increase in the amount of histone acetylation in the presence of a compound as compared to in the absence of the compound indicates that the compound increases histone acetylation. Alternatively, acetylated histone proteins subjected to SDS-PAGE can be analyzed by western blot using antibodies that are specific to acetyl-groups or for acetylated forms of specific histones (e.g., histone H1, histone H2A, histone H2B, histone H3, or histone H4).

As HDAC molecules are generally responsible for the removal of acetyl-group modifications from histones, a compound that inhibits an HDAC can be one that increases histone acetylation. Methods for detecting inhibition of an HDAC, both in cells and in non-cell studies, are described in Kijima et al., supra, and Yoshida et al., supra. Briefly, isolated acetylated histones are contacted with an HDAC protein in the presence or absence of a compound (e.g., a compound that inhibits an HDAC) for a time sufficient to allow deactylation of the histones by the HDACs (if no inhibitor is present). Following the contacting, histones are solubilized and subjected to SDS-PAGE as described above. An increase in the amount of histone acetylation in the presence of a compound as compared to the absence of a compound indicates that the compound inhibits an HDAC.

Since the acetylation of the p53 promoter is known to induce p53 expression (and activity), methods described above under "Methods of Increasing p53 Activity" can also be used to detect an increase in histone acetylation at the p53 promoter (e.g., cell growth assays, apoptosis assays, p53-responsive reporter assays, assays to detect p53 expression, or assays to detect p53 target gene expression).

Methods of detecting the sub-cellular localization of an HDAC (and thus useful for measuring inhibition of the proper sub-cellular localization of an HDAC) are known in the art and provided in the Examples. For example, ChIP assays can be utilized to detect an interaction (or inhibition of an interaction) between an HDAC and a p53 promoter. Additional methods, useful in detecting localization or inhibition of proper localization of an HDAC, can also be adapted by obvious variations of those described above under "In vitro Methods of Inhibiting an Interaction Between MUC1 and a KLF."

In Vivo Methods of Increasing Histone Acetylation

The invention features an in vivo method of increasing histone acetylation at a p53 promoter (e.g., inhibiting an HDAC, MUC1, or a KLF) which includes the steps of: optionally identifying a subject as having, at risk of developing, or suspected of having, a cancer comprising one or more cancer cells expressing MUC1, p53, an HDAC, and/or a KLF (e.g., KLF4); and delivering to the subject a compound that increases histone acetylation (e.g., a compound that inhibits an HDAC, MUC1 or a KLF (e.g., KLF4)). The method can include, optionally, the steps of: (a) determining if one or more cancer cells of the subject's cancer express MUC1, an HDAC, p53, and/or a KLF and/or (b) determining whether an increase in histone acetylation (e.g., inhibition of an HDAC, MUC1, or a KLF) has occurred (suitable methods for which are described above).

The invention also features an in vivo method of increasing histone acetylation at a p53 promoter (e.g., inhibiting, an HDAC, MUC1, or a KLF), which includes the steps of: optionally identifying a subject as having, at risk of developing, or suspected of having, an inflammatory condition mediated by one or more cells expressing MUC1, an HDAC, p53, and/or a KLF (e.g., KLF4); and delivering to the subject a compound that increasing histone acetylation at a p53 promoter (e.g., inhibiting, an HDAC, MUC1, or a KLF). The method can include, optionally, the steps of: (a) determining if one or more inflammatory cells express MUC1, p53, and/or a KLF (e.g., KLF4) and/or (b) determining whether an increase in histone acetylation (e.g., inhibition of an HDAC, MUC1, or a KLF) has occurred (suitable methods for which are described above).

In one in vivo approach, a compound that increases histone acetylation at a p53 promoter (e.g., a compound that inhibits an HDAC, MUC1 or a KLF (e.g., KLF4)) is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depends on a variety of factors set forth in the preceding sections.

Where an inhibitory compound is a polypeptide, a polynucleotide containing a nucleic acid sequence encoding the polypeptide can be delivered to appropriate cells in a mammal as described in detail above.

Ex Vivo Methods of Increasing Histone Acetylation

An ex vivo strategy can involve transfecting or transducing cells obtained from the subject (or from another subject) with a polynucleotide encoding a polypeptide that increases histone acetylation at a p53 promoter (e.g., a compound that inhibits an HDAC, MUC1 or a KLF (e.g., KLF4)). The transfected or transduced cells are then administered to the subject. The cells can be any of a wide range of types including, without limitation, any of the cells described above. Such cells act as a source of the inhibitory polypeptide for as long as they survive in the subject. Alternatively, tumor cells or inflammatory cells (e.g., immune cells), preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that increases histone acetylation at a p53 promoter (e.g., a compound that inhibits an HDAC, MUC1 or a KLF (e.g., KLF4)). These methods are known in the art of molecular biology and suitable methods are described above.

J. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell culture. Non-transfected MCF-7 breast cancer cells and MCF-7 cells stably infected with a control siRNA (MCF-7/CsiRNA) or one expressing a MUC1siRNA (MCF-7/MUC1siRNA) were grown in Dulbecco's modified Eagle's medium (DMEM) with 10% heat-inactivated fetal bovine serum (HI-FBS), 100 µg/ml streptomycin, 100 units/ml penicillin, and 2 mM L-glutamine. Human ZR-75-1 breast cancer cells and those stably infected with a control siRNA (ZR-75-1/CsiRNA) or one expressing a MUC1siRNA (ZR-75-1/MUC1siRNA) (Wei et al. (2006) Mol. Cell. 21: 295-305) were cultured in RPMI 1640 medium supplemented with 10% HI-FBS, 100 µg/ml streptomycin, 100 units/ml penicillin, and 2 mM L-glutamine. Cells were treated with 50 µM etoposide (Sigma, St. Louis, Mo.).

Immunoblotting. Whole cell lysates were prepared from subconfluent MCF-7 cells as described in Wei et al. (2006) Mol. Cell. 21: 295-305. Immunoblot analysis was performed with anti-p53 (Ab-2, Ab-6; Oncogene Research Products), anti-MUC1-C (Ab-5; Neomarkers, Freemont, Calif.), anti-KLF4 (H-180; Santa Cruz Biotechnology), anti-β-actin (Sigma), anti-IκBα (Santa Cruz Biotechnology), or anti-PCNA (F-2; Santa Cruz Biotechnology) antibodies. Whole cell lysates were also, prior to analysis by immunoblotting, first subjected to immunoprecipitation with an anti-KLF4 antibody. Immunocomplexes were detected with enhanced chemiluminescence (ECL; PerkinElmer Life Sciences).

Transfection and reporter assays. Transfections were performed in 60 mm dishes using Fugene-6 (Roche Applied Science) or, for the luciferase assays, in 24 well plates using the calcium phosphate method (Invitrogen). Cells were transfected with the −2400-p53-Luc reporter, −2400-PE21-MUT-Luc reporter, −320-p53-Luc reporter, −320-PE21-MUT-Luc reporter (Rowland et al. (2005) Nat. Cell Biol. 7: 1074-1082) and an internal control LacZ expression plasmid (pCMV-LacZ) (Wei et al. (2001) J. Biol. Chem. 276: 16107-16112). Luciferase assays were performed with the Luciferase Assay System (Promega Corporation, Madison, Wis.) at 40 hours after transfection. Luciferase activity was normalized to that obtained for LacZ and presented as relative luciferase activity.

GST pull-down assays. GST and GST fusion proteins were purified by binding to glutathione-agarose beads (Sigma). $^{35}$S-labeled KLF4, prepared in rabbit reticulocyte lysate transcription/translation (TNT) reactions (Promega Corporation), was incubated with GST or the GST fusion proteins for 2 h at 4° C. After washing, the adsorbed proteins were resolved by SDS-PAGE and analyzed by autoradiography.

Chromatin immunoprecipitation (ChIP) and Re-ChIP assays. ChIP assays were performed as described (Shang et al. (2000) Cell 103: 843-852) using anti-MUC1-C, anti-KLF4, anti-HDAC1 (Upstate Biotechnology Inc.), anti-HDAC3 (Upstate Biotechnology Inc.), anti-Ac-H3 (Upstate Biotechnology Inc.) or anti-Ac-H4 (Upstate Biotechnology Inc.) antibodies. For Re-ChIP assays, immunocomplexes from the primary ChIP were eluted with 10 mM DTT for 30 min at 37° C., diluted 20 times with Re-ChIP buffer (20 mM Tris-HCl, pH 8.1, 1% Triton X-100, 2 mM EDTA, 150 mM NaCl) followed by reimmunoprecipitation with the indicated second antibodies (see below) and subjected again to the ChIP procedure. The final DNA extractions were amplified by PCR using primers that cover the p53 proximal promoter (PP; −118 to +14), the PE21 element (PE21; −118 to −54) and a control region (CR; −6020 to −5940). For PCR, 2 µl from a 50 µl DNA extraction were used with 30-38 cycles of amplification. The primers for the p53 proximal promoter (PP) will be (5'-GCCCTTACTTGTCATGGCGA (SEQ ID NO:8); 3'-GGCTCTAGACTTTTGAGAAGC (SEQ ID NO:9)). The primers for the PE21 region that covers PE21 motif will be (5'-GCCCTTACTTGTCATGGCGA (SEQ ID NO:10); 3'-CAATCCCATCAACCCCTGC (SEQ ID NO:11)) as described (25). The primers for the p53 control region (CR) will be (5'-TGACCTCAGGCGATCCACCTG (SEQ ID NO:12); 3'-GCACTTAAGGCCGGGTGCGGT (SEQ ID NO:13)).

Example 2

MUC1 Downregulates p53 mRNA and Protein Levels

Figure 1B:
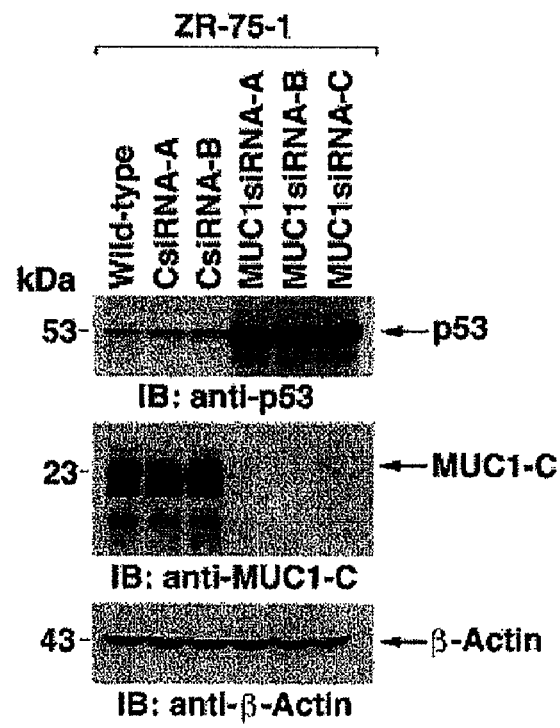
Figure 1C:
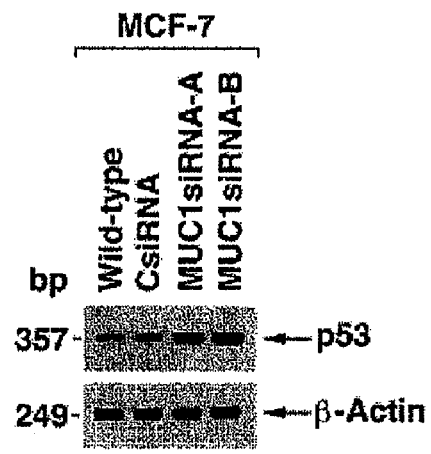
FIGS. 1C and 1D are a series of photographs of agarose gels depicting the regulation of p53 mRNA levels by MUC1. MCF-7 cells (FIG. 1C) or ZR-75-1 cells (FIG. 1D) were treated with CsiRNA or siRNAs specific for MUC1 (MUC1siRNA-A and MUC1siRNA-B). Following treatment, mRNA was isolated from the cells and subjected to semiquantitative RT-PCR for p53 and anti-β-actin mRNA levels. PCR products were resolved using agarose electrophoretic gels, which were stained with ethidium bromide and visualized using UV light. The molecular weight of each PCR product are given in units of kDa and are indicated at the left of the photographs.
Figure 1D:
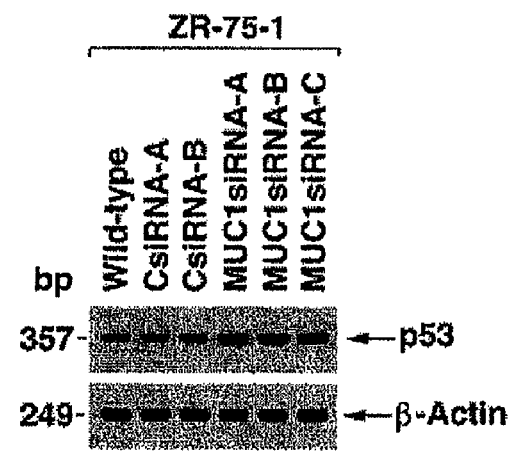
Figure 5:
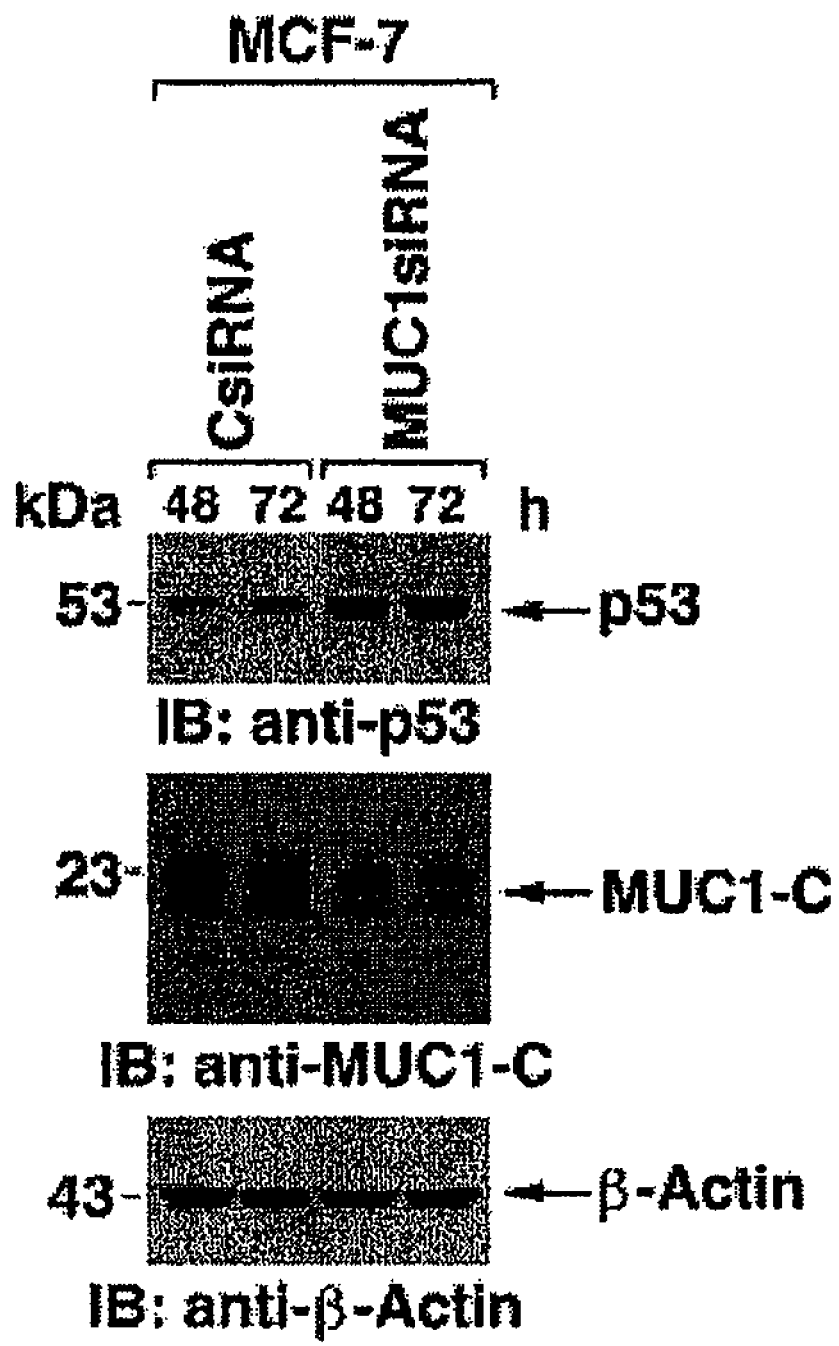
FIG. 5 is a series of photographs of immunoblots depicting the upregulation of p53 protein levels in MCF-7 cells following MUC1 silencing. MCF-7 cells were transfected with a pool of non-specific control siRNA or MUC1siRNA (Dharmacon SMARTpool Reagents) using Lipofectamine. Lysates were prepared from the transfected cells and subjected to immunoblotting ("IB") using antibodies specific for p53, MUC1-C, or β-actin as indicated below each photograph. The molecular weights of the proteins (expressed in kilodaltons (kDa)) are indicated at the left of each of the photographs.
Figure 6A:
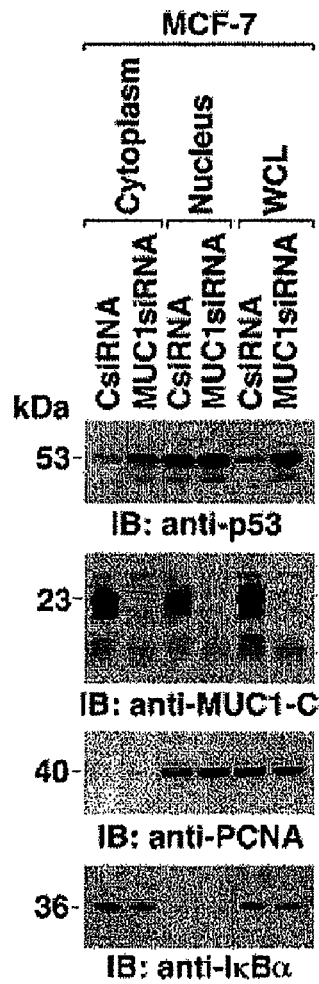
FIGS. 6A and 6B are a series of photographs of immunoblots. MCF-7 (FIG. 6A) and ZR-75-1 (FIG. 6B) cells were transfected with CsiRNA or siRNA specific for MUC1. Nuclear and cytosolic fractions from the transfected cells were prepared and subjected to immunoblotting ("IB") using antibodies specific for p53, MUC1-C, PCNA, or IκBα as indicated below each photograph. "WCL" indicates whole cell lysates. The molecular weights of the proteins (expressed in kilodaltons (kDa)) are indicated at the left of each of the photographs.
Figure 6B:
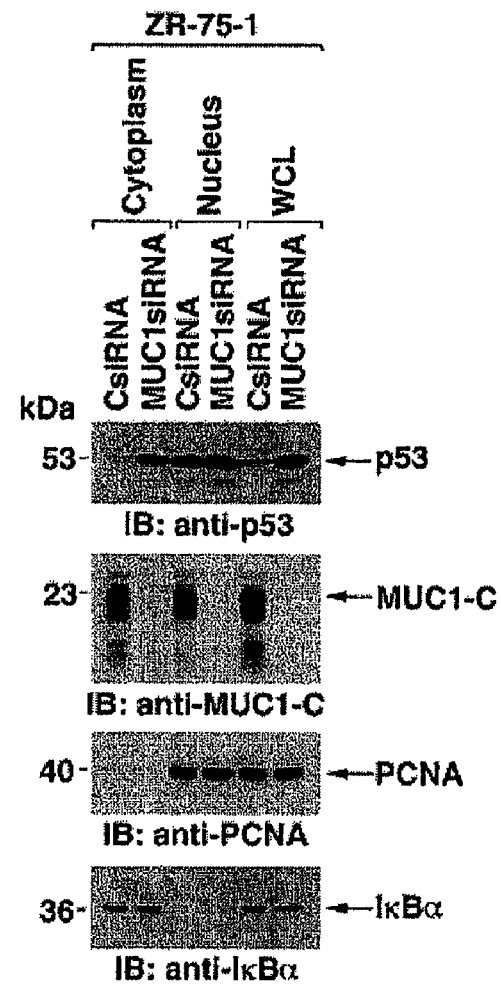

To determine whether MUC1 regulates p53 expression, human MCF-7 breast cancer cells that express endogenous MUC1 were stably infected with a retrovirus expressing a MUC1-specific siRNA (MUC1siRNA). Immunoblot analysis of two separately isolated MCF-7/MUC1 siRNA stable clones demonstrated that silencing MUC1 is associated with increases in p53 as compared to that in wild-type cells and cells expressing a control siRNA (CsiRNA) (FIG. 1A). Similarly, silencing MUC1 in human ZR-75-1 breast cancer cells by transient transfection of the cells with a pool of MUC1siRNAs (Dharmacon SMARTpool Reagents, Dharmacon, Lafayette, Colo.) was associated with an increase in p53 expression (FIG. 1B). The results show that transiently silencing MUC1 increases p53 expression (FIG. 5). Immunoblot analysis of purified nuclear and cytosolic fractions from the MCF-7 and ZR-75-1 cells demonstrated that silencing MUC1 is associated with an increase in p53 expression in the cytoplasm and nucleus (FIGS. 6A and 6B). Semiquantitative reverse transcriptase-polymerase chain reaction (RT-PCR) analysis of p53 mRNA isolated from MCF-7 and ZR-75-1 cells treated with MUC1siRNA demonstrated that p53 mRNA levels are increased by silencing MUC1 (FIGS. 1C and 1D).

Figure 7A:
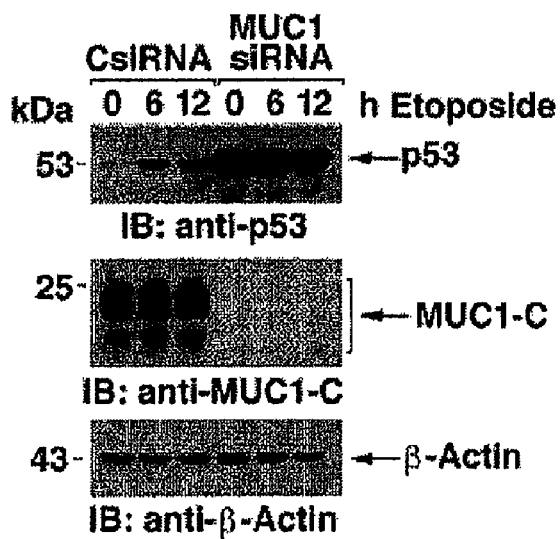
FIG. 7A is a series of photographs of immunoblots depicting the suppression of p53 levels in ZR-75-1 cells in response to DNA damage. ZR-75-1/CsiRNA and ZR-75-1/MUC1siRNA stable cells were left untreated or treated with 50 μM etoposide for 6 to 12 hours. Lysates were immunoblotted ("IB") with the antibodies indicated below each photograph. The molecular weights of the proteins (expressed in kilodaltons (kDa)) are indicated at the left of each of the photographs.

The p53 protein is stabilized in the response to DNA damage (Levine (1997) Cell 88:323-331. Treatment of MUC1-positive ZR-75-1/CsiRNA cells with the genotoxic agent, etoposide, demonstrated that p53 levels increase in the response to DNA damage (FIG. 7A). However, the p53 levels in ZR-75-1/CsiRNA cells remained substantially lower than that found in the ZR-75-1/MUC1siRNA cells (FIG. 7A). Similar results were obtained in the MCF-7/CsiRNA and MCF-7/MUC1siRNA cells. These findings and analysis of p53 mRNA levels indicate that MUC1 downregulates p53, at least in part, by a transcriptional mechanism.

Figure 2A:
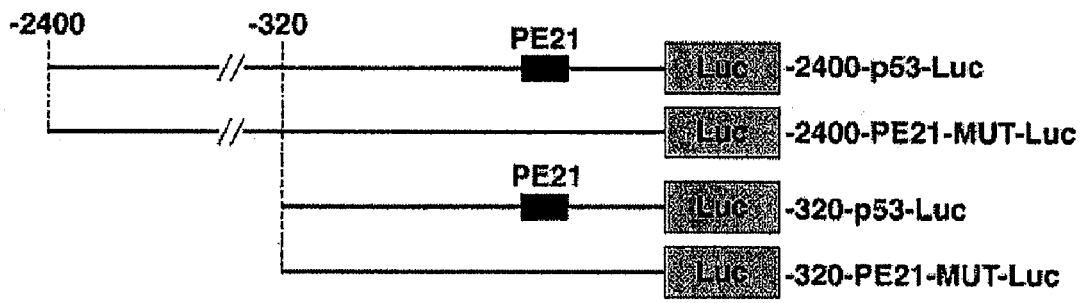
FIG. 2A is a schematic depiction of the human p53 gene promoter and mutant p53 gene promoter mutant constructs. "PE21" indicates the PE21 element of the human p53 promoter. "Luc" indicates a cDNA encoding the luciferase protein.
Figure 2B:
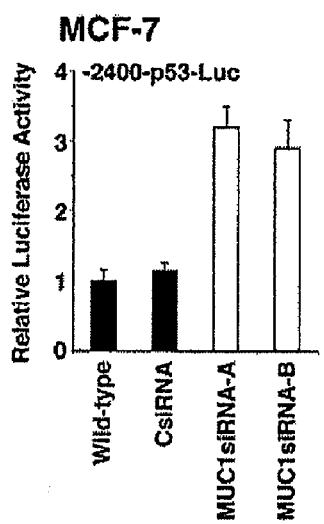
FIGS. 2B and 2C are bar graphs depicting the effect of MUC1 on the activity of the p53 promoter. MCF-7 (FIG. 2B) or ZR-75-1 cells (FIG. 2C) were transfected with the −2400-p53-Luc reporter construct with either no siRNA, control siRNAs (CsiRNA, CsiRNA-A or CsiRNA-B), or MUC1-specific siRNAs (MUC1 siRNA-A, MUC1siRNA-B, MUC1siRNA-C) (see X-axis). Whole cell lysates were prepared from each of the cell populations and analyzed for luciferase activity. The Y-axis represents the relative luciferase activity produced in the various treated cells over the no-siRNA control ("wild-type; with activity of 1).
Figure 2C:
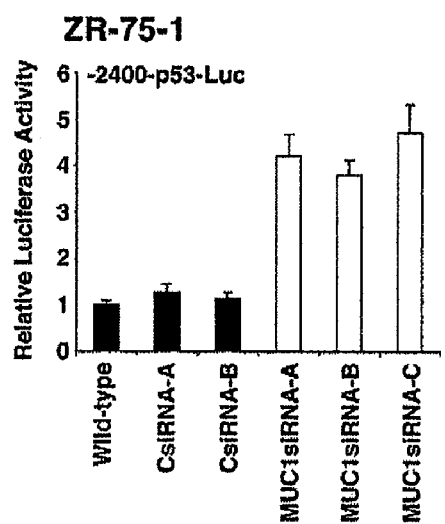

To determine if MUC1 regulates activation of the p53 promoter, cells without or with MUC1 silencing were transfected with a p53 promoter-Luc reporter (−2400-p53-Luc) (FIG. 2A) and an internal control LacZ expression plasmid (pCMV-LacZ). Following transfection, whole-cell lysates were prepared from the cells and the luciferase activity therein was measured. The luciferase assays demonstrated that p53 promoter activity is decreased in MCF-7 cells expressing endogenous MUC1 (MCF-7/CsiRNA) as compared to that in MUC1-silenced MCF-7/MUC1siRNA cells (FIG. 2B). Similar results were obtained with the ZR-75-1/CsiRNA and ZR-75-1/MUC1siRNA cells (FIG. 2C), indicating that MUC1 represses activity of the p53 promoter.

Figure 2D:
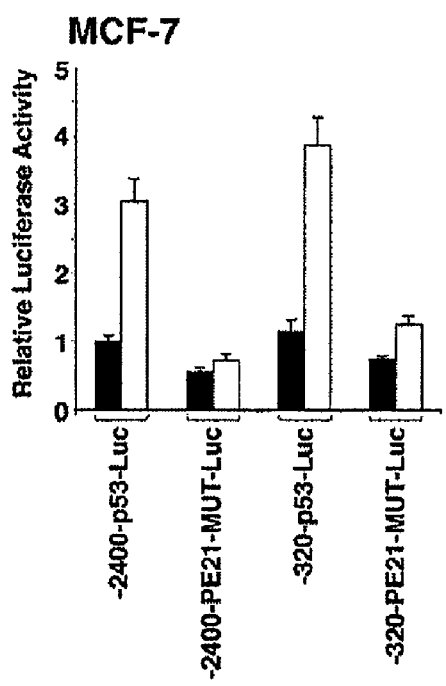
FIGS. 2D and 2E are bar graphs depicting the effect of MUC1 on the activity of the p53 promoter. MCF-7 (FIG. 2D) or ZR-75-1 cells (FIG. 2E) were transfected with either the −2400-p53-Luc reporter construct, the −2400-PE21-MUT-Luc report construct, the −320-p53-Luc reporter construct, or the −320-PE21-MUT-Luc reporter construct. Whole cell lysates were prepared from each of the cell populations and analyzed for luciferase activity. The Y-axis represents the relative luciferase activity produced in the various treated cells over or below the no-siRNA control ("wild-type; with activity of 1).
Figure 2E:
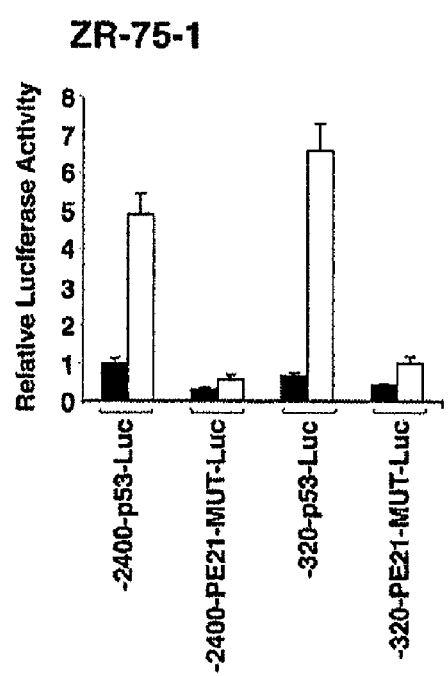

The PE21 element in the proximal promoter of the p53 gene has been shown to confer suppression of p53 transcription (Rowland et al. (2006) Nat. Rev. Cancer 6:11-23 and Noda et al. (2000) Oncogene 19:21-31). To determine whether the PE21 element is required for MUC1-mediated suppression, MCF-7 and ZR-75-1 cells without or with MUC1 silencing were transfected with p53 promoter-Luc (−2400-p53-Luc) or the reporter with a mutant PE21 element (−2400-PE21-MUT-Luc) (FIG. 2A). The promoter activity was determined by measuring luciferase activity in whole cell lysates prepared from the transfected cells. The increase in p53 promoter activity in MCF-7 cells silenced for MUC1 was abrogated by mutating the PE21 element (FIG. 2D). Similar results were obtained when using the −320-p53-Luc or −320-PE21-MUT-Luc (FIG. 2D). Activation of the p53 promoter in ZR-75-1 cells silenced for MUC1 was also abrogated by mutating the PE21 element in both −2400-p53-Luc and −320-p53-Luc (FIG. 2E). These results indicate that the PE21 element is required for MUC1-mediated suppression of the p53 promoter.

Example 3

MUC1 Occupies the p53 Proximal Promoter

Figure 3A:
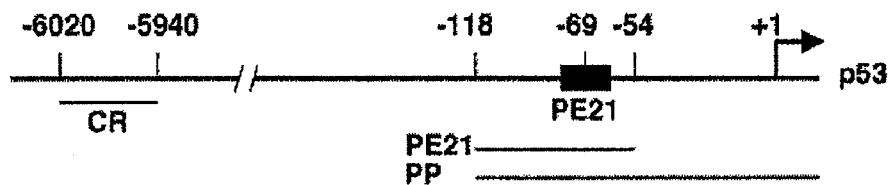
FIG. 3A is a schematic depiction of the human p53 gene promoter. "PE21" indicates the PE21 element of the human p53 promoter. "CR" indicates the position of the control region of the p53 promoter (see below under FIG. 3B) and "PP" indicates the proximal promoter region of the p53 promoter (see below under FIG. 3B. The nucleotide position of each indicated region, relative to the transcription start site ("+1"), is indicated numerically above the diagram.
Figure 3B:
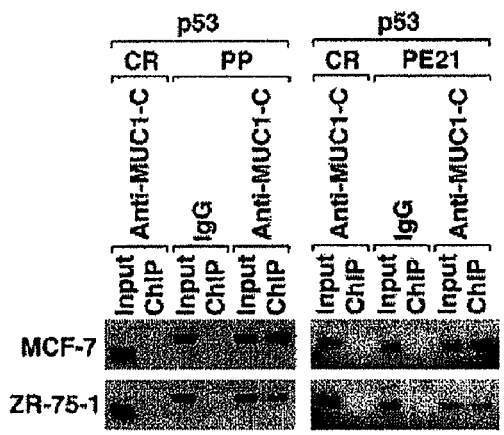
FIG. 3B is a series of photographs of agarose gels depicting the results of chromatin immunoprecipitations (ChIPs) from MCF-7 and Zr-75-1 cells. Soluble chromatin from MCF-7 and ZR-75-1 cells was prepared and subjected to immunoprecipitation using an antibody specific for MUC1-C ("anti-MUC1-C") or a control IgG ("IgG"). The DNA present in the immunoprecipitates was amplified by polymerase chain reaction (PCR) using primers that anneal to a control region ("CR"; −6020 to −5940), the proximal promoter (PP; −118 to +14), or the region that contains the PE21 element (PE21; −118 to −54) in the p53 gene promoter. PCR products were resolved using agarose electrophoretic gels, which were stained with ethidium bromide and visualized using UV light.

To study if MUC1 binds to the p53 promoter, chromatin immunoprecipitation (ChIP) assays were performed on the p53 proximal promoter (PP; −118 to +14) with an anti-MUC1-C antibody (FIG. 3A). MUC1 occupancy of the p53 proximal promoter was detectable in anti-MUC1-C, and not control IgG, precipitates (FIG. 3B). In addition, there was no detectable MUC1 associated with a control region (CR; −6020 to −5940) upstream to p53 proximal promoter (FIG. 3A). To determine whether MUC1 binds to the PE21 element (−79 to −59), ChIP analyses were performed using primers that cover the p53 promoter region from −118 to −54 (designated PE21 region; FIG. 3A). MUC1 occupancy of the PE21 region was detectable in anti-MUC1-C precipitates from MCF-7 and ZR-75-1 cells (FIG. 3B). These results indicate that MUC1 occupies the PE21 region and thereby contributes to suppression of p53 gene transcription.

Figure 3C:
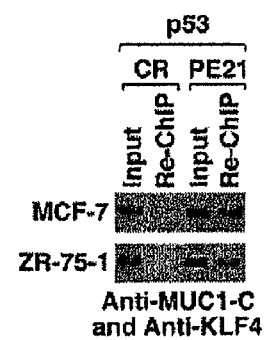
FIG. 3C is a pair of photographs of agarose gels depicting the results of Re-ChIPs from MCF-7 and ZR-75-1 cells. Soluble chromatin from MCF-7 and ZR-75-1 cells was prepared and subjected to an initial immunoprecipitation using an initial antibody specific for MUC1-C ("anti-MUC1-C") or an initial control IgG ("IgG"). The immunoprecipitated complex was released from the initial antibodies by treatment with dithiolthreitol (DTT) and subsequently diluted with Re-ChIP buffer. Free immunocomplexes were re-immunoprecipitated using antibodies specific for KLF4 or a control antibody. DNA present in the re-immunoprecipitates was amplified by polymerase chain reaction (PCR) using primers that anneal to a control region ("CR"; −6020 to −5940), the proximal promoter (PP; −118 to +14), or the region that contains the PE21 element (PE21; −118 to −54) in the p53 gene promoter. PCR products were resolved using agarose electrophoretic gels, which were stained with ethidium bromide and visualized using UV light.
Figure 7B:
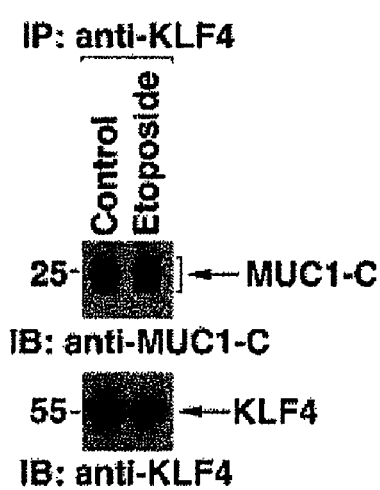
FIG. 7B is a series of photographs of immunoblots. ZR-75-1 cells were left untreated or treated with 50 μM etoposide for 12 hours. Lysates were prepared from the treated and untreated cells and subjected to immunoprecipitation using an antibody specific for KLF4 or a control IgG antibody. Immunoprecipitates were subjected to SDS-PAGE and immunoblotting ("IB") using anti-MUC1-C and anti-KLF4 antibodies (as indicated below each photograph). The molecular weights of the proteins (expressed in kilodaltons (kDa)) are indicated at the left of each of the photographs.
Figure 8A:
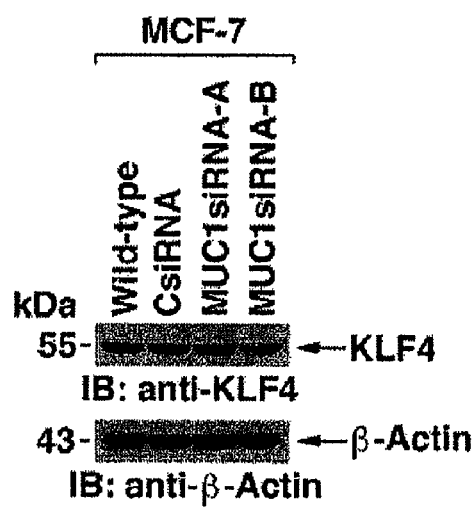
FIGS. 8A and 8B are a series of photographs of immunoblots demonstrating that MUC1 silencing has no effect on KLF4 levels. MCF-7 cells (FIG. 8A) or ZR-75-1 cells (FIG. 8B) were transfected with CsiRNA or MUC1-specific siRNAs (MUC1siRNA-A, MUC1siRNA-B, or MUC1siRNA-C). Lysates from the transfected cells were subjected to SDS-PAGE and immunoblotting using anti-KLF4 and anti-β-actin antibodies as indicated below each photograph. The molecular weights of the proteins (expressed in kilodaltons (kDa)) are indicated at the left of each of the photographs.
Figure 8B:
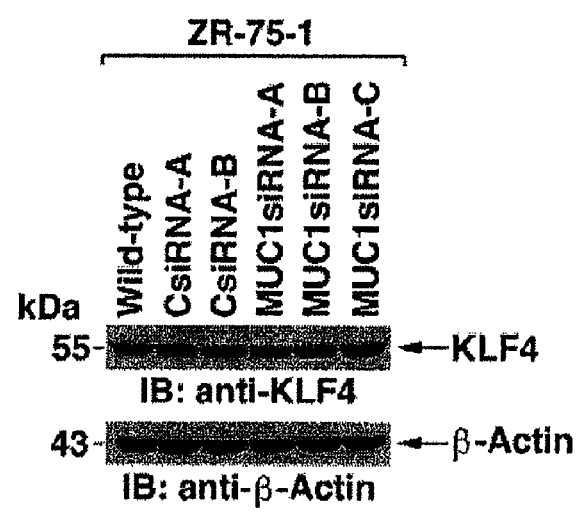

KLF4 suppresses p53 gene transcription by occupying the PE21 element of p53 gene promoter (Rowland et al. (2005) Nat. Cell Biol. 7:1074-1082). To determine if MUC1-C occupies the PE21 region with KLF4, Re-ChIP assays were performed using anti-MUC1-C and anti-KLF4 antibodies. Analysis of MCF-7 and ZR-75-1 cells showed that anti-KLF4 precipitates the PE21 region after their release from anti-MUC1-C, indicating that MUC1-C occupies the PE21 region with KLF4 (FIG. 3C). In concert with these results, it was found that MUC1-C coprecipitates with KLF4 (FIG. 7B). Moreover, DNA damage had little if any effect on this interaction (FIG. 7B). To determine if MUC1-C binds directly to KLF4, GST, GST-MUC1-CD, or GST-MUC1-CD deletion fusion proteins were incubated with [$^{35}$S]-labeled KLF4. Analysis of adsorbates to glutathione beads demonstrated that KLF4 binds to MUC1-CD(1-72) (SEQ ID NO:2) and MUC1-CD(1-46) (SEQ ID NO:3), but not with MUC1-CD (47-72) (FIG. 3D). These results indicate that KLF4 forms complexes with MUC1-C in cells by binding directly to the MUC1-CD N-terminal region (amino acids 1-46). ChIP assays were also performed with an anti-KLF4 antibody to assess whether MUC1 affects KLF4 occupancy of the p53 promoter. Notably, silencing MUC1 was associated with decreased occupancy of the PE21 region by KLF4 (FIG. 3E). By contrast, MUC1 silencing had no apparent effect on total cell KLF4 levels (FIG. 8), indicating that MUC1-C increases KLF4 occupancy of the PE21 region.

Example 4

MUC1-CD Potentiates KLF4-Mediated Repression of p53 Transcription

Figure 4A:
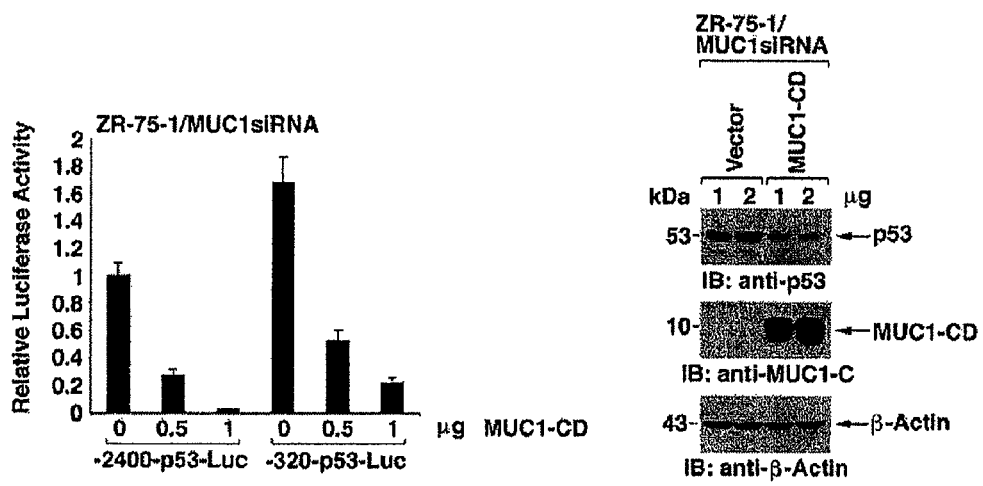
FIG. 4A is a bar graph (left) and a series of photographs of western blots (right) depicting the suppression of p53 gene transcription by MUC1. Bar graph, Left: ZR-75-1/MUC1siRNA cells were transfected with the −2400-p53-Luc reporter or the −320-p53-Luc reporter construct. The X-axis indicates the amount of MUC1-CD DNA (and a control LacZ expression plasmid) in µg ("µg MUC1-CD) also transfected into each cell. the indicated amounts of MUC1-CD. At 40 h after transfection, lysates were prepared from the transfected cells and assayed for luciferase activity. The Y-axis represents the relative luciferase activity expressed as fold activation (mean±SD of 3 separate experiments) compared to that obtained with empty vector-transfected cells (assigned a value of 1). Western blots, right: ZR-75-1/MUC1siRNA cells were transfected with the indicated amounts (in µg) of pCMV or pCMV-MUC1-CD vectors. At 24 hours after transfection, lysates from the indicated ZR-75-1/MUC1siRNA cells were immunoblotted ("IB") with antibodies specific for p53, MUC1-C, or β-actin (as indicated below each photograph). The molecular weights of the proteins (expressed in kilodaltons (kDa)) are indicated at the left of each of the photographs.
Figure 4B:
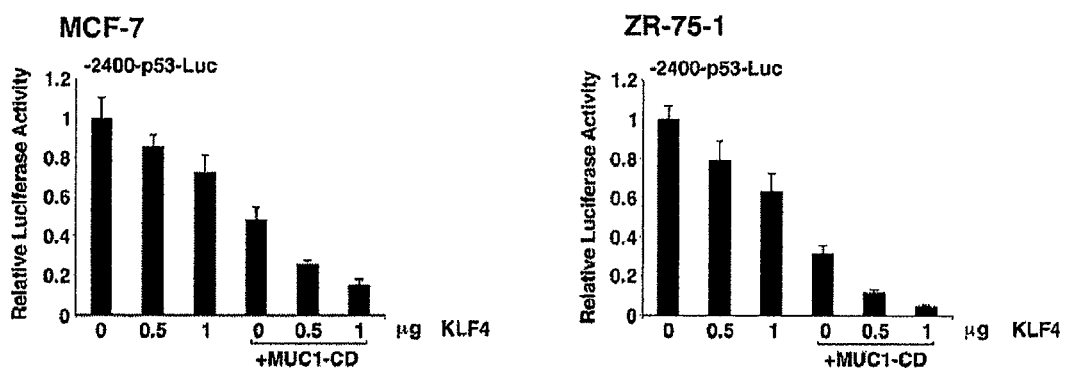
FIG. 4B is a pair of bar graphs. MCF-7 (left bar graph) or ZR-75-1 (right bar graph) cells were transfected with the −2400-p53-Luc reporter, the indicated amounts (0, 0.5, or 1 µg) of KLF4, 0.5 µg MUC1-CD and an internal control LacZ expression plasmid (pCMV-LacZ). At 40 hours after transfection, the cells were assayed for luciferase activity (as described above). The Y-axis represents the relative luciferase activity expressed as the fold activation (mean±SD of 3 separate experiments) compared to that obtained with empty vector-transfected cells (assigned a value of 1).

To determine if MUC1 affects activation of the p53 promoter, ZR-75-1/MUC1siRNA cells were transfected with −2400-p53-Luc or −320-p53-Luc and MUC1-CD. Of note, the MUC1siRNA used to silence MUC1 in the ZR-75-1 cells targets the extracellular region of MUC1-C and not the cytoplasmic domain (Ren et al. (2004) Cancer Cell 5:163-175). Results of the luciferase assays showed that MUC1-CD suppresses p53 gene transcription (FIG. 4A). Immunoblot analysis further showed that MUC1-CD downregulates p53 levels (FIG. 4A). MCF-7 and ZR-75-1 cells were also transfected with −2400-p53-Luc, MUC1-CD and increasing amounts of KLF4. The results confirmed that MUC1-CD potentiates KLF4-mediated suppression of p53 transcription (FIG. 4B).

Figure 4C:
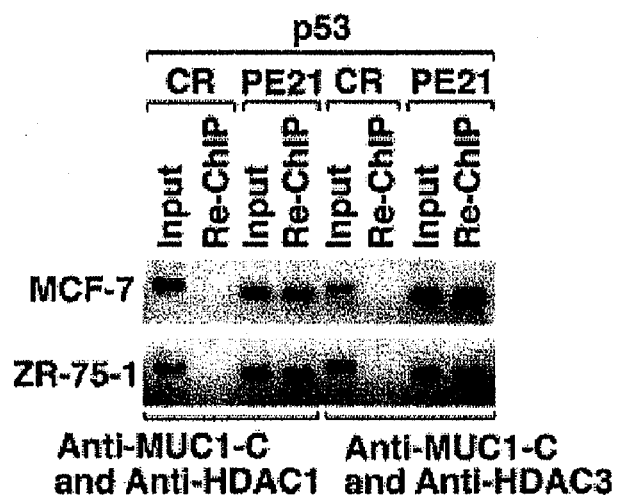
FIG. 4C is a pair of photographs of agarose gels depicting the results of Re-ChIP experiments. Soluble chromatin from MCF-7 or ZR-75-1 cells prepared and subjected to immunoprecipitation using an initial antibody specific for MUC1-C. Immunoprecipitates were eluted from the initial antibody using DTT and subsequently diluted with Re-ChIP buffer. Free immunoprecipitates were reimmunoprecipitated with antibodies specific to either HDAC1 or HDAC3 (as indicated below the photographs). DNA present in the reimmunoprecipitates was analyzed by PCR using primers that cover a control region (CR; −6020 to −5940) or the region that contains the PE21 element (PE21; −118 to −54) in the p53 gene promoter. PCR products were resolved using agarose gels, stained with ethidium bromide, and visualized using UV light.
Figure 4D:
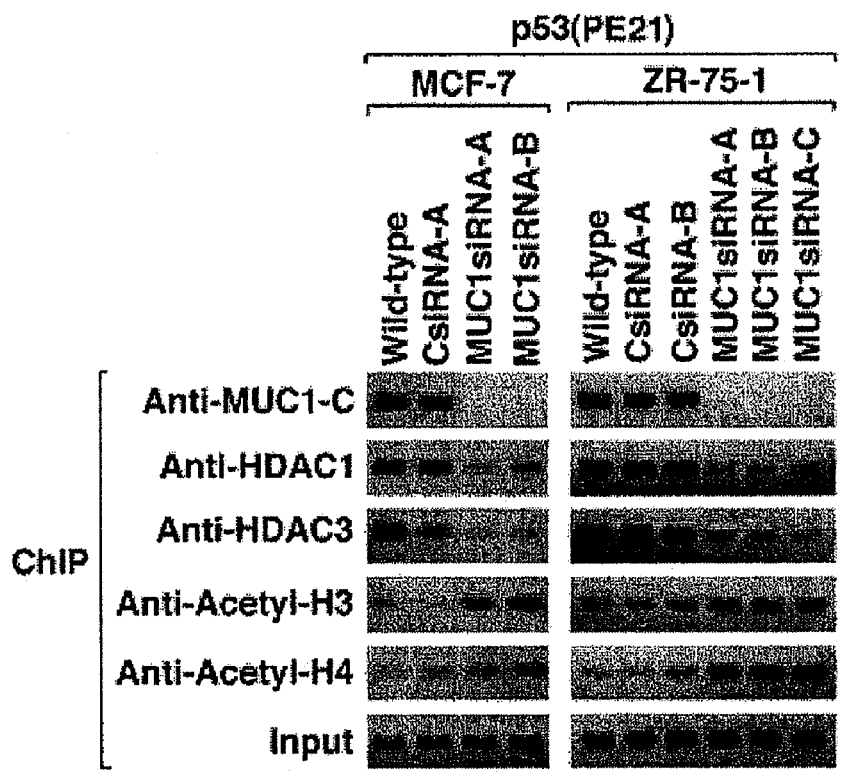
FIG. 4D is a series of photographs of agarose gels depicting the results of ChIP experiments. MCF-7 and ZR-75-1 were transfected with CsiRNA or MUC1-specific siRNAs (MUC1siRNA-A, MUC1siRNA-B). Soluble chromatin from the transfected cells was prepared and subjected to immunoprecipitation with the antibodies indicated at the left of the photographs. DNA present in the immunoprecipitates was analyzed by PCR using primers that cover a control region (CR; −6020 to −5940) or the region that contains the PE21 element (PE21; −118 to −54) in the p53 gene promoter.

Histone deacetylases (HDACs) are a family of enzymes involved in transcriptional repression by catalyzing the deacetylation of core histones (Emiliani et al. (1998) Proc. Natl. Acad. Sci. USA 95:2795-2800 and Li et al. (2002) Genes Dev. 16:687-692). To determine if MUC1 occupies the PE21 region with HDACs, Re-ChIP assays were performed using anti-MUC1-C, anti-HDAC1 and HDAC3 antibodies. Analysis of MCF-7 and ZR-75-1 cells showed that anti-HDAC1 antibody precipitates the PE21 region after release from anti-MUC1-C, indicating that MUC1-C occupies the region with HDAC1 (FIG. 4C). The results also demonstrate that MUC1 occupies the PE21 region with HDAC3 (FIG. 4C). Recruitment of HDACs plays an essential role in transcriptional repression by catalyzing the deacetylation of acetylated core histones (Emiliani et al. (1998) Proc. Natl. Acad. Sci. USA 95:2795-2800 and Li et al. (2002) Genes Dev. 16:687-692). ChIP assays from MCF-7 cells demonstrated that occupancy of the PE21 region by HDAC1 and HDAC3 is higher in MCF-7/CsiRNA cells, which express endogenous MUC1, as compared to MUC1-negative, MCF-7/MUC1 siRNA cells (FIG. 4D). It was also found that MUC1 decreases the acetylation of histone 3 and histone 4 in MCF-7/CsiRNA, as compared to MCF-7/MUC1siRNA cells (FIG. 4D). Similar results were obtained in the ZR-75-1 cells (FIG. 4D). These findings indicate that MUC1 represses activity of the p53 promoter by the recruitment of HDACs to the PE21 element and thereby deacetylation of histones.

Example 5

MUC1 Regulates Both p53 Function and Expression

Previous work demonstrated that MUC1-C binds directly to p53 and coactivates p53-mediated transcription of the p21 gene (Wei et al. (2005) Cancer Cell 7:167-178). MUC1-C also occupies the Bax proximal promoter that includes the TATA box and, in contrast to p21, represses Bax gene transcription by disrupting assembly of the basal transcription apparatus (Wei et al. (2005) Cancer Cell 7:167-178). The human p53 promoter does not have a TATA or GC box (Noda et al. (2000) Oncogene 19:21-31 and Tuck et al. (1989) Mol. Cell. Biol. 9:2163-2172). However, the PE21 element within the p53 proximal promoter directs bidirectional initiation activity as found with TATA and GC boxes (Noda et al. (2000) Oncogene 19:21-31; Xu et al. (1991) Nucleic Acids Res. 19:6699-6704; and O'Shea-Greenfield et al. (1992) J. Biol. Chem. 267:6450). The PE21 element functions as a binding site for KLF4, a repressor of p53 transcription that transforms cells as a function of p21 status (Rowland et al. (2006) Nat. Rev. Cancer 6:11-23; Rowland et al. (2005) Nat. Cell Biol. 7:1074-1082; and Noda et al. (2000) Oncogene 19:21-31). The present results demonstrate that MUC1-C binds to KLF4, occupies the PE21 region constitutively with KLF4, increases KLF4 occupancy of PE21 and suppresses p53 gene transcription in the absence of DNA damage (FIG. 5). It was also found that MUC1 contributes to the recruitment of HDAC1/3, deacetylation of core histones and repression of p53 transcription. These results indicate that, in addition to regulating the p53 transcription function, MUC1-C acts by suppressing p53 expression.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by this application.

What is claimed is:

1. A method of identifying a compound that inhibits the binding of MUC1 to a kruppel-like factor (KLF), the method comprising:

(a) contacting a MUC1 peptide segment comprising the MUC1 cytoplasmic domain (MUC1-CD) comprising SEQ ID NO:3 with a KLF4 peptide segment comprising SEQ ID NO:7 in the presence of a candidate compound; and (b) determining whether the candidate compound inhibits binding of the MUC1 peptide segment to the KLF peptide segment.

2. The method of claim 1, wherein the contacting of the MUC1 peptide segment with the KLF peptide segment in the presence of the candidate compound occurs in the further presence of a p53 promoter reagent comprising a PE21 element.

* * * * *